US011065254B2

(12) United States Patent
Gavegnano et al.

(10) Patent No.: US 11,065,254 B2
(45) Date of Patent: *Jul. 20, 2021

(54) ANTIVIRAL JAK INHIBITORS USEFUL IN TREATING OR PREVENTING RETROVIRAL AND OTHER VIRAL INFECTIONS

(71) Applicants: Emory University, Atlanta, GA (US); The United States Government as Represented by the Department of Veterans Affairs, Washington, DC (US)

(72) Inventors: Christina Gavegnano, Decatur, GA (US); Raymond F. Schinazi, Miami, FL (US)

(73) Assignees: The United States Government As Represented By The Department of Veterans Affairs, Washington, DC (US); Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/815,383

(22) Filed: Mar. 11, 2020

(65) Prior Publication Data

US 2020/0206229 A1 Jul. 2, 2020

Related U.S. Application Data

(63) Continuation of application No. 16/036,670, filed on Jul. 16, 2018, now Pat. No. 10,821,111, which is a continuation-in-part of application No. 15/594,796, filed on May 15, 2017, now Pat. No. 10,022,378, which is a continuation of application No. 14/808,860, filed on Jul. 24, 2015, now Pat. No. 9,662,332, which is a continuation of application No. 14/360,905, filed as application No. PCT/US2012/067369 on Nov. 30, 2012, now Pat. No. 9,089,574.

(60) Provisional application No. 61/570,813, filed on Dec. 14, 2011, provisional application No. 61/564,994, filed on Nov. 30, 2011.

(51) Int. Cl.
| A61K 31/519 | (2006.01) |
| A61K 31/66 | (2006.01) |
| A61K 31/70 | (2006.01) |
| A61K 45/06 | (2006.01) |
| A61K 31/7072 | (2006.01) |
| A61K 31/4045 | (2006.01) |
| A61K 31/52 | (2006.01) |
| A61K 31/536 | (2006.01) |
| A61K 31/513 | (2006.01) |

(52) U.S. Cl.
CPC ........ *A61K 31/519* (2013.01); *A61K 31/4045* (2013.01); *A61K 31/513* (2013.01); *A61K 31/52* (2013.01); *A61K 31/536* (2013.01); *A61K 31/66* (2013.01); *A61K 31/7072* (2013.01); *A61K 45/06* (2013.01); *Y02A 50/30* (2018.01)

(58) Field of Classification Search
CPC ...... A61K 31/66; A61K 31/519; A61K 31/70; C07F 9/9873; C07D 265/36; C07D 487/04; C07H 19/06
USPC ..... 514/50, 108, 230.5, 265.1; 544/244, 262
See application file for complete search history.

(56) References Cited

U.S. PATENT DOCUMENTS

| 7,593,820 B2 | 9/2009 | Wilks et al. |
| 9,089,574 B2 | 7/2015 | Gavegnano et al. |
| 9,662,332 B2 | 5/2017 | Gavegnano et al. |
| 10,022,378 B2* | 7/2018 | Gavegnano .......... A61K 31/519 |
| 2011/0092499 A1 | 4/2011 | Bourke et al. |

FOREIGN PATENT DOCUMENTS

| CN | 1729192 A | 2/2006 |
| CN | 101448826 A | 6/2009 |
| CN | 101878032 A | 11/2010 |
| WO | 02096909 A1 | 12/2002 |
| WO | 2006096270 A1 | 9/2006 |
| WO | 2007070514 A1 | 6/2007 |
| WO | 2008079521 A2 | 7/2008 |
| WO | 2008109517 A1 | 9/2008 |

(Continued)

OTHER PUBLICATIONS

Yoshiaki Takahashi et al. 2013. "In Vivo Administration of a JAK3 Inhibitor to Chronically SIV Infected Rhesus Macaques Leads to NK Cell Depletion Associated with Transient Modest Increase in Viral Loads." PLOS One, vol. 8, No. 7, pp. e70992.

(Continued)

*Primary Examiner* — Raymond J Henley, III
(74) *Attorney, Agent, or Firm* — David Bradin; Nexsen Pruet, PLLC

(57) ABSTRACT

Compounds, compositions, and methods of treatment and prevention of HIV infection are disclosed. The compounds are pyrrolo[2,3-b]pyridines and pyrrolo[2,3-b]pyrimidine JAK inhibitors. Combinations of these JAK inhibitors and additional antiretroviral compounds, such as NRTI, NNRTI, integrase inhibitors, entry inhibitors, protease inhibitors, and the like, are also disclosed. In one embodiment, the combinations include a combination of adenine, cytosine, thymidine, and guanine nucleoside antiviral agents, optionally in further combination with at least one additional antiviral agent that works via a different mechanism than a nucleoside analog. This combination has the potential to eliminate the presence of HIV in an infected patient.

20 Claims, 21 Drawing Sheets

Specification includes a Sequence Listing.

(56) References Cited

FOREIGN PATENT DOCUMENTS

| WO | 2008157207 | A2 | 12/2008 |
| WO | 2008157208 | A2 | 12/2008 |
| WO | 2009045975 | A1 | 4/2009 |
| WO | 2011109217 | A2 | 9/2011 |

OTHER PUBLICATIONS

Partial European Search Report issued in counterpart EP Application No. 20176195.4 dated Oct. 7, 2020 (forty (40) pages).

\* cited by examiner

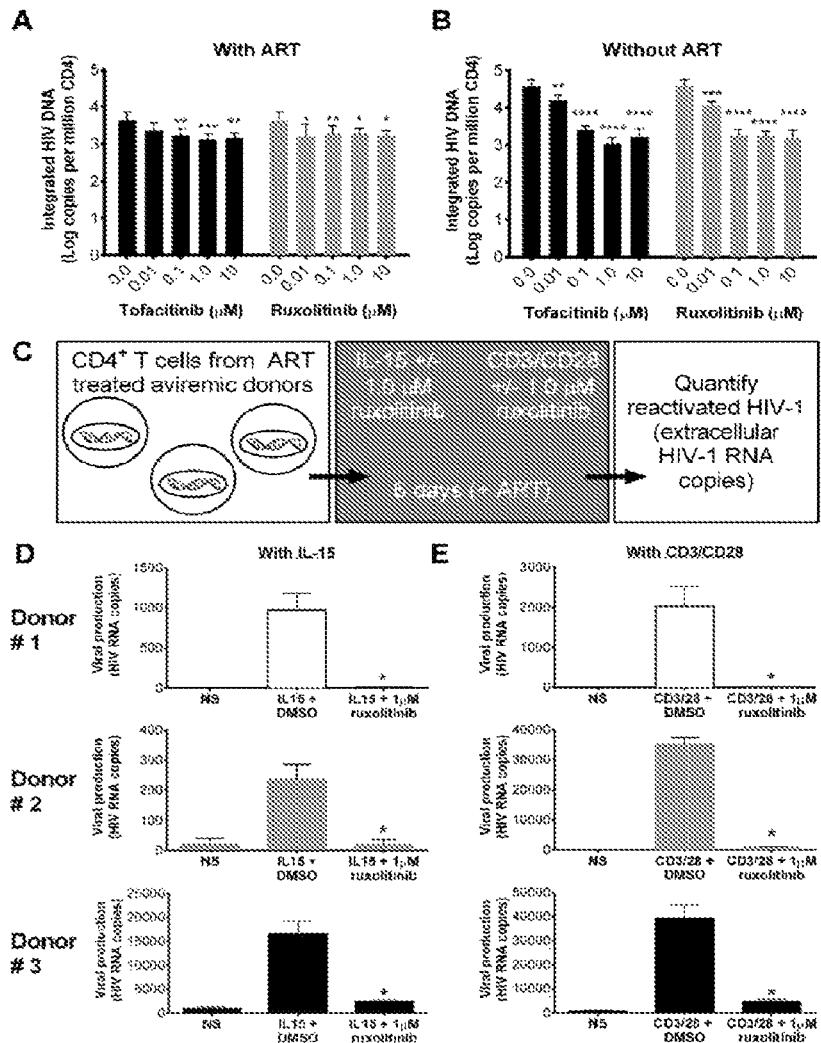
Figure 11 (A-E)

ANTIVIRAL JAK INHIBITORS USEFUL IN TREATING OR PREVENTING RETROVIRAL AND OTHER VIRAL INFECTIONS

CROSS REFERENCE TO RELATED APPLICATIONS

This application is a U.S. continuation application of U.S. application Ser. No. 16/036,670, filed Jul. 16, 2018, now U.S. Pat. No. 10,821,111, which is a U.S. continuation-in-part application under the provisions of 35 U.S.C. § 120 of U.S. patent application Ser. No. 15/594,796 filed May 15, 2017, now U.S. Pat. No. 10,022,378, which is a continuation of U.S. patent application Ser. No. 14/808,860 filed Jul. 24, 2015, now U.S. Pat. No. 9,662,332, which is a continuation of U.S. patent application Ser. No. 14/360,905 filed May 27, 2014, now U.S. Pat. No. 9,089,574, which claims priority to International Patent Application No. PCT/US 12/67369 filed Nov. 30, 2012, which in turn claims priority to U.S. Provisional Patent Application No. 61/564,994 filed Nov. 30, 2011 and U.S. Provisional Patent Application No. 61/570,813 filed Dec. 15, 2011. The disclosures of U.S. patent application Ser. No. 15/594,796, U.S. patent application Ser. No. 14/808,860, U.S. patent application Ser. No. 14/360,905, International Patent Application No. PCT/US 12/67369, U.S. Provisional Patent Application No. 61/564,994, and U.S. Provisional Patent Application No. 61/570,813 the contents of which are hereby incorporated herein by reference in their respective entireties, for all purposes.

BACKGROUND OF THE INVENTION

In 1983, the etiological cause of AIDS was determined to be the human immunodeficiency virus (HIV-1). In 1985, it was reported that the synthetic nucleoside 3'-azido-3'-deoxythymidine (AZT) inhibited the replication of human immunodeficiency virus. Since then, a number of other synthetic nucleosides, including 2',3'-dideoxyinosine (DDI), 2',3'-dideoxycytidine (DDC), 2',3'-dideoxy-2',3'-didehydrothymidine (D4 T), ((1S,4R)-4-[2-amino-6-(cyclopropylamino)-9Hpurin-9-yl]-2-cyclopentene-1-methanol sulfate (ABC), cis-2-hydroxymethyl-5-(5-fluorocytosin-1-yl)-1,3-oxathiolane ((−)-FTC), and (−)-cis-2-hydroxymethyl-5-(cytosin-1-yl)-1,3-oxathiolane (3TC), have been proven to be effective against HIV-1. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

Drug-resistant variants of HIV-1 can emerge after prolonged treatment with an antiviral agent. Drug resistance most typically occurs by mutation of a gene that encodes for an enzyme used in viral replication, and most typically in the case of HIV-1, reverse transcriptase, protease, or DNA polymerase. Recently, it has been demonstrated that the efficacy of a drug against HIV-1 infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous pressures on the virus. However, drug resistance can still emerge, and no effective cure has yet been identified, such that a patient can ultimately stop treatment.

Treatment for AIDS using attachment and fusion inhibitors as well as other antiviral drugs has been somewhat effective. Current clinical treatments for HIV-1 infections include triple drug combinations called Highly Active Antiretroviral Therapy ("HAART"). HAART typically involves various combinations of nucleoside reverse transcriptase inhibitors, non-nucleoside reverse transcriptase inhibitors, and HIV-1 protease inhibitors. In compliant patients, HAART is effective in reducing mortality and progression of HIV-1 infection to AIDS. However, these multidrug therapies do not eliminate HIV-1 and long-term treatment often results in multidrug resistance. Also, many of these drugs are highly toxic and/or require complicated dosing schedules that reduce compliance and limit efficacy. There is, therefore, a continuing need for the development of additional drugs for the prevention and treatment of HIV-1 infection and AIDS.

It would be useful to have combination therapy that minimizes the virological failure of patients taking conventional antiretroviral therapy. It would also be useful to provide a therapy that can provide a cure for HIV/AIDS, by destroying the virus altogether in all its reservoirs. The present invention provides such therapy, as well as methods of treatment using the therapy.

SUMMARY OF THE INVENTION

Antiretroviral JAK inhibitors, compositions including such inhibitors, and methods for their use in treating viral infections, are provided. Examples of viruses that can be treated using the compounds described herein include HIV, including HIV-1 and HIV-2, Flaviviridae viruses, such as HCV and Dengue, and Alphaviruses such as Chikungunya virus.

Representative JAK inhibitors include those disclosed in U.S. Pat. No. 7,598,257, an example of which is Ruxolitinib (Jakafi, Incyte), which has the structure shown below:

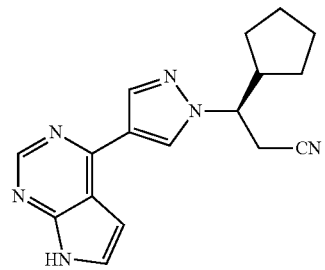 [SMILES: N#CC[C@H](C1CCCC1)n1cc(-c2ncnc3[nH]ccc23)cn1]

Representative JAK inhibitors also include those disclosed in U.S. Pat. Nos. Re 41,783; 7,842,699; 7,803,805; 7,687,507; 7,601,727; 7,569,569; 7,192,963; 7,091,208; 6,890,929, 6,696,567; 6,962,993; 6,635,762; 6,627,754; and 6,610,847, an example of which is Tofacitinib (Pfizer), which has the structure shown below:

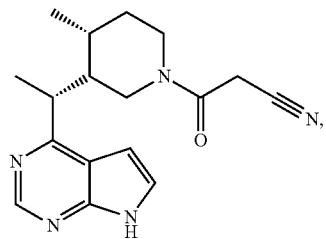 [SMILES: C[C@@H]1CCN(C(=O)CC#N)CC1[C@@H](C)c1ncnc2[nH]ccc12]

and which has the chemical name 3-{(3R,4R)-4 methyl-3-[methyl-(7H-pyrrolo[2,3-d]pyrimidin-4-yl)-amino]-piperidin-1-yl}-3-oxo-propionitrile.

In one embodiment, the compounds have the formula:

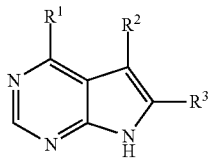

Formula A wherein:
or the pharmaceutically acceptable salt thereof; wherein
$R^1$ is a group of the formula

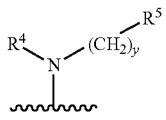

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyan, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino; $R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-S(O)$_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}$$(C_1-C_6)$alkyl wherein m is 0, 1 or 2 and $R^{15}$ and $R^{16}$ are each independently selected from hydrogen or $(C_1-C_6)$alkyl; or a group of the formula

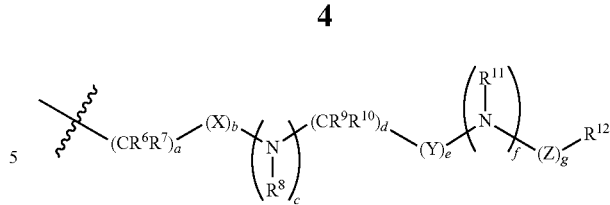

wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— or $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$ alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-S(O)$_m$, $(C_1-C_6)$alkyl-S(O)$_m$—$(C_1-C_6)$alkyl, $R^{15}R^{16}NS(O)_m$, $R^{15}R^{16}NS(O)_m(C_1-C_6)$alkyl, $R^{15}S(O)_m$ $R^{16}NR^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each independently selected from the group consisting of hydrogen, deuterium, amino, halo, hydroxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino $(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$ arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkylamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino $(C_1-C_6)$alkyl, $(C_1-C_6)$alkoxycarbonylamino, $(C_6-C_{10})$aryl ($C_1$-$C_6$)alkoxycarbonylamino, ($C_1$-$C_6$)alkylamino, (($C_1$-$C_6$)alkyl)$_2$amino, ($C_1$-$C_6$)alkylamino($C_1$-$C_6$)alkyl, (($C_1$-$C_6$)alkyl)$_2$amino($C_1$-$C_6$)alkyl, hydroxy, ($C_1$-$C_6$)alkoxy, carboxy, carboxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxy-CO—NH—, ($C_1$-$C_6$)alkyl-CO—NH—, cyano, ($C_5$-$C_9$)heterocycloalkyl, amino-CO—NH—($C_1$-$C_6$)alkylamino-CO—NH—, (($C_1$-$C_6$)alkyl)$_2$amino-CO—NH—, ($C_6$-$C_{10}$)arylamino-CO—NH—, ($C_5$-$C_9$)heteroarylamino-CO—NH—, ($C_1$-$C_6$)alkylamino-CO—NH—($C_1$-$C_6$)alkyl, (($C_1$-$C_6$)alkyl)$_2$amino-CO—NH—($C_1$-$C_6$)alkyl, ($C_6$-$C_{10}$)arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$)alkylsulfonylamino, ($C_1$-$C_6$)alkylsulfonylamino($C_1$-$C_6$)alkyl, ($C_6$-$C_{10}$)arylsulfonyl, ($C_6$-$C_{10}$)arylsulfonylamino, ($C_6$-$C_{10}$)arylsulfonylamino($C_1$-$C_6$)alkyl, ($C_1$-$C_6$)alkylsulfonylamino, ($C_1$-$C_6$)alkylsulfonylamino($C_1$-$C_6$)alkyl, ($C_5$-$C_9$)heteroaryl or ($C_2$-$C_9$)heterocycloalkyl.

The JAK inhibitors also include compounds of Formula B:

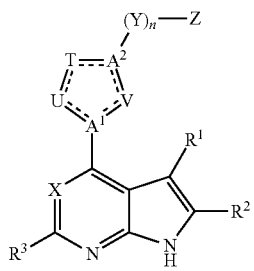

including pharmaceutically acceptable salt forms or prodrugs thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$alkyl)$R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $N_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$alkyl))$R^b$, and $S(O)_2NR^cR^d$;

wherein when Z is H, n is 1;

or the —(Y)$_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$ $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —(W)$_m$-Q;

W is $C_{1-8}$ alkylenyl, $C_{2-8}$ alkenylenyl, $C_{2-8}$ alkynylenyl, O, S, C(O), C(O)$NR^{c'}$, C(O)O, OC(O), OC(O)$NR^{c'}$, $NR^{c'}$, $NR^{c'}C(O)NR^{d'}$, S(O), S(O)$NR^{c'}$, $S(O)_2$, or S(O)2$NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halo sulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)NR^{c''}R^{d''}$, $NR^{c''}S(O)R^{b''}$, $NR^{c''}S(O)_2R^{b''}$, $S(O)R^{b''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^cC(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H and -$E^1$-$E^2$-$E^3$-$E^4$;

$D^1$ and $E^1$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^2$ and $E^2$ are independently absent or independently selected from $C_{1-6}$ alkylene, $C_{2-6}$ alkenylene, $C_{2-6}$ alkynylene, $(C_{1-6}$ alkylene$)_r$-O-$(C_{1-6}$ alkylene$)_s$, $(C_{1-6}$ alkylene$)_r$-S-$(C_{1-6}$ alkylene$)_s$, $(C_{1-6}$ alkylene$)_r$-$NR^c$-$(C_{1-6}$ alkylene$)_s$, $(C_{1-6}$ alkylene$)_r$-CO-$(C_{1-6}$ alkylene$)_s$, $(C_{1-6}$ alkylene$)_r$-COO-$(C_{1-6}$ alkylene$)_s$, $(C_{1-6}$ alkylene$)_r$-$CONR^c$-$(C_{1-6}$ alkylene$)_s$, $(C_{1-6}$ alkylene$)_r$-SO-$(C_{1-6}$ alkylene$)_s$, $(C_{1-6}$ alkylene$)_1$-$SO_2$-$(C_{1-6}$ alkylene$)_s$, $(C_{1-6}$ alkylene$)_r$-$SONR^c$-$(C_{1-6}$ alkylene$)_s$, and $(C_{1-6}$ alkylene$)_r$-$NR^cCONR^f$-$(C_{1-6}$ alkylene$)_s$, wherein each of the $C_{1-6}$ alkylene, $C_{2-6}$ alkenylene, and $C_{2-6}$ alkynylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^3$ and $E^3$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$E^4$ and $E^4$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^a$, $C(O)OR^a$, $OC(O)R^bOC(O)NR^cR^d$ $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$)R^b$, and $S(O)_2NR^cR^d$, wherein said Cis alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$;

$R^a$ is H, $Cy^1$, —$(C_{1-6}$ alkyl$)$-$Cy^1$, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^b$ is H, $Cy^1$, —$(C_{1-6}$ alkyl$)$-$Cy^1$, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$₁-$_6$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{a'}$ and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^c$ and $R^d$ are independently selected from H, $Cy^1$, —$(C_{1-6}$ alkyl$)$-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from $Cy^1$, —$(C_{1-6}$ alkyl$)$-$Cy^1$, OH, CN, amino, halo, $C_{1-6}$ alkyl, $C_{1-6}$ haloalkyl, $C_{1-6}$ haloalkyl, and halosulfanyl;

or $R^c$ and $R^d$ together with the N atom to which they are attached form a 4-, 5-, 6- or 7-membered heterocycloalkyl group optionally substituted with 1, 2, or 3 substituents independently selected from $Cy^1$, —$(C_{1-6}$ alkyl$)$-$Cy^1$, OH, CN, amino, halo, $C_{1-6}$ alkyl, $C_{1-6}$ haloalkyl, $C_{1-6}$ haloalkyl, and halosulfanyl; $R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cyclo alkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^i$ is H, CN, $NO_2$, or $C_{1-6}$ alkyl;

$R^e$ and $R^f$ are independently selected from H and $C_{1-6}$ alkyl;

$R^i$ is H, CN, or $NO_2$;

m is 0 or 1;

n is 0 or 1;

p is 0, 1, 2, 3, 4, 5, or 6;

g is 0, 1, 2, 3, 4, 5 or 6;

r is 0 or 1; and s is 0 or 1.

Additional JAK inhibitors include CEP-701 (Lestaurtinib, Cephalon Technology), a JAK 2 FL3 kinase, AZD1480 (Astra Zeneca), a JAK 2 inhibitor, LY3009104/INCB28050 (Eli Lilly, Incyte), a JAK 1/2 inhibitor, Pacritinib/SB 1518 (S*BIO), a JAK 2 inhibitor, VX-509 (Vertex), a JAK 3 inhibitor, GLPG0634 (Galapagos), a JAK 1 inhibitor, INC424 (Novartis), a JAK inhibitor, R-348 (Rigel), a JAK 3 inhibitor, CYT387 (YM Bioscience), a JAK1/2 inhibitor, TG 10138, a JAK 2 inhibitor, AEG 3482 (Axon), a JAK inhibitor, and pharmaceutically-acceptable salts and prodrugs thereof.

Lestaurtinib has the following formula:

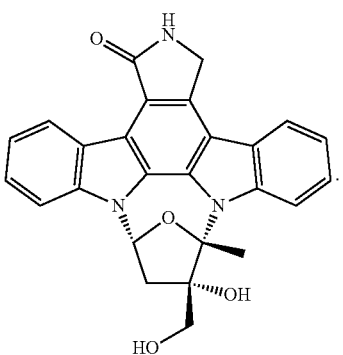 [SMILES: C[C@]12O[C@H](C[C@]1(O)CO)n1c3ccccc3c3c4c(c5c6ccccc6n2c5c31)CNC4=O]

AEG 3482 has the following formula:

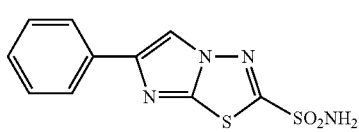 [SMILES: NS(=O)(=O)c1nn2cc(-c3ccccc3)nc2s1]

TG 10138 has the following formula:

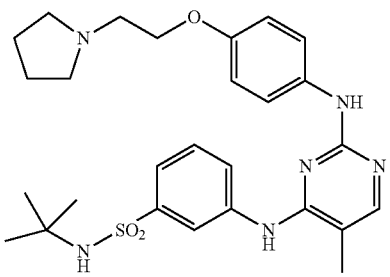 [SMILES: Cc1cnc(Nc2ccc(OCCN3CCCC3)cc2)nc1Nc1cccc(S(=O)(=O)NC(C)(C)C)c1]

CYT387 has the following formula:

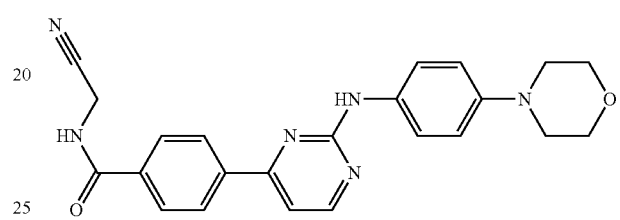

AZD 1480 has the following formula:

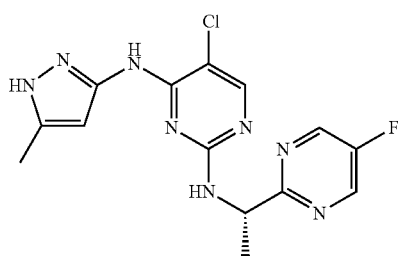 [SMILES: Cc1cc(Nc2nc(N[C@@H](C)c3ncc(F)cn3)ncc2Cl)n[nH]1]

LY3009104 is believed to be (R)-3-(4-(7H-pyrrolo[2,3-d]pyrimidin-4-yl)-1H-pyrazol-1-yl-3-cyclopentyl-propanenitrile Pacritinib has the following formula:

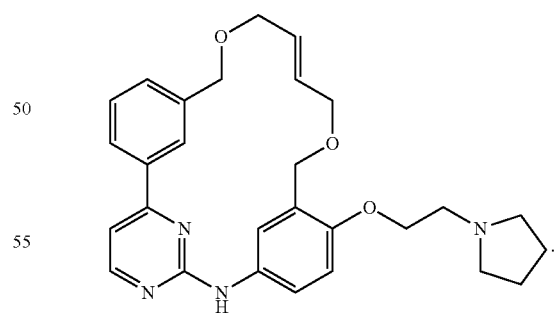

The compounds include those described in U.S. Publication Nos. 20110020469; 20110118255; 20100311743; 20100310675; 20100280026; 20100160287; 20100081657; 20100081645; 20090181938; 20080032963; 20070259869; and 20070249031.

The compounds also include those described in U.S. Publication Nos. 20110251215; 20110224157; 20110223210; 20110207754; 20110136781; 20110086835; 20110086810; 20110082159; 20100190804; 20100022522;

20090318405; 20090286778; 20090233903; 20090215766; 20090197869; 20090181959; 20080312259; 20080312258; 20080188500; and 20080167287; 20080039457.

The compounds also include those described in U.S. Publication Nos. 20100311693; 20080021013; 20060128780; 20040186157; and 20030162775.

The compounds also include those described in U.S. Publication Nos. 20110245256; 20100009978; 20090098137; and 20080261973.

The compounds also include those described in U.S. Publication No. 20110092499. Representative compounds include:
1. 7-iodo-N-(4-morpholinophenyl)thieno[3,2-d]pyrimidin-2-amine 2. 7-(4-aminophenyl)-N-(4-morpholinophenyl) thieno[3,2-d]pyrimidin-2-amine 3. N-(4-(2-(4-morpholinophenylamino)thieno[3,2-d]pyrimidin-7-yl)phenyl)acrylamide 4. 7-(3-aminophenyl)-N-(4-morpholinophenyl)thieno [3,2-d]pyrimidin-2-amine 5. N-(3-(2-(4-morpholinophenylamino)thieno[3,2-d]pyrimidin-7-yl)phenyl)acrylamide 7. N-(4-morpholinophenyl)thieno[3,2-d] pyrimidin-2-amine 8. methyl 2-(4-morpholinophenylamino) thieno[3,2-d]pyrimidine-7-carboxylate 9. N-(4-morpholinophenyl)-5H-pyrrolo[3,2-d]pyrimidin-2-amine 10. 7-(4-amino-3-methoxyphenyl)-N-(4-morpholinophenyl) thieno[3,2-d]pyrimidin-2-amine 11. 4-(2-(4-morpholinophenylamino)thieno[3,2-d]pyrimidin-7-yl)benzenesulfonam-ide 12. N,N-dimethyl-3-(2-(4-morpholinophenylamino)thieno[3,2-d]pyrimidin-7-yl) benzenesulfonamide 13. 1-ethyl-3-(2-methoxy-4-(2-(4-morpholinophenylamino)thieno[3,2-d]pyrimidin-7-yl) phenyl)urea 14. N-(4-(2-(4-morpholinophenylamino)thieno [3,2-d]pyrimidin-7-yl)phenyl)metha-nesulfonamide 15. 2-methoxy-4-(2-(4-morpholinophenylamino)thieno[3,2-d] pyrimidin-7-yl)pheno-l 16. 2-cyano-N-(3-(2-(4-morpholinophenylamino)thieno[3,2-d]pyrimidin-7-yl-)phenyl) acetamide 17. N-(cyanomethyl)-2-(4-morpholinophenylamino)thieno[3,2-d]pyrimidine-7-carb-oxamide 18. N-(3-(2-(4-morpholinophenylamino)thieno[3,2-d]pyrimidin-7-yl)phenyl)metha-nesulfonamide 19. 1-ethyl-3-(4-(2-(4-morpholinophenylamino)thieno[3,2-d]pyrimidin-7-yl)-2-(-trifluoromethoxy)phenyl)urea 20. N-(3-nitrophenyl)-7-phenylthieno[3,2-d]pyrimidin-2-amine 21. 7-iodo-N-(3-nitrophenyl)thieno[3,2-d]pyrimidin-2-amine 22. N1-(7-(2-ethylphenyl)thieno[3,2-d]pyrimidin-2-yl)benzene-1,3-diamine 25. N-tert-butyl-3-(2-(4-morpholinophenylamino) thieno[3,2-d]pyrimidin-7-yl)be-nzenesulfonamide 26. N1-(7-iodothieno[3,2-d]pyrimidin-2-yl) benzene-1,3-diamine 28. 7-(4-amino-3-(tri fluoromethoxy)phenyl)-N-(4-morpholinophenyl)thieno[3,2-d]pyrimidin-2-amin-e 29. 7-(2-ethylphenyl)-N-(4-morpholinophenyl)thieno[3,2-d]pyrimidin-2-ami-ne 30. N-(3-(2-(4-morpholinophenylamino) thieno[3,2-d]pyrimidin-7-yl)phenyl-)acetamide 31. N-(cyano methyl)-N-(3-(2-(4-morpholinophenylamino) thieno[3,2-d]pyrimidin-7-yl)phenyl)methanesulfonamide 32. N-(cyanomethyl)-N-(4-(2-(4-morpholinophenylamino) thieno[3,2-d]pyrimidin-7-yl)phenyl)methanesulfonamide 33. N-(3-(5-methyl-2-(4-morpholinophenylamino)-5H-pyrrolo[3,2-d]pyrimidin-7-y-l)phenyl)methanesulfonamide 34. 4-(5-methyl-2-(4-morpholinophenylamino)-5H-pyrrolo[3, 2-d]pyrimidin-7-yl)b-enzenesulfonamide 36. N-(4-(5-methyl-2-(4-morpholinophenylamino)-5H-pyrrolo[3,2-d] pyrimidin-7-y-l)phenyl)methanesulfonamide 37. 7-iodo-N-(4-morpholinophenyl)-5H-pyrrolo[3,2-d]pyrimidin-2-amine 38. 7-(2-isopropylphenyl)-N-(4-morpholinophenyl) thieno[3,2-d]pyrimidin-2-amin-e 39. 7-bromo-N-(4-morpholinophenyl)thieno[3,2-d]pyrimidin-2-amine 40. N7-(2-isopropylphenyl)-N2-(4-morpholinophenyl)thieno[3,2-d]pyrimidine-2,7-diamine 41. N7-(4-isopropylphenyl)-N2-(4-morpholinophenyl)thieno[3,2-d]pyrimidine-2,7-diamine 42. 7-(5-amino-2-methylphenyl)-N-(4-morpholinophenyl) thieno[3,2-d]pyrimidin-2-amine 43. N-(cyanomethyl)-4-(2-(4-morpholinophenylamino)thieno[3,2-d]pyri-midin-7-yl) benzamide 44. 7-iodo-N-(3-morpholinophenyl)thieno[3,2-d]pyrimidin-2-amine 45. 7-(4-amino-3-nitrophenyl)-N-(4-morpholinophenyl)thieno[3,2-d]pyrimidin-2-amine 46. 7-(2-methoxypyridin-3-yl)-N-(4-morpholinophenyl)thieno [3,2-d]pyr-imidin-2-amine 47. (3-(7-iodothieno[3,2-d]pyrimidin-2-ylamino)phenyl)methanol 48. N-tert-butyl-3-(2-(3-morpholinophenylamino)thieno[3,2-d]pyrimidin-7-yl) be-nzenesulfonamide 49. N-tert-butyl-3-(2-(3-(hydroxymethyl)phenylamino)thieno[3,2-d]pyrimidin-7-yl) benzenesulfonamide 50. N-(4-morpholinophenyl)-7-(4-nitrophenylthio)-5H-pyrrolo[3,2-d]pyrimidin-2-amine 51. N-tert-butyl-3-(2-(3,4,5-trimethoxyphenylamino)thieno[3, 2-d]pyr-imidin-7-yl) benzene sulfonamidc 52. 7-(4-amino-3-nitrophenyl)-N-(3,4-dimethoxyphenyl)thieno[3,2-d]py-rimidin-2-amine 53. N-(3,4-dimethoxyphenyl)-7-(2-methoxypyridin-3-yl)thieno[3,2-d]p-yrimidin-2-amine 54. N-tert-butyl-3-(2-(3,4-dimethoxyphenylamino)thieno[3,2-d]pyrimidin-7-yl)b-enzenesulfonamide 55. 7-(2-aminopyrimidin-5-yl)-N-(3,4-dimethoxyphenyl)thieno[3,2-d]py-rimidin-2-amine 56. N-(3,4-dimethoxyphenyl)-7-(2,6-dimethoxypyridin-3-yl)thieno[3,2-d]pyrimidin-2-amine 57. N-(3,4-dimethoxyphenyl)-7-(2,4-dimethoxypyrimidin-5-yl) thieno[3,2-d]pyrim-idin-2-amine 58. 7-iodo-N-(4-(morpholinomethyl)phenyl)thieno[3,2-d]pyrimidin-2-amine 59. N-tert-butyl-3-(2-(4-(morpholinomethyl)phenylamino) thieno[3,2-d]pyrimidin-7-yl)benzenesulfonamide 60. 2-cyano-N-(4-methyl-3-(2-(4-morpholinophenylamino) thieno[3,2-d]pyrimidin-7-yl)phenyl)acetamide 61. ethyl 3-(2-(4-morpholinophenylamino)thieno[3,2-d]pyrimidin-7-yl)benzoate 62. 7-bromo-N-(4-(2-(pyrrolidin-1-yl)ethoxy) phenyl)thieno[3,2-d]pyrimidin-2-a-mine 63. N-(3-(2-(4-(2-(pyrrolidin-1-yl)ethoxy)phenylamino)thieno[3,2-d]py-rimidin-7-yl)phenyl)acetamide 64. N-(cyanomethyl)-3-(2-(4-morpholinophenylamino)thieno[3,2-d]pyrimidin-7-yl-) benzamide 65. N-tert-butyl-3-(2-(4-morpholinophenylamino)thieno[3,2-d]pyrimidin-7-yl)be-nzamide 66. N-tert-butyl-3-(2-(4-(1-ethylpiperidin-4-yloxy) phenylamino)thieno[3,2-d]p-yrimidin-7-yl) benzenesulfonamide 67. tert-butyl 4-(2-(4-(morpholinomethyl)phenylamino)thieno[3,2-d]pyrimidin-7-yl)-1H-pyr-azole-1-carboxylate 68. 7-bromo-N-(4-((4-ethylpiperazin-1-yl)methyl)phenyl)thieno[3,2-d]pyrimidin-2-amine 69. N-tert-butyl-3-(2-(4-((4-ethylpiperazin-1-yl) methyl)phenylamino)thieno[3,-2-d]pyrimidin-7-yl) benzenesulfonamide 70. N-(4-((4-ethylpiperazin-1-yl) methyl)phenyl)-7-(1H-pyrazol-4-yl)thieno[3,2-d] pyrimidin-2-amine 71. N-(cyanomethyl)-3-(2-(4-(morpholino methyl)phenylamino)thieno[3,2-d]pyrimi-din-7-yl)benzamide 72. N-tert-butyl-3-(2-(4-(2-(pyrrolidin-1-yl) ethoxy)phenylamino)thieno[3,2-d]-pyrimidin-7-yl) benzenesulfonamide 73. tert-butyl pyrrolidin-1-yl)ethoxy) phenylamino)thieno[3,2-d]pyrimidin-7-yl)benzylcarbamate 74. 3-(2-(4-(2-(pyrrolidin-1-yl)ethoxy)phenylamino)thieno [3,2-d]pyri-midin-7-yl) benzene sulfonamide 75. 7-(3-chloro-4-fluorophenyl)-N-(4-(2-(pyrrolidin-1-yl)ethoxy) phenyl)thieno-[3,2-d]pyrimidin-2-amine 76. tert-butyl 4-(2-(4-(1-ethylpiperidin-4-yloxy)phenylamino)thieno[3,2-d] pyrimidin-7-yl-)-1H-pyrazole-1-carboxylate 77. 7-(benzo [d][1,3]dioxol-5-yl)-N-(4-(morpholinomethyl)phenyl) thieno[3,2-d]p-yrimidin-2-amine 78. tert-butyl 5-(2-(4-(morpholinomethyl)phenylamino)thieno[3,2-d]pyrimidin-7-yl)-1H-ind-ole-1-carboxylate 79. 7-(2-aminopyrimidin-5- yl)-N-(4-(morpholinomethyl)phenyl)thieno[3,2-d]pyri-midin-2-amine 80. tert-butyl 4-(2-(4-(morpholinomethyl) phenylamino)thieno[3,2-d]pyrimidin-7-yl)-5,6-dihydropyridine-1 (2H)-carboxylate 81. tert-butyl morpholinomethyl)phenylamino)thieno[3,2-d]pyrimidin-7-yl)benzylcarbamate 82. N-(3-(2-(4-(morpholinomethyl)phenylamino)thieno[3,2-d]pyrimidin-7-yl)-phenyl)acetamide 83. N-(4-(2-(4-(morpholinomethyl)phenylamino)thieno[3,2-d]pyrimidin-7-yl)phen-yl)acetamide 84. N-(3-(2-(4-(morpholinomethyl)phenylamino)thieno[3,2-d]pyrimidin-7-yl) phen-yl)methanesulfonamide 85. 7-(4-(4-methylpiperazin-1-yl)phenyl)-N-(4-(morpholinomethyl)phenyl)thieno-[3,2-d]pyrimidin-2-amine 86. N-(2-methoxy-4-(2-(4-(morpholino meth yl)phenylamino)thieno[3,2-d]pyrimidin-7-yl)phenyl)acetamide 87. 7-bromo-N-(3,4,5-trimethoxyphenyl)thieno[3,2-d]pyrimidin-2-amine 88. (3-(2-(3,4,5-trimethoxyphenylamino)thieno[3,2-d]pyrimidin-7-yl)phenyl)met-hanol 89. (4-(2-(3,4,5-trimethoxyphenylamino)thieno[3,2-d]pyrimidin-7-yl)p-henyl)methanol 90. (3-(2-(4-morphoinophenylamino)thieno [3,2-d]pyrimidin-7-yl)phenyl)methano-l 91. (4-(2-(4-morpholinophenylamino)thieno[3,2-d]pyrimidin-7-yl) phenyl)me-thanol 92. N-(pyrrolidin-1-yl)ethoxy) phenylamino)thieno[3,2-d]pyrimidin-7-yl)benzyl) methanesulfonamide 93. tert-butyl morpholinomethyl) phenylamino)thieno[3,2-d]pyrimidin-7-yl)benzylcarbamate 94. N-(4-(morpholinomethyl)phenyl)-7-(3-(piperazin-1-yl) phenyl)thieno[3,2-d]pyrimidin-2-amine 95. 7-(6-(2-morpholinoethylamino)pyridin-3-yl)-N-(3,4,5-trimethoxyphenyl)thie-no[3,2-d]pyrimidin-2-amine 96. 7-(2-ethylphenyl)-N-(4-(2-(pyrrolidin-1-yl)ethoxy)phenyl)thieno[3,2-d]pyrimidin-2-amine 97. 7-(4-(aminomethyl)phenyl)-N-(4-(morpholinomethyl)phenyl)thieno[3,2-d]pyri-midin-2-amine 98. N-(4-(1-ethylpiperidin-4-yloxy)phenyl)-7-(1H-pyrazol-4-yl)thieno[3,2-d]py-rimidin-2-amine 99. N-(2,4-dimethoxyphenyl)-7-phenylthieno[3,2-d]pyrimidin-2-amine 100. 7-bromo-N-(3,4-dimethoxyphenyl)thieno[3,2-d] pyrimidin-2-amine 101. N-(3,4-dimethoxyphenyl)-7-phenylthieno[3,2-d]pyrimidin-2-amine R348 (Rigel) is defined in Velotta et al., "A novel JAK3 inhibitor, R348, attenuates chronic airway allograft rejection," Transplantation. 2009 Mar. 15; 87(5):653-9.

The present invention also relates to the use of pharmaceutically acceptable acid addition salts of compounds of Formulas A and B, as well as the additional JAK inhibitors described herein. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonatc, p-toluenesulfonate and pamoate [i.e., 1,1'-methylene-his-(2-hydroxy-3-naphthoate)]salts.

The invention also relates to the use of base addition salts of Formulas A and B. The chemical bases that may be used as reagents to prepare pharmaceutically acceptable base salts of those compounds of Formulas A and B that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The JAK inhibitors described herein include all conformational isomers (e.g., cis and trans isomers. Those compounds which have asymmetric centers exist in different enantiomeric and diastereomeric forms. This invention relates to the use of all optical isomers and stereoisomers of the compounds, and mixtures thereof, and to all pharmaceutical compositions and methods of treatment that may employ or contain them. In this regard, the invention includes both the E and Z configurations. The compounds of Formulas A and B can also exist as tautomers. This invention relates to the use of all such tautomers and mixtures thereof.

This invention also encompasses pharmaceutical compositions containing prodrugs of compounds of the Formulas A and B. This invention also encompasses methods of treating or preventing viral infections that can be treated or prevented by inhibitors of protein kinases, such as the enzyme Janus Kinase 1, 2, or 3 comprising administering prodrugs of compounds of the Formulas A and B. Compounds of Formulas A and B having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of Formulas A and B. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of Formulas A and B through the carbonyl carbon prodrug sidechain.

The JAK inhibitors can be used in combination with additional anti-retroviral agents, including reverse transcriptase inhibitors, such as nucleoside reverse transcriptase inhibitors (NRTI) and non-nucleoside reverse transcriptase inhibitors (NNRTI), non-nucleoside viral polymerase inhibitors, protease inhibitors, fusion inhibitors, entry inhibitors, attachment inhibitors, and integrase inhibitors such as raltegravir (Isentress) or MK-0518, GS-9137 (Elvitegravir, Gilead Sciences), GS-8374 (Gilead Sciences), or GSK-364735.

In one embodiment, the combinations include, in addition to a JAK inhibitor as described herein, at least one adenine nucleoside antiviral agent, at least one cytosine nucleoside antiviral agent, at least one guanine nucleoside antiviral agent, and at least one thymidine nucleoside antiviral agent. In one aspect of this embodiment, the therapeutic combinations include, and further include at least one additional agent selected from reverse transcriptase inhibitors, especially non-nucleoside viral polymerase inhibitors, protease inhibitors, fusion inhibitors, entry inhibitors, attachment inhibitors, and integrase inhibitors such as raltegravir (Isentress) or MK-0518, GS-9137 (elvitegravir, Gilead Sciences), GS-8374 (Gilead Sciences), or GSK-364735.

Certain JAK inhibitors are also inhibitors of CYP3A4, which means that they will significantly increase the $C_{max}$ plasma level of any anti-HIV drug that binds to CYP3A4, including HIV-1 protease inhibitors.

It is believed that this therapy, particularly when administered at an early stage in the development of HIV-1 infection, has the possibility of eliminating HIV-1 infection in a patient. While not wishing to be bound to a particular theory, it is believed that the JAK inhibitors function in a way that is not likely to provoke resistance (i.e., does not involve inhibition of enzymes, or introduction of modified bases in a way that would provoke enzyme mutations).

Further, when the JAK inhibitors are combined with different nucleosides containing all the possible bases (ACTG), optionally in the presence of additional agents, the combination minimizes the ability of the virus to adapt its reverse transcriptase and develop resistance to any class of nucleoside antiviral nucleosides (i.e., adenine, cytosine, thymidine, or guanine), because it would be susceptible to at least one of the other nucleoside antiviral agents that are present, and/or the additional non-NRTI therapeutic agent. Furthermore, hitting the same target such as the active site of the HIV-1 polymerase with different bases allows complete and thorough chain termination of all the possible growing viral DNA chains. The use of an NNRTI in addition to the four different nucleosides (ACTG analogs) can be even more effective, since NNRTI bind to the HIV-polymerase and cause the enzyme to change conformation preventing chain elongation by natural nucleosides interacting in the active site of the enzyme.

In any of these embodiments, additional therapeutic agents can be used in combination with these agents, particularly including agents with a different mode of attack. Such agents include but are not limited to: antivirals, such as cytokines, e.g., rIFN alpha, rIFN beta, rIFN gamma; amphotericin B as a lipid-binding molecule with anti-HIV activity; a specific viral mutagenic agent (e.g., ribavirin), an HIV-1 VIF inhibitor, and an inhibitor of glycoprotein processing. Representative anti-TNF alpha therapies include, but are not limited to, Infliximab (Remicade), adalimumab (Humira), certolizumab pegol (Cimzia), and golimumab (Simponi), alone or with a circulating receptor fusion protein such as etanercept (Enbrel).

When administered in combination, the agents can be administered in a single or in multiple dosage forms. In some embodiments, some of the antiviral agents are orally administered, whereas other antiviral agents are administered by injection, which can occur at around the same time, or at different times.

The compounds can be used in different ways to treat or prevent HIV, and, in one embodiment, to cure an HIV infection. The invention encompasses combinations of the two types of antiviral agents, or pharmaceutically acceptable derivatives thereof, that are synergistic, i.e., better than either agent or therapy alone.

In one embodiment, a combination of a JAK inhibitor as described herein, a macrophage depleting agent (e.g., clodronate-loaded liposomes, gadolinium chloride (GdCl)), plus HAART therapy is used.

In another embodiment, a combination of a histone deacetylase inhibitor (HDAC inhibitor) or interleukin 7 (IL-7) and HAART and a JAK inhibitor is used.

In another embodiment, the JAK inhibitors are administered to a patient before, during, or after administration of a vaccine or an immunomodulatory agent.

Combinations of these approaches can also be used.

The antiviral combinations described herein provide means of treatment which can not only reduce the effective dose of the individual drugs required for antiviral activity, thereby reducing toxicity, but can also improve their absolute antiviral effect, as a result of attacking the virus through multiple mechanisms. That is, various combinations described herein are useful because their synergistic actions permit the use of less drug, and/or increase the efficacy of the drugs when used together in the same amount as when used alone.

The use of JAK inhibitors, alone or in combination, provides a means for circumventing the development of viral resistance, thereby providing the clinician with a more efficacious treatment.

The disclosed JAK inhibitors, used alone or in combination or in alternation therapies, are useful in the prevention and treatment of HIV-1 infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV. The therapy can be also used to treat other viral infections, such as HIV-2.

The invention includes methods for treating or preventing, and uses for the treatment or prophylaxis, of a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus), as well as Alphaviruses, such as the Chikungunya virus.

BRIEF DESCRIPTION OF THE FIGURES

FIG. 1 is a chart showing the potency and toxicity of JAK inhibitors Tofacitinib or Jakafi versus FDA approved controls AZT and 3TC in acutely infected resting macrophages (MO), as well as in peripheral blood mononuclear (PBM) cells. Median effective antiviral concentration ($EC_{50}$) data (potency) is shown in terms of μM concentration of the compounds. The $IC_{50}$ values (toxicity) (μM) are also shown in PBM, Mø cells, CEM cells, and Vero cells.

FIG. 2 is a chart showing the effect of various concentrations of Tofacitinib and Jakafi on cellular proliferation [total cell number ($10^6$ cells) versus NM drug] in activated PBM cells incubated for 5 days with the compounds. Cycloheximide is shown as a positive control, and a "cells plus media" control for each compound is also shown.

FIG. 3 is a chart showing the effect of various concentrations of Tofacitinib and Jakafi on cellular viability (% viability versus μM drug) in activated PBM cells incubated for 5 days with the compounds. Cycloheximide is shown as a positive control, and a "cells plus media" control for each compound is shown as well.

FIGS. 4*a-f* show the results of flow cytometric analysis of PHA+IL-2 stimulated primary human lymphocytes exposed to various concentrations of Jakafi or Tofacitinib for 5 days prior to assessment of viability using propidium iodide (flow cytometry). Histograms and scatter plots are representative data from at least 3 independent experiments conducted with pooled cells from 8 donors.

FIG. 4*a* is a scatter plot showing a Side Scatter (SSC) Gating strategy, where the X-axis in the first chart is Side Scatter Pulse Height (SSC-h) and the Y-axis is Side Scatter Pulse Width (SSC-w), and in the second chart, the forward-scattered light (FSC) is shown with the X axis being Forward Scatter Pulse Height (FSC-H) and the Y axis being Forward Scatter Pulse Width (FSC-W) and Gating strategy based on forward scatter (FSC) and side scatter (SSC) was established and used uniformly across all samples (A).

FIG. 4b is a histogram showing the results of flow cytometry studies using Propidium Iodide stain, which is read by the phycoerythrin (PE-A) channel, looking at the cell counts of viable cells. Propidium iodide is a large molecule, which exclusively intercalates into the DNA of dead/dying cells and is detectable by PE fluorescence (flow cytometry). Living cells do not uptake Propidium Iodide, therefore they are not fluorescent or detectable by the PE channel. Cells incubated in the absence of drug were 92.8% viable (therefore 92.8% of these cells did not uptake the Propidium Iodide stain), and cells exposed to 95° C. heat for 1 minute (positive control for dead cells) were 2.8% viable (therefore only 2.8% of cells were negative for Propidium Iodide stain, whereas 97.2% were dead, and therefore positive for Propidium Iodide stain) (B). The data is shown in terms of total percent of cells in each sample, where gating was established based on viable cells cultured in the absence of drug.

Figure 6A:
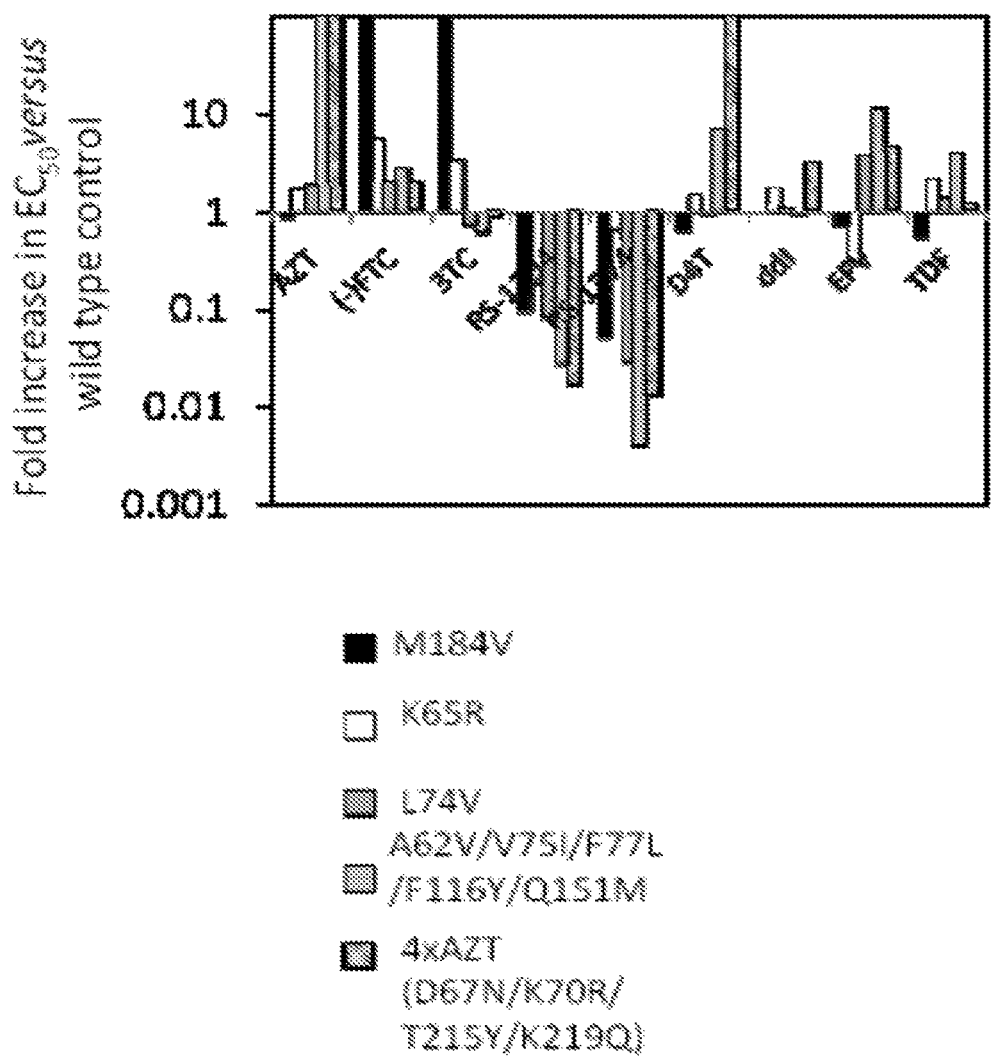
Figure 6B:
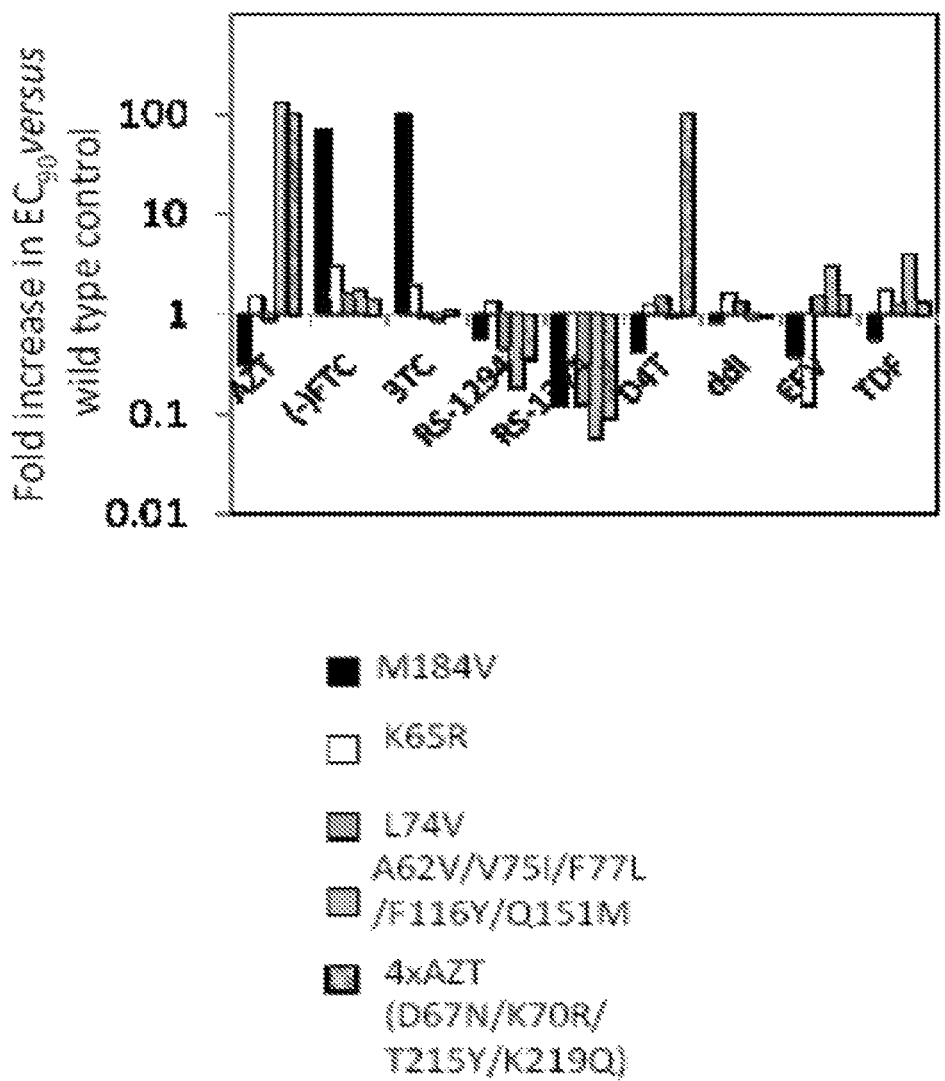

FIGS. 6a and 6b are charts showing the fold increase 50 ($FI_{50}$) and fold increase 90 ($FI_{90}$) for Jakafi and Tofacitinib against various NRTI-resistant HIV-1 in primary human lymphocytes. Results with NRTI AZT, (−) FTC, 3TC, D4T, ddI, EFV, and TDF are also shown.

Figure 7A:
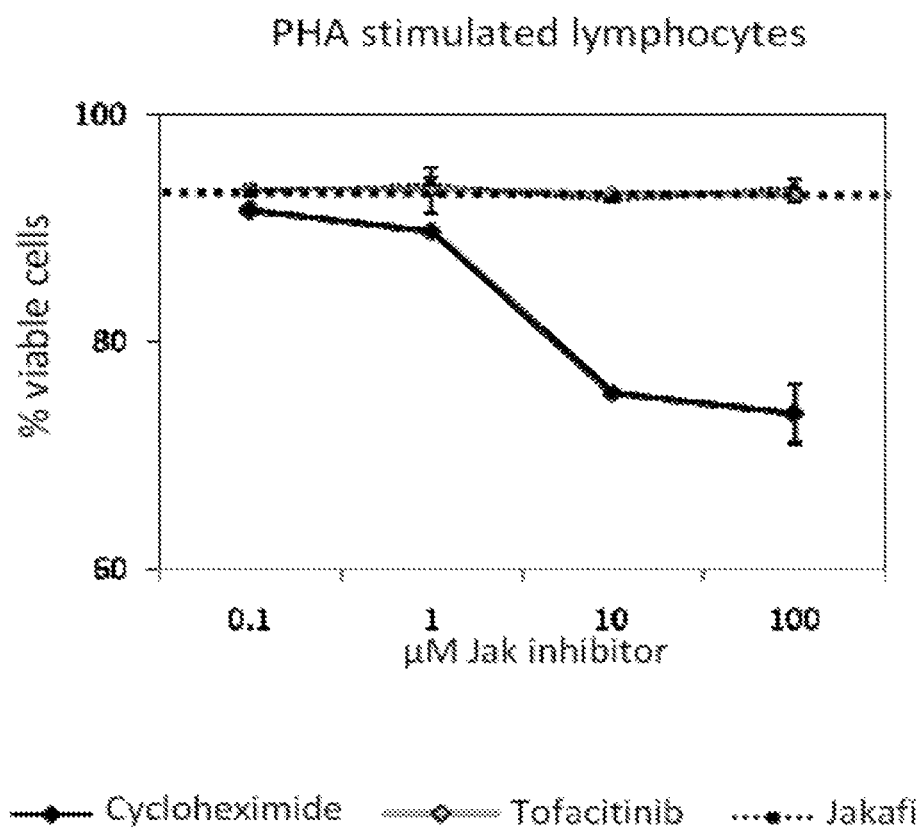
Figure 7B:
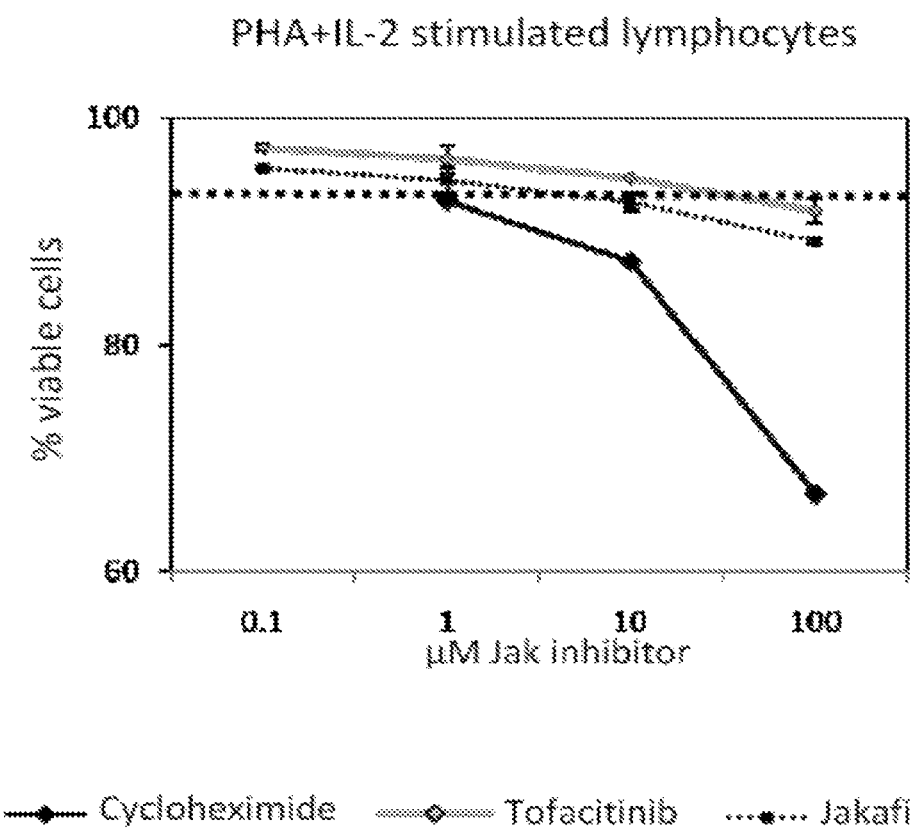
Figure 7C:
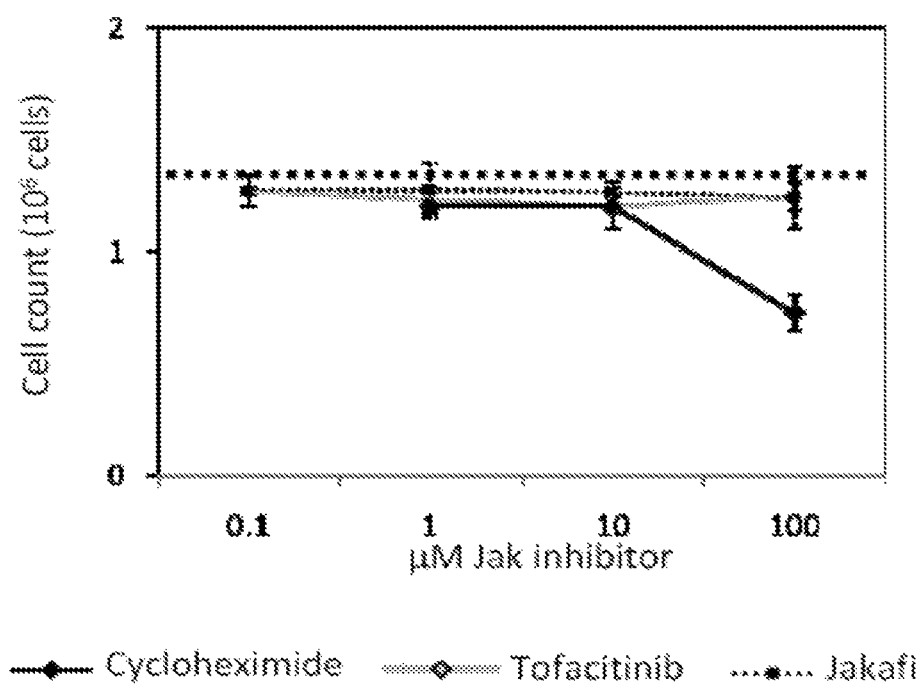
Figure 7D:
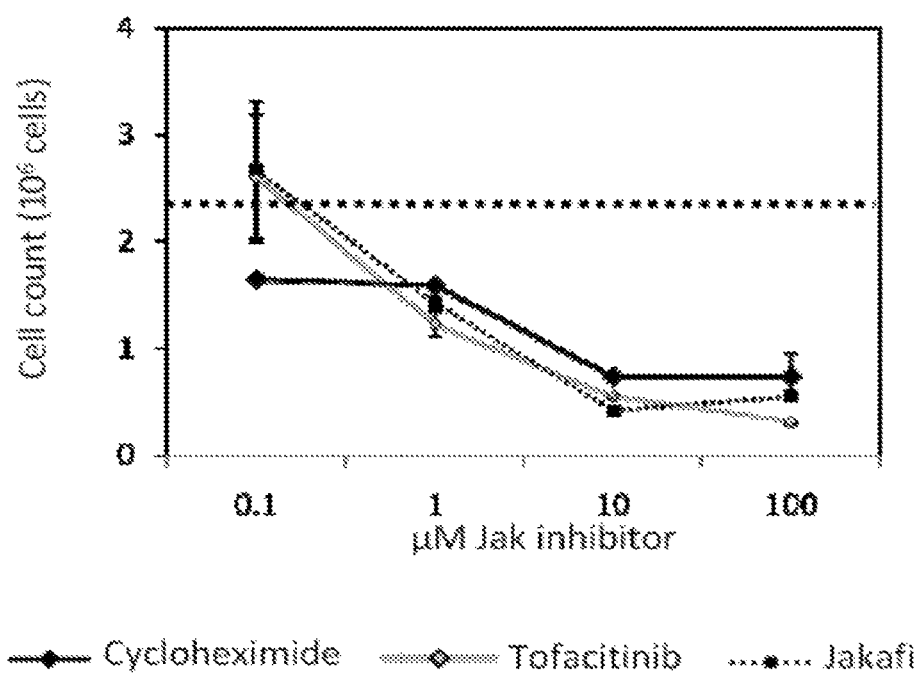

FIGS. 7a-7d are charts showing the effect of various Jak inhibitors (Cycloheximide (black line), Tofacitinib (grey line), and Jakafi (dashed line) on proliferation and viability of PHA (FIGS. 7a and 7c) or PHA+IL-2 (FIGS. 7b and 7d) stimulated primary human lymphocytes. FIGS. 7a and 7b are shown in terms of % viable cells versus concentration of Jak inhibitor (μM). FIGS. 7c and 7d are shown in terms of cell count ($10^6$ cells) versus concentration of Jak inhibitor (μM).

Figure 8A:
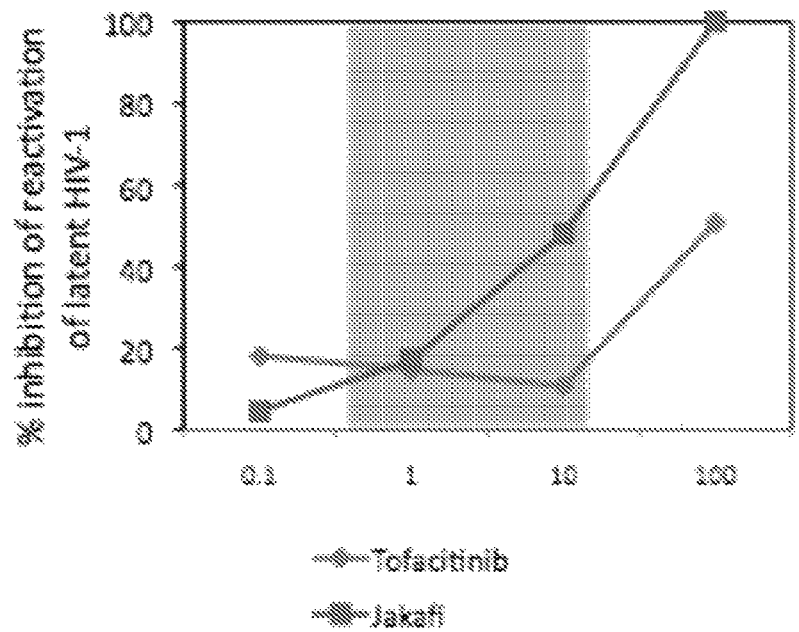
Figure 8B:
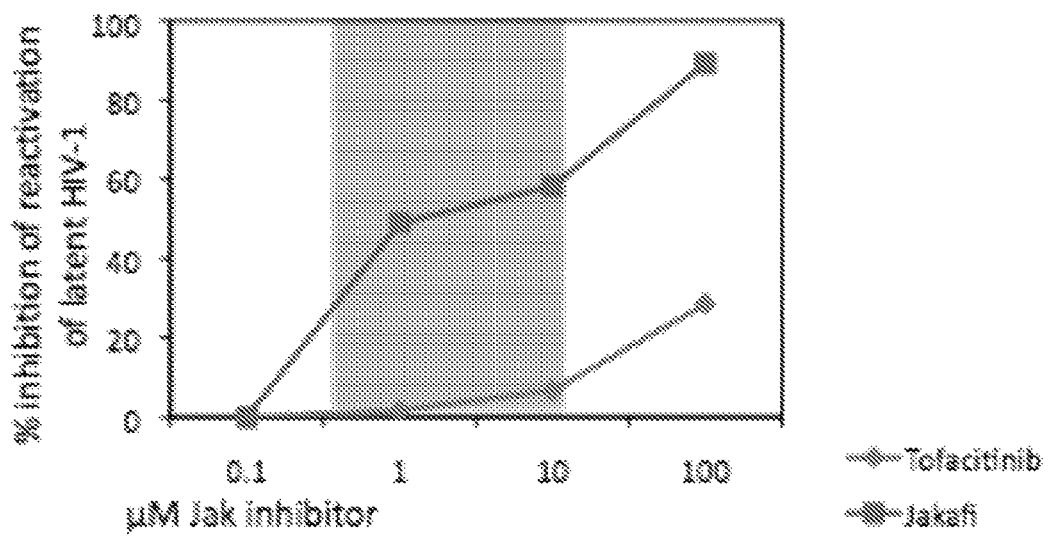

FIGS. 8a and 8b are charts showing that Tofacitinib and Jakafi inhibit reactivation of latent HIV-1. FIG. 8a shows the results in a primary central memory-based T cell latency model (Bosque and Planelles (2009) Induction of HIV-1 latency and reactivation in primary memory CD4+ T cells. Blood 113: 58-65), in terms of the % inhibition of reactivation of latent HIV-1 versus concentration of Jak inhibitor (μM). FIG. 8b shows the results in a J-Lat latency T cell system (Jordan et al, (2003) HIV reproducibly establishes a latent infection after acute infection of T cells in vitro. The EMBO Journal, Vol. 22 No. 8 pp. 1868±1877), in terms of the % inhibition of reactivation of latent HIV-1 versus concentration of Jak inhibitor (μM). Diamonds represent results for Tofacitinib, and squares represent results for Jakafi.

Figure 9A:
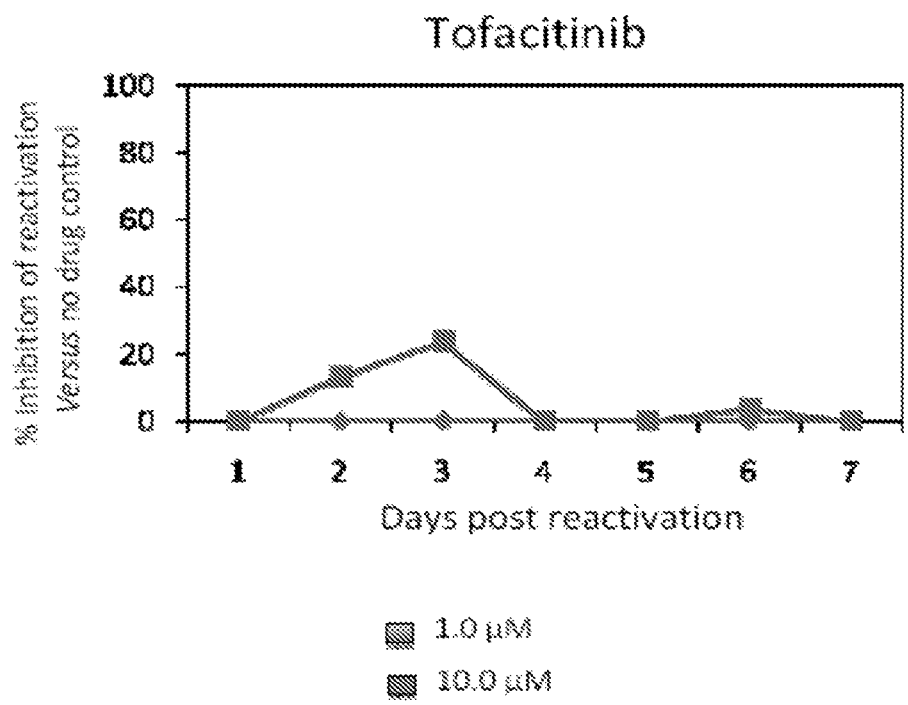
Figure 9B:
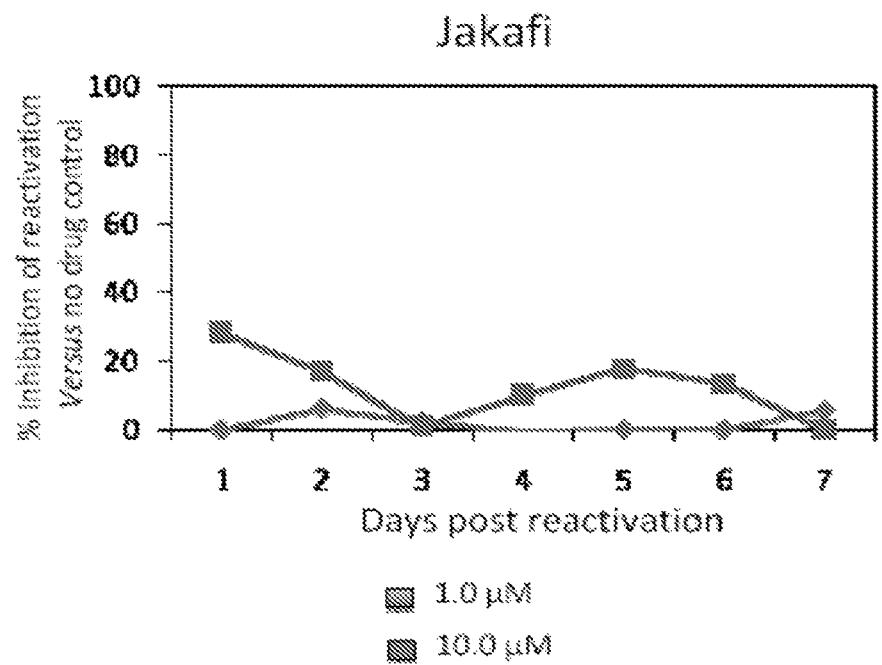

FIGS. 9a and 9b are charts showing that Tofacitinib and Jakafi inhibit reactivation of latent HIV-1 in primary human macrophages. Tofacitinib (FIG. 9a) and Jakafi (FIG. 9b) inhibit reactivation of latent HIV-1 in primary human macrophages when drug is applied to cells during reactivation but removed thereafter. Tofacitinib inhibits ~40% of reactivation while Jakafi inhibits ~35% of reactivation within 72 hr post reactivation.

Figure 10A:
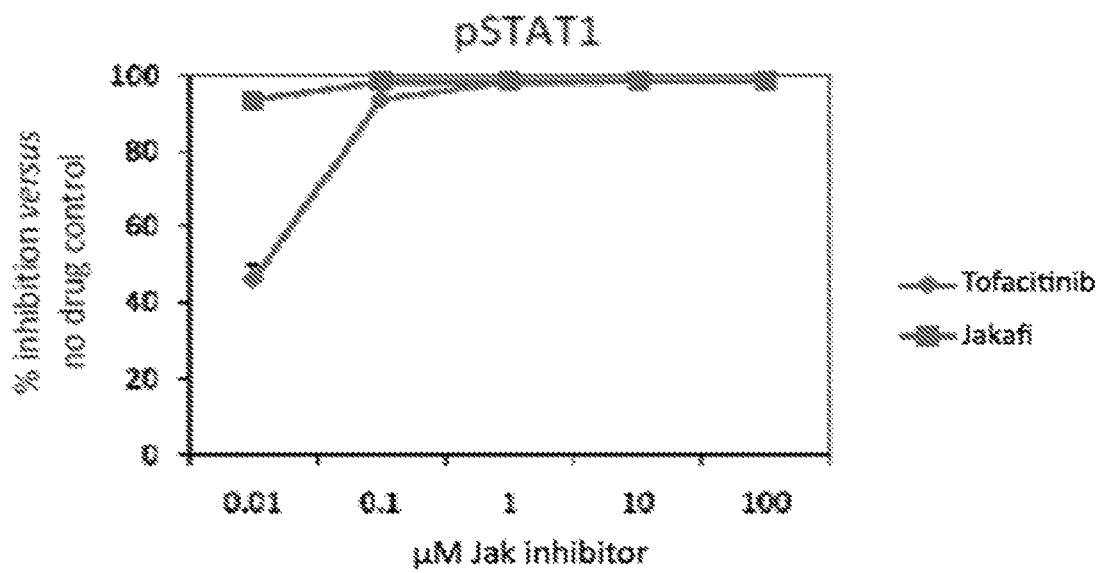
Figure 10B:
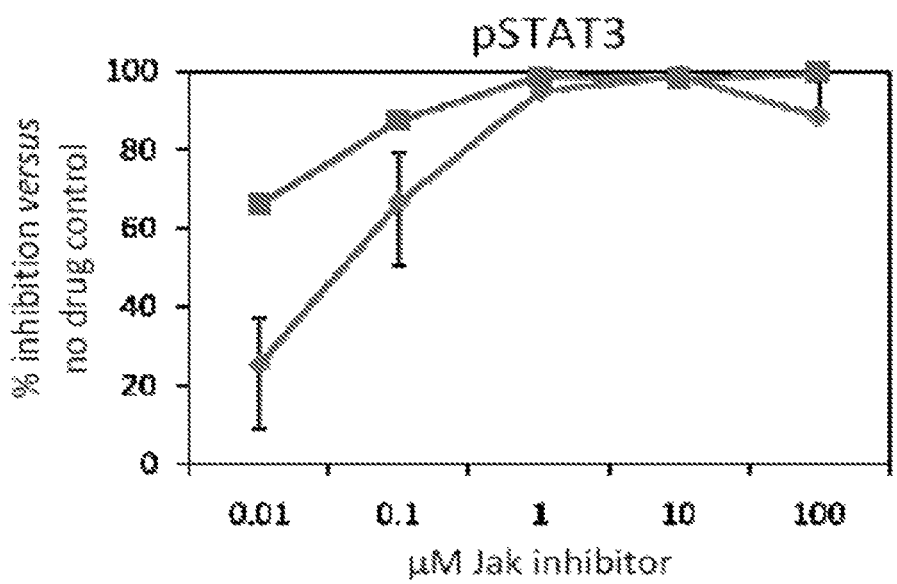
Figure 10C:
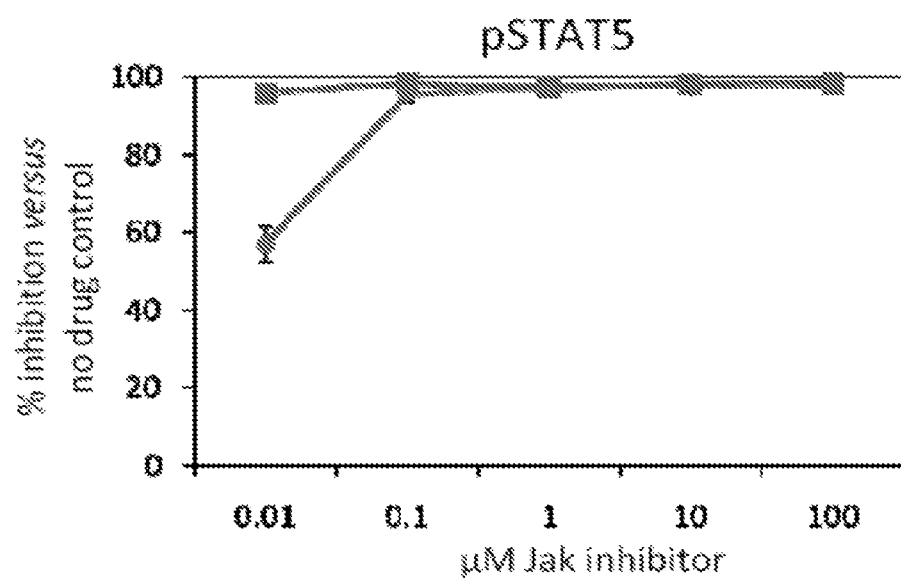

FIGS. 10a-10c are charts showing the percent inhibition of PSTAT1, PSTAT3, and PSTAT5, respectively, versus no drug (control) versus micromolar Jak inhibitor. The lines shown with diamonds represent Jak inhibitor Tofacitinib, and the lines shown with squares represent Jak inhibitor Jakafi.

FIGS. 11 A-E are graphicals showing that Jak inhibitors reduce frequency of cells harboring integrated viral DNA and IL-15-induced reactivation of latent HIV-1 in CD4 T cells. CD4 T cells were isolated from viremic donors and incubated with CD3/CD28 plus 0.01, 0.1, 1.0 or 10 μM of Jak inhibitors with or without $EC_{99}$ of ART (180 nM zidovudine, 100 nM efavirenz, 200 nM Raltegravir) (A and B). After six days, integrated viral DNA was quantified using ultra sensitive Alu PCR versus DMSO controls (n=5). 0.01 μM represents the average of all assays completed using % DMSO equivalent to Jak inhibitor concentrations. Error bars represent S.E.M. and statistical significance determined by two-way ANOVA followed by Sidak's multiple comparison post-test: *p<0.05, p<0.01, *p<0.001 and ****p<0.0001 for A and B. In panel C-E, memory $CD4^+$ T cells were isolated from ART treated aviremic donors (n=3), activated with 10 ng/ml IL-15 (panel D) or CD3/CD28 (panel E) and maintained with or without 1 μM ruxolitinib in the presence of ART. Six days post reactivation, extracellular viral RNA copies were quantified by qRT-PCR (*p<0.01, one-way ANOVA).

Figure 12:
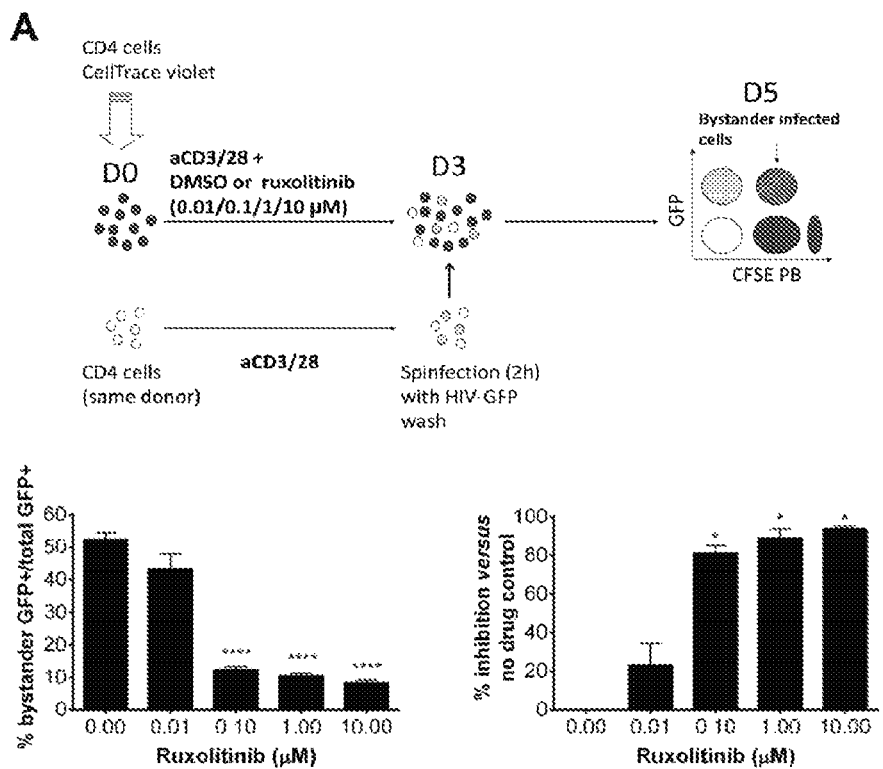

FIG. 12 are graphicals demonstrating that Jak inhibitors block bystander infection in primary CD4 T cells. Uninfected $CD4^+$ T cells were incubated with or without cell trace violet (CTV) dye. Cells with CTV dye were stimulated with CD3/CD28 and various concentrations of ruxolitinib or DMSO for 3 days (A, top). Cells without tracer violet dye were incubated with CD3/CD28 for 3 days followed by a 2 hours spinoculation with a replication competent eGFP N14-3 X4 HIV-1 (A, bottom). After spinocualtion on Day 3, both cultures (traced and untraced) were co-incubated for two days in the absence of ruxolitinib. Ruxolitinib inhibits bystander infection (GFP and CTV double positive) of uninfected bystander cells ($CTV^+$) in a dose dependent manner (B and C, n=3). Ruxolitinib blocks proliferation (CTV-lo) of bystander cells in a dose dependent manner with all concentrations tested (B, C). 0.0 μM represents the average of all assays completed using % DMSO equivalent to Jak inhibitor concentrations. Error bars represent mean with S.E.M or mean with standard deviation and statistical significance determined by two-way ANOVA followed by Sidak's multiple comparison post-test (****p<0.0001) or a two-tailed paired T test (*p<0.005).

Figure 13:
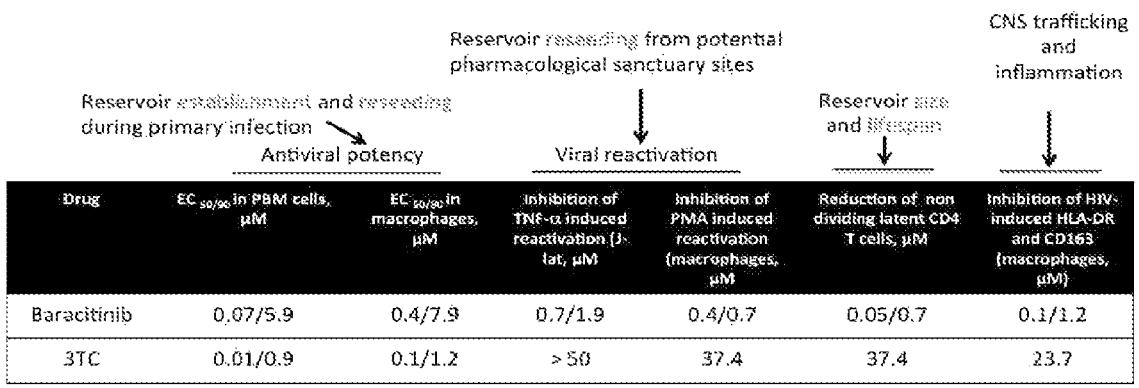

FIG. 13: Tabular summary showing that baricitinib blocks the HIV establishment, maintenance, lifespan, and HIV-induced inflammatory events (HIV-associated neurocognitive impairment system) in primary human macrophages and monocytes. Primary human macrophages or monocytes were infected with HIV-1 BaL and effect of baricitinib on antiviral potency, HIV-induced inflammation/activation, and reservoir lifespan, maintenance, and expansion was evaluated. Baricitinib blocks HIV reservoir establishment, maintenance, and expansion in primary myeloid cells, and blocks "HAND" inflammatory events that are induced by HIV in key primary CNS subsets that drive HIV-induced or HIV associated inflammatory dysfunction in the CNS (macrophages, monocytes).

DETAILED DESCRIPTION OF THE INVENTION

The present invention is directed to compounds, compositions and methods for treating viral infections, such as HIV infections, including HIV-1 and HIV-2 infections. In one embodiment, the compounds are heteroaryl substituted pyrrolo[2,3-b]pyridines and heteroaryl substituted pyrrolo[2,3-b]pyrimidines that modulate the activity of Janus kinases (JAK inhibitors).

The various embodiments of the invention are described in more detail below, and will be better understood with reference to the following non-limiting definitions.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^{1a}$, $R^{1b}$, $R^c$, and $R^{1d}$ represent substituents that can be attached to the indicated atom. A non-limiting list of R groups include, but are not limited to, hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, thiocarbonyl, O-carbamyl, N-carbamyl, O-thiocarbamyl, N-thiocarbamyl, C-amido, N-amido, S-sulfonamido, N-sulfonamide, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. An R group may be substituted or unsubstituted. If two "R" groups are covalently bonded to the same atom or to adjacent atoms, then they may be "taken together" as defined herein to form a cycloalkyl, cycloalkenyl, cycloalkynyl, aryl, heteroaryl or heteroalicyclyl group. For example, without limitation, if R' and R" of an NR'R" group are indicated to be "taken together", it means that they are covalently bonded to one another at their terminal atoms to form a ring that includes the nitrogen:

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Each of these substituents can be further substituted.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, the term "alkyl" can be straight or branched hydrocarbon chains that comprise a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group can also be a lower alkyl having 1 to 6 carbon atoms. The alkyl group of the compounds may be designated as "$C_1$-$C_6$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. By way of example only, "$C_1$-$C_6$ alkyl" indicates that there are one to six carbon atoms in the alkyl chain. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, the term "alkoxy" includes O-alkyl groups wherein "alkyl" is defined above. As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, and the like.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. Pf there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group is a $C_{6-14}$ aryl group, a $C_{6-10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, cyclic carbamates, and the like. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, A-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

An "aralkyl" is an aryl group connected, as a substituent, via a lower alkylene group. The lower alkylene and aryl group of an aralkyl may be substituted or unsubstituted. Examples include but are not limited to benzyl, substituted benzyl, 2-phenylalkyl, 3-phenylalkyl, and naphtylalkyl.

A "heteroaralkyl" is heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrolylalkyl, pyridylalkyl, isoxazolylalkyl, and imidazolylalkyl, and their substituted as well as benzo-fused analogs.

A "(heteroalicyclyl)alkyl" is a heterocyclic or a heteroalicyclylic group connected, as a substituent, via a lower alkylene group. The lower alkylene and heterocyclic or a heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group may be substituted or unsubstituted.

As used herein, "alkoxy" refers to the formula —OR wherein R is an alkyl, alkenyl, alkynyl, cycloalkyl, cycloalkenyl, cycloalkynyl, aryl, heteroaryl, heteroalicyclyl, aralkyl, or (heteroalicyclyl)alkyl is defined as above. Examples of include methoxy, ethoxy, n-propoxy, 1-methylethoxy (isopropoxy), n-butoxy, iso-butoxy, sec-butoxy, tert-butoxy, phenoxy and the like. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by hydroxy group. Examples of hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

A "sulfenyl" group refers to an "—SR" group in which R is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R is the same as defined with respect to sulfenyl. A sulfinyl may be substituted or unsubstituted.

A "sulfonyl" group refers to an "$SO_2R$" group in which R is the same as defined with respect to sulfenyl. A sulfonyl may be substituted or unsubstituted.

An "O-carboxy" group refers to a "RC(=O)O—" group in which R is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R is the same as defined with respect to O-carboxy. An ester and C-carboxy may be substituted or unsubstituted.

A "thiocarbonyl" group refers to a "—C(=S)R" group in which R is the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2RN$—" group wherein X is a halogen and R defined with respect to O-carboxy.

The term "amino" as used herein refers to a —$NH_2$ group.

As used herein, the term "hydroxy" refers to a —OH group.

A "cyan" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_1NR_AR_B$" group in which $R_A$ and $R_B$ are the same as R defined with respect to O-carboxy. An S-sulfonamido may be substituted or unsubstituted.

An "N-sulfonamido" group refers to a "$R_BSO_2N(R_A)$—" group in which $R_A$ and $R_B$ are the same as R defined with respect to O-carboxy. A N-sulfonamido may be substituted or unsubstituted.

An "O-carbamyl" group refers to a "—OC(=O)$NR_AR_B$" group in which $R_A$ and $R_B$ are the same as R defined with respect to O-carboxy. An O-carbamyl may be substituted or unsubstituted.

An "N-carbamyl" group refers to an "$R_BOC(=O)NR_A$—" group in which $R_A$ and $R_B$ are the same as R defined with respect to O-carboxy. An N-carbamyl may be substituted or unsubstituted.

An "O-thiocarbamyl" group refers to a "—OC(=S)—$NR_AR_B$" group in which $R_A$ and $R_B$ are the same as R defined with respect to O-carboxy. An O-thiocarbamyl may be substituted or unsubstituted.

An "N-thiocarbamyl" group refers to an "$R_BOC(=S)NR_A$—" group in which $R_A$ and $R_B$ are the same as R defined with respect to O-carboxy. An N-thiocarbamyl may be substituted or unsubstituted.

A "C-amido" group refers to a "—C(=O)$NR_AR_B$" group in which $R_A$ and $R_B$ are the same as R defined with respect to O-carboxy. A C-amido can be substituted or unsubstituted.

An "N-amido" group refers to a "$R_BC(=O)NR_A$—" group in which $R_A$ and $R_B$ are the same as R defined with respect to O-carboxy. An N-amido can be substituted or unsubstituted.

As used herein, "organylcarbonyl" refers to a group of the formula —C(=O)R' wherein R' can be alkyl, alkenyl, alkynyl, cycloalkyl, cycloalkenyl, cycloalkynyl, aryl, heteroaryl, heteroalicyclyl, aralkyl, or (heteroalicyclyl)alkyl. An organylcarbonyl can be substituted or unsubstituted.

The term "alkoxycarbonyl" as used herein refers to a group of the formula —C(=O)OR', wherein R' is the same as defined with respect to organylcarbonyl. An alkoxycarbonyl can be substituted or unsubstituted.

As used herein, "organylaminocarbonyl" refers to a group of the formula C(=O)NR'R" wherein R' and R" are independently selected from the same substituents as defined with respect to organylcarbonyl. An organylaminocarbonyl can be substituted or unsubstituted.

As used herein, the term "levulinoyl" refers to a —C(=O)$CH_2CH_2$C(=O)$CH_3$ group.

The term "halogen atom," as used herein, means any one of the radio-stable atoms of column 7 of the Periodic Table of the Elements, i.e., fluorine, chlorine, bromine, or iodine, with fluorine and chlorine being preferred.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the term "nucleoside" refers to a compound composed of any pentose or modified pentose moiety attached to a specific portion of a heterocyclic base, tautomer, or derivative thereof such as the 9-position of a purine, 1-position of a pyrimidine, or an equivalent position of a heterocyclic base derivative. Examples include, but are not limited to, a ribonucleoside comprising a ribose moiety and a deoxyribonucleoside comprising a deoxyribose moiety, and in some instances, the nucleoside is a nucleoside drug analog. As used herein, the term "nucleoside drug analog" refers to a compound composed of a nucleoside that has therapeutic activity, such as antiviral, antineoplastic, anti-parasitic and/or antibacterial activity.

As used herein, the term "nucleotide" refers to a nucleoside having a phosphate ester substituted on the 5'-position or an equivalent position of a nucleoside derivative.

As used herein, the term "heterocyclic base" refers to a purine, a pyrimidine and derivatives thereof. The term "purine" refers to a substituted purine, its tautomers and analogs thereof. Similarly, the term "pyrimidine" refers to a substituted pyrimidine, its tautomers and analogs thereof. Examples of purines include, but are not limited to, purine, adenine, guanine, hypoxanthine, xanthine, theobromine, caffeine, uric acid and isoguanine. Examples of pyrimidines include, but are not limited to, cytosine, thymine, uracil, and derivatives thereof. An example of an analog of a purine is 1,2,4-triazole-3-carboxamide.

Other non-limiting examples of heterocyclic bases include diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-fluorouracil, 5-bromouracil, pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases.

The term "—O-linked amino acid" refers to an amino acid that is attached to the indicated moiety via its main-chain carboxyl function group. When the amino acid is attached, the hydrogen that is part of the —OH portion of the carboxyl function group is not present and the amino acid is attached via the remaining oxygen. An —O-linked amino acid can be protected at any nitrogen group that is present on the amino acid. For example, an —O-linked amino acid can contain an amide or a carbamate group. Suitable amino acid protecting groups include, but are not limited to, carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), and tosyl (Ts) groups. The term "—N-linked amino acid" refers to an amino acid that is attached to the indicated moiety via its main-chain amino or mono-substituted amino group. When the amino acid is attached in an —N-linked amino acid, one of the hydrogens that is part of the main-chain amino or mono-substituted amino group is not present and the amino acid is attached via the nitrogen. An —N-linked amino acid can be protected at any hydroxyl or carboxyl group that is present on the amino acid. For example, an —N-linked amino acid can contain an ester or an ether group. Suitable amino acid protecting groups include, but are not limited to, methyl esters, ethyl esters, propyl esters, benzyl esters, tert-butyl esters, silyl esters, orthoesters, and oxazoline. As used herein, the term "amino acid" refers to any amino acid (both standard and non-standard amino acids), including, but limited to, α-amino acids β-amino acids, γ-amino acids and δ-amino acids. Examples of suitable amino acids, include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine.

The terms "derivative," "variant," or other similar terms refer to a compound that is an analog of the other compound.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W Greene and P. G. M. Wuts, Protective Groups in Organic Synthesis, 3. Ed. John Wiley & Sons (1999), and in J. F. W. McOmie, Protective Groups in Organic Chemistry Plenum Press (1973), both of which are hereby incorporated by reference for the limited purpose of disclosing suitable protecting groups The protecting group moiety may be chosen in such a way, that they are stable to certain reaction conditions and readily removed at a convenient stage using methodology known from the art. A non-limiting list of protecting groups include benzyl, substituted benzyl; alkylcarbonyls (e g., t-butoxycarbonyl (BOC)); arylalkylcarbonyls (e.g., benzyloxycarbonyl, benzoyl), substituted methyl ether (e.g. methoxymethyl ether); substituted ethyl ether, a substituted benzyl ether; tetrahydropyranyl ether; silyl ethers (e g, trimethylsilyl, triethylsilyl, triisopropylsilyl, t-butyldimethylsilyl, or t-butyldiphenylsilyl), esters (e.g. benzoate ester), carbonates (e g. methoxymethylcarbonate), sulfonates (e g tosylate, mesylate), acyclic ketal (e g dimethyl acetal); cyclic ketals (e.g., 1,3-dioxane or 1,3-dioxolanes); acyclic acetal; cyclic acetal, acyclic hemiacetal, cyclic hemiacetal, and cyclic dithioketals (e.g., 1,3-dithiane or 1,3-dithiolane).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction hi some embodiments, "leaving groups" are any atoms or moieties that are conjugate bases of strong acids Examples of suitable leaving groups include, but are not limited to, tosylates and halogens Non-limiting characteristics and examples of leaving groups can be found, for example in Organic Chemistry, 2d ed, Francis Carey (1992), pages 328-331, Introduction to Organic Chemistry, 2d ed., Andrew Streitwieser and Clayton Heathcock (1981), pages 169-171; and Organic Chemistry, $5^{th}$ ed., John McMurry (2000), pages 398 and 408; all of which are incorporated herein by reference for the limited purpose of disclosing characteristics and examples of leaving groups.

As used herein, the abbreviations for any protective groups, ammo acids and other compounds, are, unless indicated otherwise, in accord with their common usage, recognized abbreviations, or the IUPAC-IUB Commission on Biochemical Nomenclature (See, Biochem. 1972 11:942-944).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Examples of prodrugs include compounds that have one or more biologically labile groups attached to the parent drug (e.g., a compound of Formula I and/or a compound of Formula II). For example, one or more biologically labile groups can be attached to a functional group of the parent drug (for example, by attaching one or more biologically labile groups to a phosphate). When more than one biologically labile groups is attached, the biologically labile groups can be the same or different. The biologically labile group(s) can be linked (for example, through a covalent bond), to an oxygen or a heteroatom, such as a phosphorus of a monophosphate, diphosphate, triphosphate, and/or a stabilized phosphate analog containing carbon, nitrogen or sulfur (referred to hereinafter in the present paragraph as "phosphate"). In instances where the prodrug is form by attaching one or more biologically labile groups to the phosphate, removal of the biologically labile group in the host produces a phosphate. The removal of the biologically labile group(s) that forms the prodrug can be accomplished by a variety of methods, including, but not limited to, oxidation, reduction, amination, deamination, hydroxylation, dehydroxylation, hydrolysis, dehydrolysis, alkylation, dealkylation, acylation, deacylation, phosphorylation, dephosphorylation, hydration and/or dehydration. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might comprise a short peptide (polyaminoacid) bonded to an acid group where the peptide is metabolized or cleaved to reveal the active moiety. Additional examples of prodrug moieties include the following: R*,R*C(=O)OCH$_2$—, R*C(=O)SCH$_2$CH$_2$—, R*C(=O)SCHR'NH—, phenyl-O—, N-linked amino acids, O-linked amino acids, peptides, carbohydrates, and lipids, wherein each R is independently selected from an alkyl, an alkenyl, an alkynyl, an aryl, an aralkyl, acyl, sulfonate ester, a lipid, an —N-linked amino acid, an —O-linked amino acid, a peptide and a cholesterol. The prodrug can be a carbonate. The carbonate can be a cyclic carbonate. The cyclic carbonate can contain a carbonyl group between two hydroxyl groups that results in the formation of a five or six membered ring. Conventional procedures for the selection and preparation of suitable prodrug derivatives are described, for example, in Design of Prodrugs, (ed. H. Bundgaard, Elsevier, 1985), which is hereby incorporated herein by reference for the limited purpose of describing procedures and preparation of suitable prodrug derivatives.

The term "pro-drug ester" refers to derivatives of the compounds disclosed herein formed by the addition of any of several ester-forming groups that are hydrolyzed under physiological conditions. Examples of pro-drug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, 2-chloro-2-aminopurine, inosine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. Acyl can also include a natural or synthetic amino acid moiety.

As used herein, the term "substantially free of" or "substantially in the absence of" refers to a nucleoside composition that includes at least 95% to 98%, or more preferably, 99% to 100%, of the designated enantiomer of that nucleoside.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. Relative to abnormal cellular proliferation, the term "host" refers to unicellular or multicellular organism in which abnormal cellular proliferation can be mimicked. The term host specifically refers to cells that abnormally proliferate, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydro thiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a $sp^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a $sp^3$ hybridized nitrogen heteroatom.

$(C_6-C_{10})$aryl when used herein refers to phenyl or naphthyl.

As used herein, the term antiviral nucleoside agent refers to antiviral nucleosides that have anti-HIV activity. The agents can be active against other viral infections as well, so long as they are active against HIV.

The term "antiviral thymidine nucleosides" refers to thymidine analogues with anti-HIV activity, including but not limited to, AZT (zidovudine) and D4T (2',3'-didehydro-3'deoxythymidine (stravudine), and 1-Π-D-Dioxolane)thymine (DOT) or their prodrugs.

The term "antiviral guanine nucleosides" refers to guanine analogues with anti-HIV activity, including but not limited to, HBG [9-(4-hydroxybutyl)guanine], lobucavir ([1R(1alpha,2beta,3alpha)]-9-[2,3-bis(hydroxymethyl)cyclo butyl]guanine), abacavir ((1S,4R)-4-[2-amino-6-(cyclopropylamino)-9H-purin-9-yl]-2-cyclopentene-1-methanol sulfate (salt), a prodrug of a G-carbocyclic nucleoside) and additional antiviral guanine nucleosides disclosed in U.S. Pat. No. 5,994,321 The term "antiviral cytosine nucleosides" refers to cytosine analogues with anti-HIV activity, including but not limited to, (−)-2',3'-dideoxy-3'-thiacytidine (3TC) and its 5-fluoro analog [(−)-FTC, Emtricitabine], 2',3'-dideoxycytidine (DDC), Racivir, beta-D-2',3'-didehydro-2',3'-dideoxy-5-fluorocytidine (DFC, D-d4FC, RVT, Dexelvucitabine) and its enantiomer L-D4FC, and apricitabine (APC, AVX754, BCH-10618).

The term "antiviral adenine nucleosides" refers to adenine analogues with anti-HIV activity, including, but not limited to 2',3'-dideoxy-adenosine (ddAdo), 2',3'-dideoxyinosine (DDI), 9-(2-phosphonylmethoxyethyl)adenine (PMEA), 9-R-2-phosphonomethoxypropyl adenine (PMPA, Tenofovir) (K65R is resistant to PMPA), Tenofovir disoproxil fumarate (9-[(R)-2[[bis[[isopropoxycarbonyl)oxy]-methoxy]-phosphinyl]methoxy]propyl]adenine fumarate, TDF), bis(isopropyloxymethylcarbonyl)PMPA [bis(poc) PMPA], GS-9148 (Gilead Sciences) as well as those disclosed in Balzarini, J.; De Clercq, E. Acyclic purine nucleoside phosphonates as retrovirus inhibitors. In: Jeffries D J, De Clercq E., editors. Antiviral chemotherapy. New York, N.Y: John Wiley & Sons, Inc.; 1995. pp. 41-45, the contents of which are hereby incorporated by reference.

The term AZT is used interchangeably with the term zidovudine throughout. Similarly, abbreviated and common names for other antiviral agents are used interchangeably throughout.

As used herein, the term DAPD ((2R,4R)-2-amino-9-[(2-hydroxymethyl)-I, 3-dioxolan-4-yl]adenine) is also intended to include a related form of DAPD known as APD [(−)-β-D-2-aminopurine dioxolane], as well as all optically active forms of DAPD, including optically active forms and racemic forms and its phosphate prodrugs as well as dioxolane-G and the 6-methoxy or 6-chloro derivatives.

As used herein, the term "pharmaceutically acceptable salts" refers to pharmaceutically acceptable salts which, upon administration to the recipient, are capable of providing directly or indirectly, a nucleoside antiviral agent, or that exhibit activity themselves.

As used herein, the term "prodrug," in connection with nucleoside antiviral agents, refers to the 5' and N-acylated, alkylated, or phosphorylated (including mono, di, and triphosphate esters as well as stabilized phosphates and phospholipid) derivatives of nucleoside antiviral agents. In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably $C_{1-18}$.

As used herein, the term "resistant virus" refers to a virus that exhibits a three, and more typically, five or greater fold increase in $EC_{50}$ compared to naive virus in a constant cell line, including, but not limited to peripheral blood mononuclear (PBM) cells, or MT2 or MT4 cells.

As used herein, the term "substantially pure" or "substantially in the form of one optical isomer" refers to a composition that includes at least 95% to 98%, or more, preferably 99% to 100%, of a single enantiomer of the JAK inhibitors described herein, and, optionally, to similar concentrations of a single enantiomer of a nucleoside. In a preferred embodiment, the JAK inhibitors are administered in substantially pure form.

I. JAK Inhibitors

Representative JAK inhibitors include those disclosed in U.S. Pat. No. 7,598,257, an example of which is Ruxolitinib (Jakafi, Incyte), which has the structure shown below:

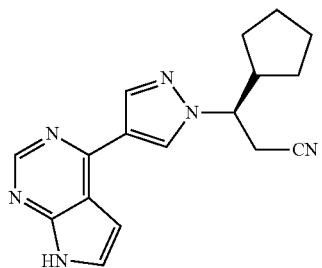 [SMILES: N#CC[C@H](C1CCCC1)n1cc(-c2ncnc3[nH]ccc23)cn1]

Representative JAK inhibitors also include those disclosed in U.S. Pat. Nos. Re 41,783; 7,842,699; 7,803,805; 7,687,507; 7,601,727; 7,569,569; 7,192,963; 7,091,208; 6,890,929, 6,696,567; 6,962,993; 6,635,762; 6,627,754; and 6,610,847, an example of which is Tofacitinib, which has the structure shown below:

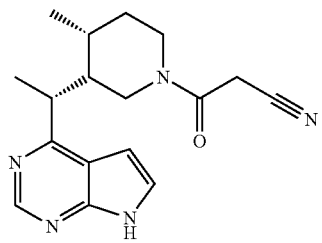 [SMILES: C[C@@H]1CCN(C(=O)CC#N)CC1[C@@H](C)c1ncnc2[nH]ccc12]

Tofacitinib (Pfizer), and which has the chemical name 3-(3R,4R)-4 methyl-3-[methyl-(7H-pyrrolo[2,3-d]pyrimidin-4-yl)-amino]-piperidin-1-yl-3-oxo-propio nitrile.

In one embodiment, the compounds have the formula:

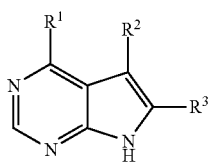

Formula A wherein:
or the pharmaceutically acceptable salt or prodrug thereof;
wherein $R^1$ is a group of the formula

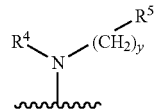

wherein y is 0, 1 or 2;
$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or
$R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo $(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino $(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino $(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-S$(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}(C_1-C_6)$alkyl wherein m is 0, 1 or 2 and $R^{15}$ and $R^{16}$ are each independently selected from hydrogen or $(C_1-C_6)$alkyl; or a group of the formula

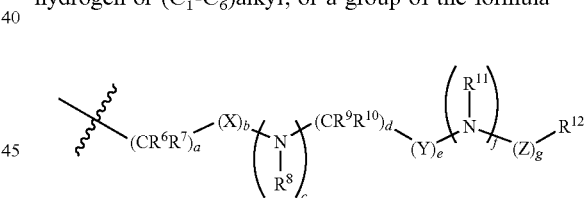

wherein a is 0, 1, 2, 3 or 4;
b, c, e, f and g are each independently 0 or 1;
d is 0, 1, 2, or 3;
X is $S(O)_n$ wherein n is 0, 1 or 2; oxygen, carbonyl or —C(=N-cyano)-;
Y is $S(O)_n$ wherein n is 0, 1 or 2; or carbonyl; and
Z is carbonyl, C(O)O—, C(O)NR— or $S(O)_n$ wherein n is 0, 1 or 2;
$R^6$, $R^7$, $R^8$, $R^9$, $R^{10}$ and $R^{11}$ are each independently selected from the group consisting of hydrogen or $(C_1-C_6)$ alkyl optionally substituted by deuterium, hydroxy, amino, trifluoromethyl, $(C_1-C_6)$acyloxy, $(C_1-C_6)$acylamino, $(C_1-C_6)$ alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—

NH, (C₁-C₆)alkylamino-CO—, (C₂-C₆)alkenyl, (C₂-C₆) alkynyl, (C₁-C₆)alkylamino, hydroxy(C₁-C₆)alkyl, (C₁-C₆) alkoxy(C₁-C₆)alkyl, (C₁-C₆)acyloxy(C₁-C₆)alkyl, nitro, cyano(C₁-C₆)alkyl, halo (C₁-C₆)alkyl, nitro (C₁-C₆)alkyl, trifluoromethyl, trifluoromethyl(C₁-C₆)alkyl, (C₁-C₆)acylamino, (C₁-C₆)acylamino(C₁-C₆)alkyl, (C₁-C₆)alkoxy(C₁-C₆)acylamino, amino(C₁-C₆)acyl, amino(C₁-C₆)acyl(C₁-C₆)alkyl, (C₁-C₆)alkylamino(C₁-C₆)acyl, ((C₁-C₆)alkyl)₂amino(C₁-C₆)acyl, $R^{15}R^{16}N$—CO—O—, $R^{15}R^{16}N$—CO—(C₁-C₆)alkyl, $R^{15}C(O)NH$, $R^{15}OC(O)NH$, $R^{15}NHC(O)NH$, (C₁-C₆)alkyl-S(O)$_m$, (C₁-C₆)alkyl-S(O)$_m$—(C₁-C₆)alkyl, $R^{15}R^{16}NS(O)_m$, $R^{15}R^{16}NS(O)_m$(C₁-C₆)alkyl, $R^{15}S(O)_m R^{16}N$, $R^{15}S(O)_m R^{16}N$(C₁-C₆)alkyl wherein m is 0, 1 or 2 and $R^{15}$ and $R^{16}$ are each independently selected from hydrogen or (C₁-C₆)alkyl;

$R^2$ and $R^3$ are each independently selected from the group consisting of hydrogen, deuterium, amino, halo, hydroxy, nitro, carboxy, (C₂-C₆)alkenyl, (C₂-C₆)alkynyl, trifluoromethyl, trifluoromethoxy, (C₁-C₆)alkyl, (C₁-C₆)alkoxy, (C₃-C₁₀)cycloalkyl wherein the alkyl, alkoxy or cycloalkyl groups are optionally substituted by one to three groups selected from halo, hydroxy, carboxy, amino (C₁-C₆)alkylthio, (C₁-C₆)alkylamino, ((C₁-C₆)alkyl)₂amino, (C₅-C₉)heteroaryl, (C₂-C₉)heterocycloalkyl, (C₃-C₉)cycloalkyl or (C₆-C₁₀)aryl; or $R^2$ and $R^3$ are each independently (C₃-C₁₀) cycloalkyl, (C₃-C₁₀)cycloalkoxy, (C₁-C₆)alkylamino, ((C₁-C₆)alkyl)₂amino, (C₆-C₁₀)arylamino, (C₁-C₆)alkylthio, (C₆-C₁₀)arylthio, (C₁-C₆)alkylsulfinyl, (C₆-C₁₀) arylsulfinyl, (C₁-C₆)alkylsulfonyl, (C₆-C₁₀)arylsulfonyl, (C₁-C₆)acyl, (C₁-C₆)alkoxy-CO—NH—, (C₁-C₆)alkylamino-CO—, (C₅-C₉)heteroaryl, (C₂-C₉)heterocycloalkyl or (C₆-C₁₀)aryl wherein the heteroaryl, heterocycloalkyl and aryl groups are optionally substituted by one to three halo, (C₁-C₆)alkyl, (C₁-C₆)alkyl-CO—NH—, (C₁-C₆)alkoxy-CO—NH—, (C₁-C₆)alkyl-CO—NH—(C₁-C₆)alkyl, (C₁-C₆)alkoxy-CO—NH—(C₁-C₆)alkyl, (C₁-C₆)alkoxy-CO—NH—(C₁-C₆) alkoxy, carboxy, carboxy(C₁-C₆)alkyl, carboxy(C₁-C₆) alkoxy, benzyloxycarbonyl(C₁-C₆)alkoxy, (C₁-C₆) alkoxycarbonyl(C₁-C₆)alkoxy, (C₆-C₁₀)aryl, amino, amino (C₁-C₆)alkyl, (C₁-C₆)alkoxycarbonylamino, (C₆-C₁₀)aryl (C₁-C₆)alkoxycarbonylamino, (C₁-C₆)alkylamino, ((C₁-C₆) alkyl)₂amino, (C₁-C₆)alkylamino(C₁-C₆)alkyl, ((C₁-C₆) alkyl)₂amino(C₁-C₆)alkyl, hydroxy, (C₁-C₆)alkoxy, carboxy, carboxy(C₁-C₆)alkyl, (C₁-C₆)alkoxycarbonyl, (C₁-C₆)alkoxycarbonyl(C₁-C₆)alkyl, (C₁-C₆)alkoxy-CO—NH—, (C₁-C₆)alkyl-CO—NH—, cyano, (C₅-C₉)heterocycloalkyl, amino-CO—NH—, (C₁-C₆)alkylamino-CO—NH—, ((C₁-C₆)alkyl)₂amino-CO—NH—, (C₆-C₁₀) arylamino-CO—NH—, (C₅-C₉)heteroarylamino-CO—NH—, (C₁-C₆)alkylamino-CO—NH—(C₁-C₆)alkyl, ((C₁-C₆)alkyl)₂amino-CO—NH—(C₁-C₆)alkyl, (C₆-C₁₀) arylamino-CO—NH—(C₁-C₆)alkyl, (C₅-C₉) heteroarylamino-CO—NH—(C₁-C₆)alkyl, (C₁-C₆) alkylsulfonyl, (C₁-C₆)alkylsulfonylamino, (C₁-C₆) alkylsulfonylamino(C₁-C₆)alkyl, (C₆-C₁₀)arylsulfonyl, (C₆-C₁₀)arylsulfonylamino, (C₆-C₁₀)arylsulfonylamino(C₁-C₆) alkyl, (C₁-C₆)alkylsulfonylamino, (C₁-C₆) alkylsulfonylamino(C₁-C₆)alkyl, (C₅-C₉)heteroaryl or (C₂-C₉)heterocycloalkyl.

The JAK inhibitors also include compounds of Formula B:

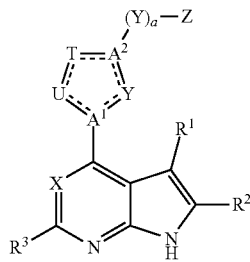

including pharmaceutically acceptable salt forms or prodrugs thereof, wherein:

$A^1$ and $A^2$ are independently selected from C and N;

T, U, and V are independently selected from O, S, N, CR, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene$)$—$(CR^{11}R^{12})_q$, $(CR^{11}R^{12})$-(arylene)-$(CR^{11}R^{12})$, $(CR^{11}R^{12})_p$—$(C_{1-10}$ heterocycloalkylene$)$—$(CR^{11}R^{12})_q$, $(CR^{11}R^{12})_p$-(heteroarylene)-$(CR^{11}R^{12})_q$, $(CR^{11}R^{12})_p O(CR^{11}R^{12})_q$, $(CR^{11}R^{12})_p S(CR^{11}R^{12})_q$, $(CR^{11}R^{12})_p C(O)(CR^{11}R^{12})_q$, $(CR^{11}R^{12})_p C(O)NR_c$ $(CR^{11}R^{12})_q$, $(CR^{11}R^{12})_p C(O)O(CR^{11}R^{12})_q$, $(CR^{11}R^{12})_p OC(O)(CR^{11}R^{12})_q$, $(CR^{11}R^{12})_p OC(O)NR^c(CR^{11}R^{12})_q$, $(CR^{11}R^{12})_p NR^c(CR^{11}R^{12})_q$, $(CR^{11}R^{12})_p NR^c C(O)NR^d$ $(CR^{11}R^{12})_q$, $(CR^{11}R^{12})_p S(O)(CR^{11}R^{12})_q$, $(CR^{11}R^{12})_p S(O)NR(CR^{11}R^{12})_q$, $(CR^{11}R^{12})_p S(O)_2(CR^{11}R^{12})_q$, or $(CR^{11}R^{12})_p S(O)_2 NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -D¹-D2-D3-D4;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R$, $C(O)NR^c R^d$, $C(O)OR^a$, $OC(O)R^b$, $OC(O)NR^c R^d$, $NR^c R^d$, $NR^c C(O)R^b$, $NR^c C(O)NR^c R^d$, $NR^c C(O)OR^a$, $C(=NR^i)$ $NR^c R^d$, $NR^c C(=NR^i)NR^c R^d$, $S(O)R^b$, $S(O)NR^c R^d$, $S(O)_2 R^b$, $NR^c S(O)_2 R^b$, $C(=NOH)R^b$, $C(=NO(C_{1-6}alkyl)R^b$, and $S(O)_2 NR^c R^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $N_2$, $OR^a$, $SR^a$, $C(O)R$, $C(O)NR^c R^d$, $C(O)OR^a$, $OC(O)R^b$, $OC(O)NR^c R^d$, $NR^c R^d$, $NR^c C(O)R^b$, $NR^c C(O)NR^c R^d$, $NR^c C(O)OR^a$, $C(=NR^i)NR^c R^d$, $NR^c C(=NR^i)NR^c R^d$, $S(O)R^b$, $S(O)NR^c R^d$, $S(O)_2 R^b$, $NR^c S(O)_2 R^b$, $C(=NOH)R^b$, $C(=NO(C_{1-6} alkyl))R^b$, and $S(O)_2 NR^c R^d$;

wherein when Z is H, n is 1;

or the —(Y)$_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$ $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —(W)$_m$-Q;

W is $C_{1-8}$ alkylenyl, $C_{2-8}$ alkenylenyl, $C_{2-8}$ alkynylenyl, O, S, C(O), C(O)NR$^{c'}$, C(O)O, OC(O), OC(O)NR$^{c'}$, NR$^{c'}$, NR$^{c'}$C(O)NR$^{d'}$, S(O), S(O)NR$^{c'}$, S(O)$_2$, or S(O)2NR$^{c'}$;

Q is H, halo, CN, NO$_2$, C$_{1-8}$ alkyl, C$_{2-8}$ alkenyl, C$_{2-8}$ alkynyl, C$_{1-8}$ haloalkyl, halosulfanyl, aryl, cycloalkyl, heteroaryl, or heterocycloalkyl, wherein said C$_{1-8}$ alkyl, C$_{2-8}$ alkenyl, C$_{2-8}$ alkynyl, C$_{1-8}$ haloalkyl, aryl, cycloalkyl, heteroaryl, or heterocycloalkyl is optionally substituted with 1, 2, 3 or 4 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^2$, CN, NO$_2$, OR$^{a'}$, SR$^{a'}$, C(O)R$^{b'}$, C(O)NR$^{c'}$R$^{d'}$, C(O)OR$^{a'}$, OC(O)R$^{b'}$, OC(O)NR$^{c'}$R$^{d'}$, NR$^{c'}$R$^{d'}$, NR$^{c'}$C(O)R$^{b'}$, NR$^{c'}$C(O)NR$^{c'}$R$^{d'}$, NR$^{c'}$C(O)OR$^{a'}$, S(O)R$^{b'}$, S(O)NR$^{c'}$R$^{d'}$, S(O)$_2$R$^{b'}$, NR$^{c'}$S(O)$_2$R$^{b'}$, and S(O)$_2$NR$^{c'}$R$^{d'}$;

Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$, NR$^{c''}$S(O)R$^{b''}$, NR$^{c''}$S(O)$_2$R$^{b''}$, S(O)R$^{b''}$, S(O)NR$^{c''}$R$^{d''}$, S(O)$_2$R$^{b''}$, and S(O)$_2$NR$^{c''}$R$^{d''}$;

R$^1$, R$^2$, R$^3$, and R$^4$ are independently selected from H, halo, C$_{1-4}$ alkyl, C$_{2-4}$ alkenyl, C$_{2-4}$ alkynyl, C$_{1-4}$ haloalkyl, halosulfanyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^c$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$;

R$^5$ is H, halo, C$_{1-4}$ alkyl, C$_{2-4}$ alkenyl, C$_{2-4}$ alkynyl, C$_{1-4}$ haloalkyl, halosulfanyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$;

R$^6$ is H, C$_{1-4}$ alkyl, C$_{2-4}$ alkenyl, C$_{2-4}$ alkynyl, C$_{1-4}$ haloalkyl, OR$^7$, C(O)R$^8$, C(O)NR$^9$R$^{10}$, C(O)OR$^7$, S(O)R$^8$, S(O)NR$^9$R$^0$, S(O)$_2$R$^8$, or S(O)$_2$NR$^9$R$^{10}$;

R$^7$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^8$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^9$ and R$^{10}$ are independently selected from H, C$_{1-10}$ alkyl, C$_{1-6}$ haloalkyl, C$_{2-6}$ alkenyl, C$_{2-6}$ alkynyl, C$_{1-6}$ alkylcarbonyl, arylcarbonyl, C$_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or R$^9$ and R$^{10}$ together with the N atom to which they are attached form a 4-, 5-, 6- or 7-membered heterocycloalkyl group;

R$^{11}$ and R$^{12}$ are independently selected from H and -E$^1$-E$^2$-E$^3$-E$^4$;

D$^1$ and E$^1$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^2$ and E$^2$ are independently absent or independently selected from C$_{1-6}$ alkylene, C$_{2-6}$ alkenylene, C$_{2-6}$ alkynylene, (C$_{1-6}$ alkylene)$_r$-O—(C$_{1-6}$ alkylene)$_s$, (C$_{1-6}$ alkylene)$_r$-S—(C$_{1-6}$ alkylene)$_s$, (C$_{1-6}$ alkylene)$_r$-NR$^c$—(C$_{1-6}$ alkylene)$_s$, (C$_{1-6}$ alkylene)$_r$-CO—(C$_{1-6}$ alkylene)$_s$, (C$_{1-6}$ alkylene)$_r$-COO—(C$_{1-6}$ alkylene)$_s$, (C$_{1-6}$ alkylene)$_r$-CONR$^c$—(C$_{1-6}$ alkylene)$_s$, (C$_{1-6}$ alkylene)$_r$-SO—(C$_{1-6}$ alkylene)$_s$, (C$_{1-6}$ alkylene)$_r$-SO$_2$—(C$_{1-6}$ alkylene)$_s$, (C$_{1-6}$ alkylene)$_r$-SONR$^c$—(C$_{1-6}$ alkylene)$_s$, and (C$_{1-6}$ alkylene)$_r$-NR$^c$CONR$^f$—(C$_{1-6}$ alkylene)$_s$, wherein each of the C$_{1-6}$ alkylene, C$_{2-6}$ alkenylene, and C$_{2-6}$ alkynylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^3$ and E$^3$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

E$^4$ and E$^4$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^a$, C(O)OR$^a$, OC(O)R$^b$OC(O)NR$^c$R$^d$ NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^b$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{a'}$ and R$^{a''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^{b'}$ and R$^{b''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^c$ and $R^d$ are independently selected from H, $Cy^1$, —($C_{1-6}$ alkyl)-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

or $R^c$ and $R^d$ together with the N atom to which they are attached form a 4-, 5-, 6- or 7-membered heterocycloalkyl group optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^i$ is H, CN, $NO_2$, or $C_{1-6}$ alkyl;
$R^e$ and $R^f$ are independently selected from H and $C_{1-6}$alkyl;
$R^t$ is H, CN, or $NO_2$;
m is 0 or 1;
n is 0 or 1;
p is 0, 1, 2, 3, 4, 5, or 6;
q is 1, 2, 3, 4, 5 or 6;
r is 0 or 1; and
s is 0 or 1.

Additional JAK inhibitors include CEP-701 (Lestaurtinib, Cephalon Technology), a JAK 2 FL3 kinase, AZD1480 (Astra Zeneca), a JAK 2 inhibitor, LY3009104/INCB28050 (Eli Lilly, Incyte), a JAK 1/2 inhibitor, Pacritinib/SB1518 (S*BIO), a JAK 2 inhibitor, VX-509 (Vertex), a JAK 3 inhibitor, GLPG0634 (Galapagos), a JAK 1 inhibitor, INC424 (Novartis), a JAK inhibitor, R-348 (Rigel), a JAK 3 inhibitor, CYT387 (YM Bioscience), a JAK1/2 inhibitor, TG 10138, a JAK 2 inhibitor, AEG 3482 (Axon), a JAK inhibitor, and pharmaceutically-acceptable salts and prodrugs thereof.

Lestaurtinib has the following formula:

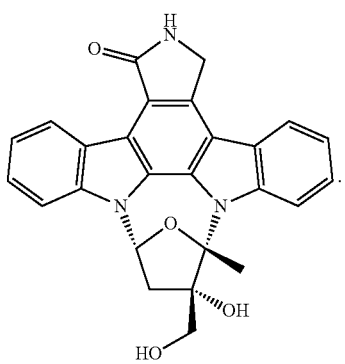 [SMILES: C[C@]12O[C@H](C[C@]1(O)CO)n1c3ccccc3c3c4c(c5c6ccccc6n2c5c31)CNC4=O]

AEG 3482 has the following formula:

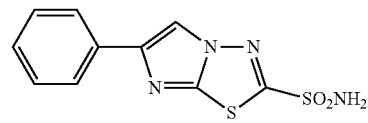 [SMILES: NS(=O)(=O)c1nn2cc(-c3ccccc3)nc2s1]

TG 10138 has the following formula:

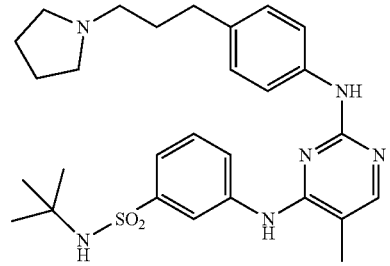 [SMILES: Cc1cnc(Nc2ccc(CCCN3CCCC3)cc2)nc1Nc1cccc(S(=O)(=O)NC(C)(C)C)c1]

CYT387 has the following formula:

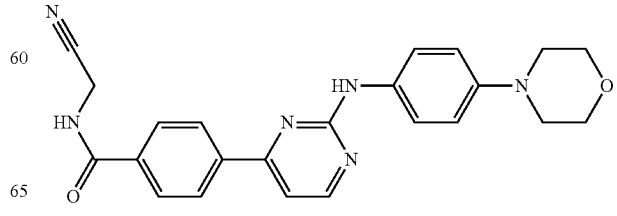

AZD1480 has the following formula:

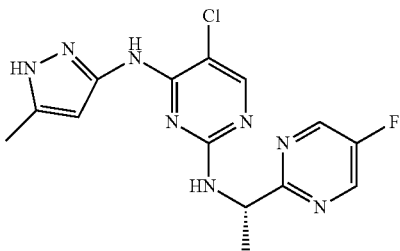 [SMILES: Cc1cc(Nc2nc(N[C@@H](C)c3ncc(F)cn3)ncc2Cl)n[nH]1]

LY3009104 is believed to be (R)-3-(4-(7H-pyrrolo[2,3-d]pyrimidin-4-yl)-1H-pyrazol-1-yl-3-cyclopentyl-propanenitrile Pacritinib has the following formula:

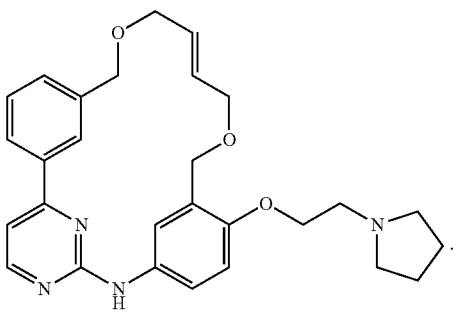 [SMILES: C1=C/COCc2cc(ccc2OCCN2CCCC2)Nc2nccc(n2)-c2cccc(c2)COC/1]

The compounds include those described in U.S. Publication Nos. 20110020469; 20110118255; 20100311743; 20100310675; 20100280026; 20100160287; 20100081657; 20100081645; 20090181938; 20080032963; 20070259869; and 20070249031.

The compounds also include those described in U.S. Publication Nos. 20110251215; 20110224157; 20110223210; 20110207754; 20110136781; 20110086835; 20110086810; 20110082159; 20100190804; 20100022522; 20090318405; 20090286778; 20090233903; 20090215766; 20090197869; 20090181959; 20080312259; 20080312258; 20080188500; and 20080167287; 20080039457.

The compounds also include those described in U.S. Publication Nos. 20100311693; 20080021013; 20060128780; 20040186157; and 20030162775.

The compounds also include those described in U.S. Publication Nos. 20110245256; 20100009978; 20090098137; and 20080261973.

The compounds also include those described in U.S. Publication No. 20110092499. Representative compounds include:
1. 7-iodo-N-(4-morpholinophenyl)thieno[3,2-d]pyrimidin-2-amine 2. 7-(4-aminophenyl)-N-(4-morpholinophenyl)thieno[3,2-d]pyrimidin-2-amine 3. N-(4-(2-(4-morpholinophenylamino)thieno[3,2-d]pyrimidin-7-yl)phenyl)acrylamide 4. 7-(3-aminophenyl)-N-(4-morpholinophenyl)thieno[3,2-d]pyrimidin-2-amine 5. N-(3-(2-(4-morpholinophenylamino)thieno[3,2-d]pyrimidin-7-yl)phenyl)acrylamide 7. N-(4-morpholinophenyl)thieno[3,2-d]pyrimidin-2-amine 8. methyl 2-(4-morpholinophenylamino)thieno[3,2-d]pyrimidine-7-carboxylate 9. N-(4-morpholinophenyl)-5H-pyrrolo[3,2-d]pyrimidin-2-amine 10. 7-(4-amino-3-methoxyphenyl)-N-(4-morpholinophenyl)thieno[3,2-d]pyrimidin-2-amine 11. 4-(2-(4-morpholinophenylamino)thieno[3,2-d]pyrimidin-7-yl)benzenesulfonam-ide 12. N,N-dimethyl-3-(2-(4-morpholinophenylamino)thieno[3,2-d]pyrimidin-7-yl)benzenesulfonamide 13. 1-ethyl-3-(2-methoxy-4-(2-(4-morpholinophenylamino)thieno[3,2-d]pyrimidin-7-yl)phenyl)urea 14. N-(4-(2-(4-morpholinophenylamino)thieno[3,2-d]pyrimidin-7-yl)phenyl)metha-nesulfonamide 15. 2-methoxy-4-(2-(4-morpholinophenylamino)thieno[3,2-d]pyrimidin-7-yl)pheno-1 16. 2-cyano-N-(3-(2-(4-morpholinophenylamino)thieno[3,2-d]pyrimidin-7-yl-)phenyl)acetamide 17. N-(cyanomethyl)-2-(4-morpholinophenylamino)thieno[3,2-d]pyrimidine-7-carboxamide 18. N-(3-(2-(4-morpholinophenylamino)thieno[3,2-d]pyrimidin-7-yl)phenyl)metha-nesulfonamide 19. 1-ethyl-3-(4-(2-(4-morpholinophenylamino)thieno[3,2-d]pyrimidin-7-yl)-2-(-trifluoromethoxy)phenyl)urea 20. N-(3-nitrophenyl)-7-phenylthieno[3,2-d]pyrimidin-2-amine 21. 7-iodo-N-(3-nitrophenyl)thieno[3,2-d]pyrimidin-2-amine 22. N1-(7-(2-ethylphenyl)thieno[3,2-d]pyrimidin-2-yl)benzene-1,3-diamine 25. N-tert-butyl-3-(2-(4-morpholinophenylamino)thieno[3,2-d]pyrimidin-7-yl)be-nzenesulfonamide 26. N1-(7-iodothieno[3,2-d]pyrimidin-2-yl)benzene-1,3-diamine 28. 7-(4-amino-3-(tri fluoromethoxy)phenyl)-N-(4-morpholinophenyl)thieno[3,2-d]pyrimidin-2-amin-e 29. 7-(2-ethylphenyl)-N-(4-morpholinophenyl)thieno[3,2-d]pyrimidin-2-ami-ne 30. N-(3-(2-(4-morpholinophenylamino)thieno[3,2-d]pyrimidin-7-yl)phenyl-)acetamide 31. N-(cyanomethyl)-N-(3-(2-(4-morpholinophenylamino)thieno[3,2-d]pyrimidin-7-yl)phenyl)methanesulfonamide 32. N-(cyanomethyl)-N-(4-(2-(4-morpholinophenylamino)thieno[3,2-d]pyrimidin-7-yl)phenyl)methanesulfonamide 33. N-(3-(5-methyl-2-(4-morpholinophenylamino)-5H-pyrrolo[3,2-d]pyrimidin-7-y-l)phenyl)methanesulfonamide 34. 4-(5-methyl-2-(4-morpholinophenylamino)-5H-pyrrolo[3,2-d]pyrimidin-7-yl)b-enzenesulfonamide 36. N-(4-(5-methyl-2-(4-morpholinophenylamino)-5H-pyrrolo[3,2-d]pyrimidin-7-yl)phenyl)methanesulfonamide 37. 7-iodo-N-(4-morpholinophenyl)-5H-pyrrolo[3,2-d]pyrimidin-2-amine 38. 7-(2-isopropylphenyl)-N-(4-morpholinophenyl)thieno[3,2-d]pyrimidin-2-amin-e 39. 7-bromo-N-(4-morpholinophenyl)thieno[3,2-d]pyrimidin-2-amine 40. N7-(2-isopropylphenyl)-N2-(4-morpholinophenyl)thieno[3,2-d]pyrimidine-2,7-diamine 41. N7-(4-isopropylphenyl)-N2-(4-morpholinophenyl)thieno[3,2-d]pyrimidine-2,7-diamine 42. 7-(5-amino-2-methylphenyl)-N-(4-morpholinophenyl)thieno[3,2-d]pyrimidin-2-amine 43. N-(cyanomethyl)-4-(2-(4-morpholinophenylamino)thieno[3,2-d]pyri-midin-7-yl)benzamide 44. 7-iodo-N-(3-morpholinophenyl)thieno[3,2-d]pyrimidin-2-amine 45. 7-(4-amino-3-nitrophenyl)-N-(4-morpholinophenyl)thieno[3,2-d]pyrimidin-2-amine 46. 7-(2-methoxypyridin-3-yl)-N-(4-morpholinophenyl)thieno[3,2-d]pyr-imidin-2-amine 47. (3-(7-iodothieno[3,2-d]pyrimidin-2-ylamino)phenyl)methanol 48. N-tert-butyl-3-(2-(3-morpholinophenylamino)thieno[3,2-d]pyrimidin-7-yl)be-nzenesulfonamide 49. N-tert-butyl-3-(2-(3-(hydroxymethyl)phenylamino)thieno[3,2-d]pyrimidin-7-yl)benzenesulfonamide 50. N-(4-morpholinophenyl)-7-(4-nitrophenylthio)-5H-pyrrolo[3,2-d]pyrimidin-2-amine 51. N-tert-butyl-3-(2-(3,4,5-trimethoxyphenylamino)thieno[3,2-d]pyr-imidin-7-yl)benzenesulfonamide 52. 7-(4-amino-3-nitrophenyl)-N-(3,4-dimethoxyphenyl)thieno[3,2-d]pyrimi-din-2-amine 53. N-(3,4-dimethoxyphenyl)-7-(2-methoxypyridin-3-yl)thieno[3,2-d]p-yrimidin-2-amine 54. N-tert-butyl-3-(2-(3,4-dimethoxyphenylamino)thieno[3,2-d]pyrimidin-7-yl)b-enzenesulfonamide 55. 7-(2-aminopyrimidin-5-yl)-N-(3,4-dimethoxyphenyl)thieno[3,2-d]py-rimidin-2-amine 56. N-(3,4-dimethoxyphenyl)-7-(2,6-dimethoxypyridin-3-yl)thieno[3,2-d]pyrimidin-2-amine 57. N-(3,4-dimethoxyphenyl)-7-(2,4-dimethoxypyrimidin-5-yl)

thieno[3,2-d]pyrim-idin-2-amine 58. 7-iodo-N-(4-(morpholinomethyl)phenyl)thieno[3,2-d]pyrimidin-2-amine 59. N-tert-butyl-3-(2-(4-(morpholinomethyl)phenylamino)thieno[3,2-d]pyrimidin-7-yl)benzenesulfonamide 60. 2-cyano-N-(4-methyl-3-(2-(4-morpholinophenylamino)thieno[3,2-d]pyrimidin-7-yl)phenyl)acetamide 61. ethyl 3-(2-(4-morpholinophenylamino)thieno[3,2-d]pyrimidin-7-yl)benzoate 62. 7-bromo-N-(4-(2-(pyrrolidin-1-yl)ethoxy)phenyl)thieno[3,2-d]pyrimidin-2-a-mine 63. N-(3-(2-(4-(2-(pyrrolidin-1-yl)ethoxy)phenylamino)thieno[3,2-d]pyrimidin-7-yl)phenyl)acetamide 64. N-(cyanomethyl)-3-(2-(4-morpholinophenylamino)thieno[3,2-d]pyrimidin-7-yl-)benzamide 65. N-tert-butyl-3-(2-(4-morpholinophenylamino)thieno[3,2-d]pyrimidin-7-yl)benzamide 66. N-tert-butyl-3-(2-(4-(1-ethylpiperidin-4-yloxy)phenylamino)thieno[3,2-d]p-yrimidin-7-yl)benzenesulfonamide 67. tert-butyl 4-(2-(4-(morpholinomethyl)phenylamino)thieno[3,2-d]pyrimidin-7-yl)-1H-pyr-azole-1-carboxylate 68. 7-bromo-N-(4-((4-ethylpiperazin-1-yl)methyl)phenyl)thieno[3,2-d]pyrimidin-2-amine 69. N-tert-butyl-3-(2-(4-((4-ethylpiperazin-1-yl)methyl)phenylamino)thieno[3,-2-d]pyrimidin-7-yl)benzenesulfonamide 70. N-(4-((4-ethylpiperazin-1-yl)methyl)phenyl)-7-(1H-pyrazol-4-yl)thieno[3,2-d]pyrimidin-2-amine 71. N-(cyanomethyl)-3-(2-(4-(morpholinomethyl)phenylamino)thieno[3,2-d]pyrimi-din-7-yl)benzamide 72. N-tert-butyl-3-(2-(4-(2-(pyrrolidin-1-yl)ethoxy)phenylamino)thieno[3,2-d]-pyrimidin-7-yl)benzenesulfonamide 73. tert-butyl pyrrolidin-1-yl)ethoxy)phenylamino)thieno[3,2-d]pyrimidin-7-yl)benzylcarbamate 74. 3-(2-(4-(2-(pyrrolidin-1-yl)ethoxy)phenylamino)thieno[3,2-d]pyri-midin-7-yl)benzenesulfonamide 75. 7-(3-chloro-4-fluorophenyl)-N-(4-(2-(pyrrolidin-1-yl)ethoxy)phenyl)thieno-[3,2-d]pyrimidin-2-amine 76. tert-butyl 4-(2-(4-(1-ethylpiperidin-4-yloxy)phenylamino)thieno[3,2-d]pyrimidin-7-yl)-1H-pyrazole-1-carboxylate 77. 7-(benzo[d][1,3]dioxol-5-yl)-N-(4-(morpholinomethyl)phenyl)thieno[3,2-d]p-yrimidin-2-amine 78. tert-butyl 5-(2-(4-(morpholinomethyl)phenylamino)thieno[3,2-d]pyrimidin-7-yl)-1H-ind-ole-1-carboxylate 79. 7-(2-aminopyrimidin-5-yl)-N-(4-(morpholinomethyl)phenyl)thieno[3,2-d]pyrimidin-2-amine 80. tert-butyl 4-(2-(4-(morpholinomethyl)phenylamino)thieno[3,2-d]pyrimidin-7-yl)-5,6-dihydropyridine-1(2H)-carboxylate 81. tert-butyl morpholinomethyl)phenylamino)thieno[3,2-d]pyrimidin-7-yl)benzylcarbamate 82. N-(3-(2-(4-(morpholinomethyl)phenylamino)thieno[3,2-d]pyrimidin-7-yl)-phenyl)acetamide 83. N-(4-(2-(4-(morpholinomethyl)phenylamino)thieno[3,2-d]pyrimidin-7-yl)phen-yl)acetamide 84. N-(3-(2-(4-(morpholinomethyl)phenylamino)thieno[3,2-d]pyrimidin-7-yl)phen-yl)methanesulfonamide 85. 7-(4-(4-methylpiperazin-1-yl)phenyl)-N-(4-(morpholinomethyl)phenyl)thieno-[3,2-d]pyrimidin-2-amine 86. N-(2-methoxy-4-(2-(4-(morpholinomethyl)phenylamino)thieno[3,2-d]pyrimidin-7-yl)phenyl)acetamide 87. 7-bromo-N-(3,4,5-trimethoxyphenyl)thieno[3,2-d]pyrimidin-2-amine 88. (3-(2-(3,4,5-trimethoxyphenylamino)thieno[3,2-d]pyrimidin-7-yl)phenyl)met-hanol 89. (4-(2-(3,4,5-trimethoxyphenylamino)thieno[3,2-d]pyrimidin-7-yl)p-henyl)methanol 90. (3-(2-(4-morpholinophenylamino)thieno[3,2-d]pyrimidin-7-yl)phenyl)methano-l 91. (4-(2-(4-morpholinophenylamino)thieno[3,2-d]pyrimidin-7-yl)phenyl)me-thanol 92. N-(pyrrolidin-1-yl)ethoxy)phenylamino)thieno[3,2-d]pyrimidin-7-yl)benzyl) methanesulfonamide 93. tert-butyl morpholinomethyl)phenylamino)thieno[3,2-d]pyrimidin-7-yl)benzylcarbamate 94. N-(4-(morpholinomethyl)phenyl)-7-(3-(piperazin-1-yl)phenyl)thieno[3,2-d]pyrimidin-2-amine 95. 7-(6-(2-morpholinoethylamino)pyridin-3-yl)-N-(3,4,5-trimethoxyphenyl)thie-no[3,2-d]pyrimidin-2-amine 96. 7-(2-ethylphenyl)-N-(4-(2-(pyrrolidin-1-yl)ethoxy)phenyl)thieno[3,2-d]pyrimidin-2-amine 97. 7-(4-(aminomethyl)phenyl)-N-(4-(morpholinomethyl)phenyl)thieno[3,2-d]pyrimidin-2-amine 98. N-(4-(1-ethylpiperidin-4-yloxy)phenyl)-7-(1H-pyrazol-4-yl)thieno[3,2-d]pyrimidin-2-amine 99. N-(2,4-dimethoxyphenyl)-7-phenylthieno[3,2-d]pyrimidin-2-amine 100. 7-bromo-N-(3,4-dimethoxyphenyl)thieno[3,2-d]pyrimidin-2-amine 101. N-(3,4-dimethoxyphenyl)-7-phenylthieno[3,2-d]pyrimidin-2-amine R348 (Rigel) is defined in Velotta et al., "A novel JAK3 inhibitor, R348, attenuates chronic airway allograft rejection," Transplantation. 2009 Mar. 15; 87(5):653-9.

The present invention also relates to the pharmaceutically acceptable acid addition salts of compounds of Formulas A and B, as well as the additional JAK inhibitors described herein. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of Formulas A and B. The chemical bases that may be used as reagents to prepare pharmaceutically acceptable base salts of those compounds of Formulas A and B that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all conformational isomers (e.g., cis and trans isomers. The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations. The compounds of Formulas A and B can also exist as tautomers. This invention relates to the use of all such tautomers and mixtures thereof.

This invention also encompasses pharmaceutical compositions containing prodrugs of compounds of the Formulas A and B, and their use in treating or preventing HIV. This invention also encompasses methods of treating or preventing viral infections that can be treated or prevented by protein kinase inhibitors, such as the enzyme Janus Kinase 1, 2, or 3, comprising administering prodrugs of compounds of the Formulas A and B. Compounds of Formulas A and B having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of Formulas A and B. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of Formulas A and B through the carbonyl carbon prodrug sidechain.

II. Combinations of JAK Inhibitors and Other Antiviral Agents

In one embodiment, the compositions include antiretroviral JAK inhibitors as described herein and one or more additional antiviral agents.

In one aspect of this embodiment, the JAK inhibitors and additional antiviral agents are administered in combination or alternation, and in one aspect, in a manner in which both agents act synergistically against the virus. The compositions and methods described herein can be used to treat patients infected with a drug resistant form of HIV, specifically, a form including the M184V/I, multidrug resistant viruses (e.g., Q151M), K65R mutation, Thymidine analog mutations (TAMS), and the like. TAMS include, but are not limited to, mutations at reverse transcriptase (RT) positions 41, 67, 70, 210, 215, and 219, which confer clinically significant resistance to each of the nucleoside RT inhibitors with the exception of 3TC.

While not wishing to be bound to a particular theory, it is believed that the JAK inhibitors described herein function in a way not associated with heretofore known antiretroviral therapy, in that the compounds do not act in the same way as NRTI, NNRTI, protease inhibitors, integrase inhibitors, entry inhibitors, and the like, all of which interfere directly with a step in the viral replication cycle. Rather, they act in an intracellular manner, in a way that is not likely to provoke resistance. More specifically, the mechanism is independent and distinct from direct modulation or interference with the viral replication cycle itself, and therefore lacks a selective pressure to confer emergence of drug resistant virus.

Further, the combination of the JAK inhibitors described herein, and one or more additional antiviral agents, can help prevent the development of viral resistance to other antiviral agents. Therefore, co-formulation of the JAK inhibitors with these additional antiviral agents can function as a "resistance repellent" for the various mutations associated with conventional therapy, and provides better therapy than either alone.

In one aspect of this embodiment, a combination therapy is administered that has the capability of attacking HIV in a variety of mechanisms. That is, the combination therapy includes an effective amount of at least one adenine, cytosine, thymine, and guanosine nucleoside antiviral, as well as one or more additional agents other than NRTI that inhibit HIV viral loads via a different mechanism. Examples include reverse transcriptase inhibitors, protease inhibitors, fusion inhibitors, entry inhibitors, attachment inhibitors, polymerase inhibitors, and integrase inhibitors such as integrase inhibitors such as raltegravir (Isentress) or MK-0518, GS-9137 (Gilead Sciences), GS-8374 (Gilead Sciences), or GSK-364735.

It is believed that this therapy, particularly when administered at an early stage in the development of HIV infection, has the possibility of eliminating HIV infection in a patient. That is, the presence of the different nucleosides and additional agents minimizes the ability of the virus to adapt its reverse transcriptase and develop resistance to any class of nucleoside antiviral nucleosides (i.e., adenine, cytosine, thymidine, or guanine), because it would be susceptible to at least one of the other nucleoside antiviral agents that are present, and/or the additional non-NRTI therapeutic agent. In addition the lipophilic character of certain agents would allow them to penetrate certain compartments where virus could replicate (e.g., brain, testicles, gut).

Representative agents are described in more detail below.

Attachment and Fusion Inhibitors

Attachment and fusion inhibitors are anti-HIV drugs which are intended to protect cells from infection by HIV by preventing the virus from attaching to a new cell and breaking through the cell membrane. These drugs can prevent infection of a cell by either free virus (in the blood) or by contact with an infected cell. These agents are susceptible to digestive acids, so are commonly delivered by break them down, most of these drugs are given by injections or intravenous infusion.

Examples are shown in the table that follows:

| Entry Inhibitors (including Fusion Inhibitors) | | | | |
|---|---|---|---|---|
| Brand Name | Generic Name | Abbreviation | Experimental Code | Pharmaceutical Company |
| Fuzeon™ | enfuvirtide | | T-20 | Trimeris |
| | | | T-1249 | Trimeris |
| | | | AMD-3100 | AnorMED. Inc. |
| | CD4-IgG2 | | PRO-542 | Progenics Pharmaceuticals |
| | | | BMS-488043 | Bristol-Myers Squibb |
| | aplaviroc | | GSK-873, 140 | GlaxoSmithKline |
| | Peptide T | | | Advanced Immuni T, Inc. |
| | | | TNX-355 | Tanox, Inc. |
| | maraviroc | | UK-427, 857 | Pfizer |
| | | CXCR4 Inhibitor | | |
| | AMD070 | | AMD11070 | AnorMED, Inc. |
| | | CCR5 antagonist | | |
| Vicriroc | | SCH-D | SCH-417690 | Schering-Plough |

Additional fusion and attachment inhibitors in human trials include AK602, AMD070, BMS-378806, HGS004, INCB9471, PRO 140, Schering C, SP01A, and TAK-652.

AK602 is a CCR5 blocker being developed by Kumamoto University in Japan.

AMD070 by AnorMed blocks the CXCR4 receptor on CD4 T-cells to inhibit HIV fusion.

BMS-378806 is an attachment inhibitor that attaches to gp120, a part of HIV.

HGS004 by Human Genome Sciences, is a monoclonal antibody CCR5 blocker.

INCB 9471 is sold by Incyte Corporation.

PRO 140 by Progenics blocks fusion by binding to a receptor protein on the surface of CD4 cells.

SP01A by Samaritan Pharmaceuticals is an HIV entry inhibitor.

TAK-652 by Takeda blocks binding to the CCR5 receptor.

Polymerase Inhibitors

The DNA polymerization activity of HIV-1 reverse transcriptase (RT) can be inhibited by at least three mechanistically distinct classes of compounds. Two of these are chain terminating nucleoside analogs (NRTIs) and allosteric non-nucleoside RT inhibitors (NNRTIs). The third class includes pyrophosphate mimetics such as foscarnet (phosphonoformic acid, PFA).

The reverse transcriptase has a second enzymatic activity, ribonuclease H (RNase H) activity, which maps to a second active site in the enzyme. RNase H activity can be inhibited by various small molecules (polymerase inhibitors). Examples include diketo acids, which bind directly to the RNase H domain, or compounds like PFA, which are believed to bind in the polymerase domain.

Examples of these compounds are listed in the tables that follow.

| HIV Therapies: Nucleoside/Nucleotide Reverse Transcriptase Inhibitors (NRTIs) | | | | |
|---|---|---|---|---|
| Brand Name | Generic Name | Abbreviation | Experimental Code | Pharmaceutical Company |
| | Dapavir, 2,6-diaminopurine dioxolane | DAPD | | RFS Pharma |
| Retrovir ® | zidovudine | AZT or ZDV | | GlaxoSmithKline |
| Epivir ® | lamivudine | 3TC | | GlaxoSmithKline |
| Combivir ® | zidovudine + lamivudine | AZT + 3TC | | GlaxoSmithKline |
| Trizivir ® | abacavir + zidovudine + lamivudine | ABC + AZT + 3TC | | GlaxoSmithKline |
| Ziagen ® | abacavir | ABC | 1592U89 | GlaxoSmithKline |
| Epzicom ™ | abacavir + lamivudine | ABC + 3TC | | GlaxoSmithKline |
| Hivid ® | zalcitabine | ddC | | Hoffmann-La Roche |
| Videx ® | didanosine: buffered versions | ddI | BMY-40900 | Bristol-Myers Squibb |
| Entecavir | baraclude | | | Bristol-Myers Squibb |
| Videx ® EC | didanosine: delayed-release capsules | ddI | | Bristol-Myers Squibb |
| Zerit ® | stavudine | d4T | BMY-27857 | Bristol-Myers Squibb |
| Viread ™ | tenofovir disoproxil fumarate (DF) | TDF or Bis(POC) PMPA | | Gilead Sciences |
| Emtriva ® | emtricitabine | (−)-FTC | | Gilead Sciences |
| Truvada ® | Vircad + Emtriva | TDF + (−)-FTC | | Gilead Sciences |
| Atripla ™ | | TDF + (−)-FTC + Sustiva ® | | Gilead/BMS/Merck |
| | Amdoxovir | DAPD, AMDX | | RFS Pharma LLC |
| Apricitabine | AVX754 | | SPD 754 | Avexa Ltd |
| | Alovudine | FLT | MIV-310 | Medivir |
| | Elvucitabine | L-FD4C | ACH-126443, SN1461, SN1212 | Achillion Koronis |
| | KP-1461 | | | |
| | Racivir | RCV | | Emory University |
| | | DOT | | Emory University |
| Dexelvucitabine | Reverset | D-D4FC, DFC | DPC 817 | Emory University |
| | | | GS9148 and prodrugs thereof | Gilead Sciences |

| HIV Therapies: Non-Nucleoside Reverse Transcriptase Inhibitors (NNRTIs) | | | | |
|---|---|---|---|---|
| Brand Name | Generic Name | Abbreviation | Experimental Code | Pharmaceutical Company |
| Viramune ® | nevirapine | NVP | BI-RG-587 | Boehringer Ingelheim |
| Rescriptor ® | delavirdine | DLV | U-90152S/T | Pfizer |
| Sustiva ® | efavirenz | EFV | DMP-266 | Bristol-Myers Squibb |
| | (+)-calanolide A | | | Sarawak Medichem |
| | capravirine | CPV | AG-1549 or S-1153 | Pfizer |
| | | | DPC-083 | Bristol-Myers Squibb |
| | | | TMC-125 | Tibotec-Virco Group |
| | | | TMC-278 | Tibotec-Virco Group |

-continued

| HIV Therapies: Non-Nucleoside Reverse Transcriptase Inhibitors (NNRTIs) | | | | |
|---|---|---|---|---|
| Brand Name | Generic Name | Abbreviation | Experimental Code | Pharmaceutical Company |
| | | | IDX12899 | Idenix |
| | | | IDX12989 | Idenix |
| RDEA806 | | | | Ardea Bioscience, Inc. |

Integrase Inhibitors

Representative integrase inhibitors include globoidnan A, L-000870812, S/GSK1349572, S/GSK1265744, Raltegravir and Elvitegravir with or without a pharmacokinetic (PK) booster such as ritonavir or Gilead's pharmacoenhancing agent (also referred to as a PK booster), GS 9350.

Suitable integrase inhibitors include those described in:

U.S. patent application Ser. No. 11/595,429, entitled "HIV INTEGRASE INHIBITORS" filed in the name of B. Narasimhulu Naidu, et al. on Nov. 10, 2006 and published on May 17, 2007 as U.S. Publication No. 20070111985 and assigned to Bristol-Meyers Squibb Company.

U.S. patent application Ser. No. 11/561,039, entitled "HIV INTEGRASE INHIBITORS" filed in the name of B. Narasimhulu Naidu, et al. on Nov. 17, 2006 and published on Jun. 7, 2007 as U.S. Publication No. 20070129379 and assigned to Bristol-Meyers Squibb Company.

U.S. patent application Ser. No. 11/599,580, entitled "HIV INTEGRASE INHIBITORS" filed in the name of B. Narasimhulu Naidu, et al. on Nov. 14, 2006 and published on May 17, 2007 as U.S. Publication No. 20070112190 and assigned to Bristol-Meyers Squibb Company.

U.S. patent application Ser. No. 11/754,462, entitled "HIV INTEGRASE INHIBITORS" filed in the name of B. Narasimhulu Naidu, et al. on May 29, 2007 and published on Dec. 6, 2007 as U.S. Publication No. 20070281917 and assigned to Bristol-Meyers Squibb Company.

U.S. patent application Ser. No. 11/768,458, entitled "HIV INTEGRASE INHIBITORS" filed in the name of Michael A. Walker, et al. on Jun. 26, 2007 and published Jan. 3, 2008 as U.S. Publication No. 20080004265 and assigned to Bristol-Meyers Squibb Company.

U.S. patent application Ser. No. 12/132,145, entitled "HIV INTEGRASE INHIBITORS" filed in the name of B. Narasimhulu Naidu, et al. on Jun. 3, 2008; published on Dec. 11, 2008 as U.S. Publication No. 20080306051 and assigned to Bristol-Meyers Squibb Company.

U.S. patent application Ser. No. 11/505,149, entitled "BICYCLIC HETEROCYCLES AS HIV INTEGRASE INHIBITORS" filed in the name of B.

Narasimhulu Naidu, et al. on Aug. 16, 2006 and published on Dec. 7, 2006 as U.S. Publication No. 20060276466.

U.S. patent application Ser. No. 11/590,637, entitled "HIV INTEGRASE INHIBITORS" filed in the name of B. Narasimhulu Naidu, et al. on Oct. 31, 2006 and published on May 17, 2007 as U.S. Publication No. 20070111984 and assigned to Bristol-Meyers Squibb Company.

U.S. patent application Ser. No. 12/162,975, entitled "USE OF 6-(3-CHLORO-2-FLUOROBENZYL)-1-[(2S)-1-HYDROXY-3-METHYLBUTAN-2-YL]-7-METHOXY-4-OXO-1,4-DIHYDROQUINOLINE-3-CARBOXYLIC ACID OR SALT THEREOF FOR TREATING RETROVIRUS INFECTION" filed in the name of Yuji Matsuzaki, et al. on Feb. 1, 2007 and published on Jan. 15, 2009 as U.S. Publication No. 20090018162.

U.S. patent application Ser. No. 11/767,021, entitled "6-(HETEROCYCLYL-SUBSTITUTED BENZYL)-4-OXOQUINOLINE COMPOUND AND USE THEREOF AS HIV INTEGRASE INHIBITOR" filed in the name of Motohid, Satoh, et al. on Jun. 22, 2007 and published on Aug. 28, 2008 as U.S. Publication No. 20080207618.

U.S. patent application Ser. No. 12/042,628, entitled "USE OF QUINOLINE DERIVATIVES WITH ANTI-INTEGRASE EFFECT AND APPLICATIONS THEREOF" filed in the name of Aurelia Mousnier, et al. on Mar. 5, 2008 and published on Jul. 3, 2008 as U.S. Publication No. 20080161350 and assigned to Bioalliance Pharma SA.

U.S. patent application Ser. No. 12/169,367, entitled "NOVEL PYRIMIDINECARBOXAMIDE DERIVATIVES" filed in the name of Scott L. Harbeson on Jul. 8, 2008 and published on Feb. 5, 2009 as U.S. Publication No. 20090035324.

U.S. patent application Ser. No. 10/587,857, entitled "NAPHTHYRIDINE DERIVATIVES HAVING INHIBITORY ACTIVITY AGAINST HIV INTEGRASE" filed in the name of Teruhiko Taishi, et al. on Feb. 2, 2005 and published on Sep. 10, 2009 as U.S. Publication No. 20090227621.

U.S. patent application Ser. No. 11/500,387, entitled "NITROGEN-CONTAINING HETEROARYL COMPOUNDS HAVING INHIBITORY ACTIVITY AGAINST HIV INTEGRASE" filed in the name of Masahiro Fuji, et al. on Aug. 8, 2006 and published on Dec. 28, 2006 as U.S. Publication No. 20060293334.

U.S. patent application Ser. No. 12/097,859, entitled "METHODS FOR IMPROVING THE PHARMACOKINETICS OF HIV INTEGRASE INHIBITORS" filed in the name of Brian P. Kearney, et al. on Dec. 29, 2006 and published on Sep. 17, 2009 as U.S. Publication No. 20090233964 and assigned to Gilead Sciences, Inc.

U.S. patent application Ser. No. 11/807,303, entitled "PRE-ORGANIZED TRICYCLIC INTEGRASE INHIBITOR COMPOUNDS" filed in the name of James M. Chen, et al. on May 25, 2007 and published on Jan. 29, 2009 as U.S. Publication No. 20090029939 and assigned to Gilead Sciences, Inc.

U.S. patent application Ser. No. 10/587,601, entitled "HIV INTEGRASE INHIBITORS" filed in the name of Philip Jones, et al. on Mar. 1, 2005 and published on Jul. 12, 2007 as U.S. Publication No. 20070161639 and assigned to Merck and Co., Inc.

U.S. patent application Ser. No. 10/592,222, entitled "HIV INTEGRASE INHIBITORS" filed in the name of Peter D. Jones, et al. on Mar. 4, 2005 and published on Jan. 10, 2008 as U.S. Publication No. 20080009490 and assigned to Merck and Co., Inc.

U.S. patent application Ser. No. 11/992,531, entitled "HIV INTEGRASE INHIBITORS" filed in the name of Vincenzo Summa, et al. on Sep. 26, 2006 and published on Sep. 3, 2009 as U.S. Publication No. 20090221571 and assigned to Merck and Co., Inc.

U.S. patent application Ser. No. 10/587,682, entitled "HIV INTEGRASE INHIBITORS" filed in the name of Wei Han, et al. on Mar. 9, 2005 and published on Aug. 2, 2007 as U.S. Publication No. 20070179196 and assigned to Merck and Co., Inc.

U.S. patent application Ser. No. 11/641,508, entitled "N-SUBSTITUTED HYDROXYPYRIMIDINONE CARBOXAMIDE INHIBITORS OF HIV INTEGRASE" filed in the name of Benedetta Crescenzi, et al. on Dec. 19, 2006 and published on May 31, 2007 as U.S. Publication No. 20070123524 and assigned to Merck and Co., Inc.

U.S. patent application Ser. No. 11/435,671, entitled "INTEGRASE INHIBITOR COMPOUNDS" filed in the name of Zhenhong R. Cai, et al. on May 16, 2006 and published on Mar. 29, 2007 as U.S. Publication No. 20070072831 and assigned to Gilead Sciences, Inc.

U.S. patent application Ser. No. 11/804,041, entitled "INTEGRASE INHIBITORS" filed in the name of Zhenhong R. Cai, et al. on May 16, 2007 and published on Mar. 6, 2008 as U.S. Publication No. 20080058315 and assigned to Gilead Sciences, Inc.

U.S. patent application Ser. No. 11/880,854, entitled "NOVEL HIV REVERSE TRANSCRIPTASE INHIBITORS" filed in the name of Hongyan Guo, et al. on Jul. 24, 2007 and published on Mar. 20, 2008 as U.S. Publication No. 20080070920 and assigned to Gilead Sciences, Inc.

U.S. patent application Ser. No. 10/585,504, entitled "PYRIMIDYL PHOSPHONATE ANTIVIRAL COMPOUNDS AND METHODS OF USE" filed in the name of Haolun Jin, et al. on Nov. 1, 2005 and published on Jun. 26, 2008 as U.S. Publication No. 20080153783 and assigned to Gilead Sciences, Inc.

U.S. patent application Ser. No. 11/579,772, entitled "HIV INTEGRASE INHIBITORS" filed in the name of John S. Wai, et al. on May 3, 2005 and published on Nov. 20, 2008 as U.S. Publication No. 20080287394 and assigned to Merck and Co., Inc.

U.S. patent application Ser. No. 10/591,914, entitled "HIV INTEGRASE INHIBITORS" filed in the name of Matthew M. Morrissette, et al. on Mar. 4, 2005 and published on Jun. 12, 2008 as U.S. Publication No. 20080139579 and assigned to Merck and Co., Inc.

U.S. patent application Ser. No. 11/629,153, entitled "HIV INTEGRASE INHIBITORS" filed in the name of John S. Wai, et al. on Jun. 3, 2005 and published on Jun. 18, 2008 as U.S. Publication No. 20080015187 and assigned to Merck and Co., Inc.

U.S. patent application Ser. No. 12/043,636, entitled "HIV INTEGRASE INHIBITORS, PHARMACEUTICAL COMPOSITIONS AND METHOD FOR THEIR USE" filed in the name of Qiyue Hu, et al. on Mar. 6, 2008 and published on Sep. 11, 2008 as U.S. Publication No. 20080221154 and assigned to Pfizer, Inc.

PCT WO 2007/019098, entitled "HIV INTEGRASE INHIBITORS," listing SmithKline Beecham Corporation, Shionogi & Co. Ltd., and Takashi Kawasuji as applicants, and Brian Johns as an inventor, published on Feb. 15, 2007.

U.S. patent application Ser. No. 12/306,198, entitled "MODULATORS OF PHARMACOKINETIC PROPERTIES OF THERAPEUTICS" filed in the name of Desai, Manoj C., et al. and was published on Nov. 26, 2009 as U.S. Publication No. 20090291952 and is assigned to Gilead Sciences, Inc.

U.S. patent application Ser. No. 12/274,107, entitled, "INTEGRASE INHIBITORS" filed Nov. 19, 2008 in the name of Jabri, Salman Y., et al. and was published on Nov. 26, 2009 as U.S. Publication No. 20090291921 and is assigned to Gilead Sciences, Inc.

U.S. patent application Ser. No. 12/215,605 "ANTIVIRAL COMPOUNDS" filed on Jun. 26, 2008 in the name of Cho, Aesop, et al., and was published on Oct. 15, 2009 as U.S. Publication No. 20090257978 and is assigned to Gilead Sciences, Inc.

U.S. patent application Ser. No. 12/097,859 METHODS FOR IMPROVING THE PHARMACOKINETICS OF HIV INTEGRASE INHIBITORS filed on Dec. 29, 2006 in the name of Kearney; Brian P., et al. and published on Sep. 17, 2009 as U.S. Publication No. 20090233964 and assigned to Gilead Sciences, Inc.

U.S. patent application Ser. No. 11/658,419, entitled "PHOSPHONATE ANALOGS OF HIV INHIBITOR COMPOUNDS" filed Jul. 26, 2005 in the name of Boojamra; Constantine G., et al. and was published on Aug. 13, 2009 as U.S. Publication No. 20090202470 and is assigned to Gilead Sciences, Inc.

U.S. patent application Ser. No. 12/215,601, entitled, "ANTIVIRAL COMPOUNDS" filed on Jun. 26, 2008 in the name of Cottell, Jeromy J., et al. and published on Jul. 23, 2009 as U.S. Publication No. 20090186869 and assigned to Gilead Sciences, Inc.

U.S. patent application Ser. No. 12/217,496 entitled "MODULATORS OF PHARMACOKINETIC PROPERTIES OF THERAPEUTICS" in the name of Desai, Manoj C., et al. and published on Jul. 16, 2009 as U.S. Publication No. 20090181902 and assigned to Gilead Sciences, Inc.

U.S. patent application Ser. No. 12/340,419 entitled "INHIBITORS OF CYTOCHROME P450" filed on Dec. 19, 2008 in the name of Desai, Manoj C. et al. and published on Jul. 9, 2009 as U.S. Publication No. 20090175820 and assigned to Gilead Sciences, Inc.

U.S. patent application Ser. No. 12/195,161 entitled "COMPOSITIONS AND METHODS FOR COMBINATION ANTIVIRAL THERAPY" filed on Aug. 20, 2008 in the name of Dahl, Terrence C. et al. and published on Jun. 4, 2009 as U.S. Publication No. 20090143314 and assigned to Gilead Sciences, Inc.

U.S. patent application Ser. No. 12/208,952 entitled "PROCESS AND INTERMEDIATES FOR PREPARING INTEGRASE INHIBITORS" filed on Sep. 11, 2008 in the name of Dowdy, Eric, et al. and published on Apr. 16, 2009 as U.S. Publication No. 20090099366 and assigned to Gilead Sciences, Inc.

U.S. patent application Ser. No. 12/147,220 entitled "THERAPEUTIC COMPOSITIONS AND METHODS" filed on Jun. 26, 2008 in the name of Kearney, Brian P. et al and published on Apr. 9, 2009 as U.S. Publication No. 20090093482 and assigned to Gilead Sciences, Inc.

U.S. patent application Ser. No. 12/147,041 entitled "THERAPEUTIC COMPOSITIONS AND METHODS" filed on Jun. 26, 2008 in the name of Kearney, Brian P. et al., published on Apr. 9, 2009 as U.S. Publication No. 20090093467 and assigned to Gilead Sciences, Inc.

U.S. patent application Ser. No. 12/215,266 entitled "ANTIVIRAL COMPOUNDS" filed on Jun. 26, 2008 in the name of Cai, Zhenhong R. et al., published Feb. 19, 2009 as U.S. Publication No. 20090047252 and assigned to Gilead Sciences, Inc.

U.S. patent application Ser. No. 12/204,174 entitled "COMPOSITIONS AND METHODS FOR COMBINATION ANTIVIRAL THERAPY" filed on Sep. 4, 2008 in the name of Dahl, Terrence C., et al., published on Feb. 5, 2009 as U.S. Publication No. 20090036408 and assigned to Gilead Sciences, Inc.

U.S. patent application Ser. No. 10/585,504 entitled "PYRIMIDYL PHOSPHONATE ANTIVIRAL COMPOUNDS AND METHODS OF USE" filed on Nov. 1, 2005 in the name of Jin, Haolun et al., published on Jun. 26, 2008 as U.S. Publication No. 20080153783 and assigned to Gilead Sciences, Inc.

U.S. patent application Ser. No. 11/853,606 entitled "PROCESS AND INTERMEDIATES FOR PREPARING INTEGRASE INHIBITORS" filed on Sep. 11, 2007 in the name of Dowdy, Eric, et al, published May 29, 2008 as U.S. Publication No. 20080125594 and assigned to Gilead Sciences, Inc.

U.S. patent application Ser. No. 11/644,811 entitled "PROCESSES AND INTERMEDIATES USEFUL FOR PREPARING INTEGRASE INHIBITOR COMPOUNDS" filed on Dec. 21, 2006 in the name of Evans, Jared W. et al., published on Feb. 14, 2008 as U.S. Publication No. 20080039487 and assigned to Gilead Sciences, Inc.

U.S. patent application Ser. No. 10/586,627 entitled "USE OF ADEFOVIR OR TENOFOVIR FOR INHIBITING MMTV-LIKE VIRUSES INVOLVED IN BREAST CANCER AND PRIMARY BILIARY CIRRHOSIS" filed on Jul. 20, 2007 in the name of Cihlar, Tomas, et al., published on Dec. 6, 2007 as U.S. Publication No. 20070281911 and assigned to Gilead Sciences, Inc.

U.S. patent application Ser. No. 11/435,671 entitled "INTEGRASE INHIBITOR COMPOUNDS" filed on May 16, 2006 in the name of Cai, Zhenhong R. et al., published on Mar. 29, 2007 as U.S. Publication No. 20070072831 and assigned to Gilead Sciences, Inc.

U.S. patent application Ser. No. 11/190,225 entitled "PHOSPHONATE ANALOGS OF HIV INHIBITOR COMPOUNDS" filed on Jul. 26, 2005 in the name of Boojamra, Constantine G. et al., published on Mar. 1, 2007 as U.S. Publication No. 20070049754 and assigned to Gilead Sciences, Inc.

U.S. patent application Ser. No. 10/511,182 entitled "NON NUCLEOSIDE REVERSE TRANSCRIPTASE INHIBITORS" filed on Feb. 28, 2005 in the name of Chen, James M. et al., published on Jun. 15, 2006 as U.S. Publication No. 20060128692 and assigned to Gilead Sciences, Inc.

U.S. patent application Ser. No. 11/033,422 entitled "PYRIMIDYL PHOSPHONATE ANTIVIRAL COMPOUNDS AND METHODS OF USE" filed on Jan. 11, 2005 in the name of Jin, Haolun et al., published on Dec. 22, 2005 as U.S. Publication No. 20050282839 and assigned to Gilead Sciences, Inc.

U.S. patent application Ser. No. 11/040,929 entitled "METHODS OF INHIBITION OF MMTV-LIKE VIRUSES" filed on Jan. 21, 2005 in the name of Cihlar, Tomas et al., published on Oct. 27, 2005 as U.S. Publication No. 20050239753 and assigned to Gilead Sciences, Inc.

U.S. patent application Ser. No. 10/423,496 entitled "CELLULAR ACCUMULATION OF PHOSPHONATE ANALOGS OF HIV PROTEASE INHIBITOR COMPOUNDS" filed on Apr. 25, 2003 in the name of Arimilli, Murty N. et al., published on Sep. 22, 2005 as U.S. Publication No. 20050209197 and assigned to Gilead Sciences, Inc.

U.S. patent application Ser. No. 10/424,130 entitled "NON NUCLEOSIDE REVERSE TRANSCRIPTASE INHIBITORS" filed on Apr. 25, 2003 in the name of Chen, James M. et al., published on Sep. 8, 2005 as U.S. Publication No. 20050197320 and assigned to Gilead Sciences, Inc.

U.S. patent application Ser. No. 10/944,118 entitled "AZA-QUINOLINOL PHOSPHONATE INTEGRASE INHIBITOR COMPOUNDS" filed on Sep. 17, 2004 in the name of Jin, Haolun et al., published on Jun. 23, 2005 as U.S. Publication No. 20050137199 and assigned to Gilead Sciences, Inc.

U.S. patent application Ser. No. 10/903,288 entitled "NUCLEOBASE PHOSPHONATE ANALOGS FOR ANTIVIRAL TREATMENT" filed on Jul. 30, 2004 in the name of Krawczyk, Steven H., published on Mar. 17, 2005 as U.S. Publication No. 20050059637 and assigned to Gilead Sciences, Inc.

U.S. patent application Ser. No. 10/757,141 entitled "COMPOSITIONS AND METHODS FOR COMBINATION ANTIVIRAL THERAPY" filed Jan. 13, 2004 Dahl, Terrance C. et al., published on Nov. 11, 2004 as U.S. Publication No. 20040224917 and assigned to Gilead Sciences, Inc.

U.S. patent application Ser. No. 10/757,122 entitled "COMPOSITIONS AND METHODS FOR COMBINATION ANTIVIRAL THERAPY" filed on Jan. 13, 2004 Dahl, Terrance C. et al., published on Nov. 11, 2004 as U.S. Publication No. 20040224916 and assigned to Gilead Sciences, Inc.

U.S. patent application Ser. No. 10/687,373 entitled "PRE-ORGANIZED TRICYCLIC INTEGRASE INHIBITOR COMPOUNDS" filed on Oct. 16, 2003 in the name of Chen, James M. et al., published on Aug. 26, 2004 as U.S. Publication No. 20040167124 and assigned to Gilead Sciences, Inc.

U.S. patent application Ser. No. 10/687,374 entitled "PRE-ORGANIZED TRICYCLIC INTEGRASE INHIBITOR COMPOUNDS" filed on Oct. 15, 2003 in the name of Chen, James M. et al., published on Aug. 12, 2004 as U.S. Publication No. 20040157804 and assigned to Gilead Sciences, Inc.

U.S. patent application Ser. No. 10/424,186 entitled "METHOD AND COMPOSITIONS FOR IDENTIFYING ANTI-HIV THERAPEUTIC COMPOUNDS" filed on Apr. 25, 2003 in the name of Birkus, Gabriel et al., published on Jun. 24, 2004 as U.S. Publication No. 20040121316 and assigned to Gilead Sciences, Inc.

U.S. patent application Ser. No. 11/820,444 entitled "DIKETO ACIDS WITH NUCLEOBASE SCAFFOLDS: ANTI-HIV REPLICATION INHIBITORS TARGETED AT HIV INTEGRASE" filed on Jun. 19, 2007 in the name of Nair, Vasu et al., published on Nov. 8, 2007 as U.S. Publication No. 20070259823 and assigned to the University of Georgia Research Foundation, Inc.

U.S. patent application Ser. No. 11/047,229 entitled "DIKETO ACIDS WITH NUCLEOBASE SCAFFOLDS: ANTI-HIV REPLICATION INHIBITORS TARGETED AT HIV INTEGRASE" filed on Jan. 31, 2005 in the name of Nair, Vasu et al., published on Aug. 3, 2006 as U.S. Publication No. 20060172973.

U.S. patent application Ser. No. 11/827,959 entitled "PYRIDINONE DIKETO ACIDS: INHIBITORS OF HIV REPLICATION" filed on Jul. 13, 2007 in the name of Nair, Vasu et al., published on Jan. 24, 2008 as U.S. Publication No. 20080020010 and assigned to the University of Georgia Research Foundation, Inc.

Additional integrase inhibitors include L-870,810 (Merck), INH-001 (Inhibitex), L870810 (Merck), PL-2500, composed of pryidoxal 1-5-phosphate derivatives (Procyon) monophores (Sunesis), V-165 (Rega Institute, Belgium), Mycelium integrasone (a fungal polyketide, Merck), GS 9224 (Gilead Sciences), AVX-I (Avexa), ITI-367, an oxadiazol pre-integrase inhibitor (George Washington University), GSK364735 (GSK/Shionogi), GS-9160 (GSK), S-1360 (Shionogi-GlaxoSmithKline Pharmaceuticals LLC), RSC 1838 (GSK/Shionogi), GS-9137 (taken alone or with Norvir) (Gilead), MK-2048 (Merck), S/GSK 1349572 and S/GSK 1265744 (no need for a PK booster) (GSK/Shionogi), 6-(3-chloro-2-fluorobenzyl)-1-[(2S)-1-hydroxy-3-methylbutan-2-y-1]-7-methoxy-4-oxo-1,4-dihydroquinoline-3-carboxylic acid (U.S. Patent Application Publication No. 20090018162), S-1360, L-870810, MK-0518 (Merck), C-2507 (Merck), BMS 538158 (Bristol Myers Squibb), and L-900564 (Merck).

The structure of L-900564 is shown below:

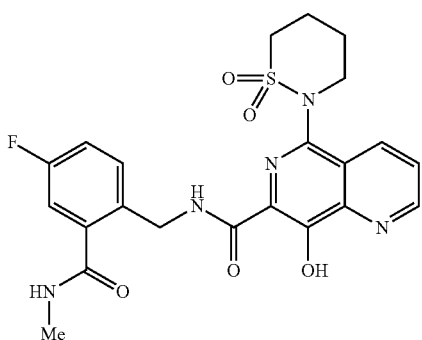 [SMILES: CNC(=O)c1cc(F)ccc1CNC(=O)c1nc(N2CCCCS2(=O)=O)c2cccnc2c1O]

Nair et al., J Med Chem. 2006 Jan. 26; 49(2): 445-447, discloses the following integrase inhibitors:

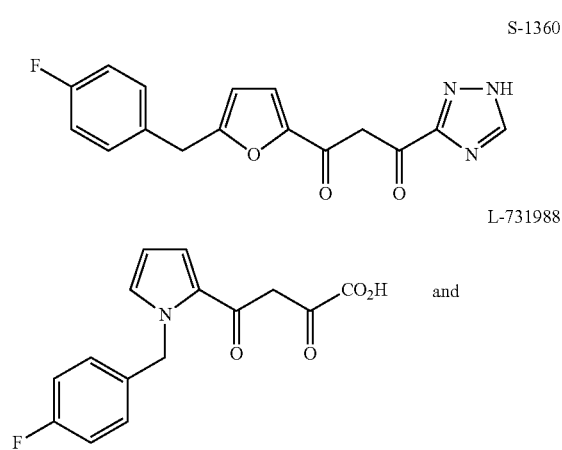

Additional integrase inhibitors are disclosed in Pais et al., J Med Chem. 2002 Jul. 18; 45(15):3184-94.

Several integrase inhibitors are peptides, including those disclosed in Divita et al., Antiviral Research, Volume 71, Issues 2-3, September 2006, Pages 260-267.

Another integrase inhibitor that can be used in the methods of treatment described herein include 118-D-24, which is disclosed, for example, in Vatakis, Journal of Virology, April 2009, p. 3374-3378, Vol. 83, No. 7.

Additional integrase inhibitors include those described in McKeel et al., "Dynamic Modulation of HIV-1 Integrase Structure and Function by Cellular LEDGF Protein, JBC Papers in Press. Published on Sep. 18, 2008 as Manuscript M805843200.

Other representative integrase inhibitors include dicaffeoylquinic acids (DCQAs), such as those disclosed in Zhu et al., "Irreversible Inhibition of Human Inununodeficiency Virus Type 1 Integrase by Dicaffeoylquinic Acids," *Journal of Virology*, April 1999, p. 3309-3316, Vol. 73, No. 4.

There are also various nucleoside compounds active as integrase inhibitors, including those disclosed in Mazumder, A., N. Neamati, J. P. Sommadossi, G. Gosselin, R. F. Schinazi, J. L. Imbach, and Y. Pommier. 1996. Effects of nucleotide analogues on human immunodeficiency virus type 1 integrase. Mol. Pharmacol. 49:621-628.

Protease Inhibitors

Protease inhibitors treat or prevent HIV infection by preventing viral replication. They act by inhibiting the activity of HIV protease, an enzyme that cleaves nascent proteins for final assembly of new virons. Examples are shown in the table that follows.

| Brand Name | Generic Name | Abbreviation | Experimental Code | Pharmaceutical Company |
|---|---|---|---|---|
| HIV Therapies: Protease Inhibitors (PIs) | | | | |
| Invirase ® | saquinavir (Hard Gel Cap) | SQV (HGC) | Ro-31-8959 | Hoffmann-La Roche |
| Fortovase ® | saquinavir (Soft Gel Cap) | SQV (SGC) | | Hoffmann-La Roche |
| Norvir ® | Ritonavir | RTV | ABT-538 | Abbott Laboratories |
| Crixivan ® | Indinavir | IDV | MK-639 | Merck & Co. |
| Viracept ® | Nelfinavir | NFV | AG-1343 | Pfizer |
| Agenerase ® | Amprenavir | APV | 141W94 or VX-478 | GlaxoSmithKline |
| Kaletra ® | lopinavir + ritonavir | LPV | ABT-378/r | Abbott Laboratories |
| Lexiva ® | fosamprenavir | | GW-433908 or VX-175 | GlaxoSmithKline |

-continued

| Brand Name | Generic Name | Abbreviation | Experimental Code | Pharmaceutical Company |
|---|---|---|---|---|
| Aptivus ® | tripanavir | TPV | PNU-140690 | Boehringer Ingelheim |
| Reyataz ® | atazanavir | | BMS-232632 | Bristol-Myers Squibb |
| | Brecanavir | | GW640385 | GlaxoSmithKline |
| Prezista ™ | Darunavir | | TMC114 | Tibotec |
| HTV Therapies: Other Classes of Drugs | | | | |
| Viread ™ | tenofovir disoproxil fumarate (DF) | TDF or Bis(POC) PMPA | | Gilead Sciences |
| Cellular Inhibitors | | | | |
| Droxia ® | Hydroxyurea | HU | | Bristol-Myers Squibb |
| HIV Therapies: Immune-Based Therapies | | | | |
| Proleukin ® | aldesleukin, or Interleukin-2 | IL-2 | | Chiron Corporation |
| Remune ® | HIV-1 Immunogen, or Salk vaccine | | AG1661 | The Immune Response Corporation |
| | | | HE2000 | HollisEden Pharmaceuticals |

III. Combination or Alternation HIV-Agents

In general, during alternation therapy, an effective dosage of each agent is administered serially, whereas in combination therapy, an effective dosage of two or more agents is administered together. In alternation therapy, for example, one or more first agents can be administered in an effective amount for an effective time period to treat the viral infection, and then one or more second agents substituted for those first agents in the therapy routine and likewise given in an effective amount for an effective time period.

The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Examples of suitable dosage ranges for anti-HIV compounds, including the JAK inhibitors described herein, can be found in the scientific literature and in the Physicians Desk Reference. Many examples of suitable dosage ranges for other compounds described herein are also found in public literature or can be identified using known procedures. These dosage ranges can be modified as desired to achieve a desired result.

Certain JAK inhibitors described herein are also inhibitors of CYP3A4, which means that they will significantly increase the $C_{max}$ plasma level of any anti-HIV drug that binds to CYP3A4, including HIV-1 protease inhibitors. This information can be taken into consideration when determining suitable dosages for such compounds.

IV. Combination Therapy for Treating an HCV Infection

Nonlimiting examples of additional agents include:

HCV Protease inhibitors: Examples include Medivir HCV Protease Inhibitor (HCV-PI or TMC435) (Medivir/Tibotec); MK-7009 (Merck), RG7227 (ITMN-191) (Roche/Pharmasset/InterMune), boceprevir (SCH 503034) (Schering), SCH 446211 (Schering), narlaprevir SCH900518 (Schering/Merck), ABT-450 (Abbott/Enanta), ACH-1625 (Achillion), BI 201335 (Boehringer Ingelheim), PHX1766 (Phenomix), VX-500 (Vertex) and telaprevir (VX-950) (Vertex). Further examples of protease inhibitors include substrate-based NS3 protease inhibitors (Attwood et al., Antiviral peptide derivatives, PCT WO 98/22496, 1998; Attwood et al, Antiviral Chemistry and Chemotherapy 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al, Biochemical and Biophysical Research Communications, 1997, 238, 643-647; Sudo K. et al., Antiviral Chemistry and Chemotherapy, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., Tetrahedron Letters 37:7229-7232, 1996).

SCH 351633, isolated from the fungus *Penicillium griseofulvum*, was identified as a protease inhibitor (Chu M., et al., Bioorganic and Medicinal Chemistry Letters 9: 1949-1952). Eglin c, isolated from leech, is a potent inhibitor of several serine proteases such as *S. griseus* proteases A and B, a-chymotrypsin, chymase and subtilisin. Qasim M. A. et al., Biochemistry 36: 1598-1607, 1997.

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et a; WO 02/008251 to Corvas International, Inc, and U.S. Pat. No. 7,169,760, US2005/176648, WO 02/08187 and WO 02/008256 to Schering Corporation.

HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838,475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208,600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995,174, WO 2004/032827 (Bristol-Myers Squibb), U.S. Pat. No. 7,041,698, WO 2004/043339 and U.S. Pat. No. 6,878,722 (Bristol-Myers Squibb).

Thiazolidine derivatives which show relevant inhibition in a reverse-phase HPLC assay with an NS3/4A fusion protein and NS5A/5B substrate (Sudo K. et al, Antiviral Research, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al, J. EBS Letters 421, 217-220; Takeshita N. et al, Analytical Biochemistry, 1997, 247, 242-246; A phenanthrenequinone possessing activity against protease in a SDS-PAGE and autoradiography assay isolated from the fermentation culture broth of Streptomyces sp., SCH 68631 (Chu M. et al, Tetrahedron Letters, 1996, 37, 7229-7232), and SCH 351633, isolated from the fungus Penicillium griseofulvum, which demonstrates activity in a scintillation proximity assay (Chu M. et al, Bioorganic and Medicinal Chemistry Letters 9, 1949-1952);

Helicase inhibitors (Diana G. D. et al, Compounds, compositions and methods for treatment of hepatitis C, U.S. Pat. No. 5,633,358; Diana G. D. et al, Piperidine derivatives, pharmaceutical compositions thereof and their use in the treatment of hepatitis C, PCT WO 97/36554);

HCV polymerase inhibitors, including nucleoside and non-nucleoside polymerase inhibors, such as ribavirin, viramidine, clemizole, filibuvir (PF-00868554), HCV POL, NM-283 (valopicitabine), MK-0608, 7-Fluoro-MK-0608, MK-3281, IDX-375, ABT-072, ABT-333, ANA598, BI 207127, GS 9190, PSI-6130, R1626, PSI-6206, PSI-35938, PSI-7851, PSI-7977, RG1479, RG7128, HCV-796 VCH-759 or VCH-916, and salts and prodrugs thereof.

Gliotoxin (Ferrari R. et al, Journal of Virology, 1999, 73, 1649-1654), and the natural product cerulenin (Lohmann V. et al., Virology, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and U.S. Patent Publication No. US 2004/0209831.

Antisense phosphorothioate oligodeoxynucleotides (S-ODN) complementary to sequence stretches in the 5' non-coding region (NCR) of the virus (Alt M. et al., Hepatology, 1995, 22, 1 O-717), or nucleotides 326-348 comprising the 3' end of the NCR and nucleotides 371-388 located in the core coding region of the HCV RNA (Alt M. et al, Archives of Virology, 1997, 142, 589-599; Galderisi U. et al, Journal of Cellular Physiology, 1999, 181, 251-257);

Inhibitors of IRES-dependent translation (Ikeda N et al., Agent for the prevention and treatment of hepatitis C, Japanese Patent Pub. JP-08268890; Kai Y. et al, Prevention and treatment of viral diseases, Japanese Patent Pub. JP-10101591);

HCV entry inhibitors, such as celgosivir (MK-3253) (MIGENIX Inc.), SP-30 (Samaritan Pharmaceuticals), ITX4520 (iTherX), ITX5061 (iTherX), PRO-206 (Progenies Pharmaceuticals) and other entry inhibitors by Progenies Pharmaceuticals, e.g., as disclosed in U.S. Patent Publication No. 2006/0198855.

Ribozymes, such as nuclease-resistant ribozymes (Maccjak, D. J. et al, Hepatology 1999, 30, abstract 995) and those disclosed in U.S. Pat. No. 6,043,077 to Barber et al, and U.S. Pat. Nos. 5,869,253 and 5,610,054 to Draper et al; and Nucleoside analogs have also been developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, 2004/002422, WO 2004/002999, WO 10/014134 and WO 11/123586.

Other patent applications disclosing the use of certain nucleoside analogs that can be used as second agents to treat hepatitis C virus include: PCT/CAOO/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; 6,846,810; 6,784,166 and 6,660,721 by Roche; PCT Publication Nos. WO 01/79246 (filed Apr. 13, 2001), WO 02/32920 (filed Oct. 18, 2001), WO 02/48165, WO 05/003147; US 2005/0009737; US 2005/0009737; 7,094,770, 6,927,291, WO 08/12163434, WO 10/077554, WO 09/152095, WO 10/075549, and WO 10/135569 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other miscellaneous compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S.

Pat. No. 5,725,859 to Omer et al., and U.S. Pat. No. 6,056,961), and piperidenes (U.S. Pat. No. 5,830,905 to Diana et al.).

Exemplary Additional Therapeutic Agents for Treatment of HCV

In one embodiment, one or more compounds provided herein can be administered in combination or alternation with an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b) and Pegasys® (pegylated interferon alfa-2a), optionally in further combination with ribavirin.

In one embodiment, the anti-hepatitis C virus interferon is infergen, IL-29 (PEG-Interferon lambda), R7025 (Maxy-alpha), Belerofon, Oral Interferon alpha, BLX-883 (Locteron), omega interferon, multiferon, medusa interferon, Albuferon or REBIF©.

In one embodiment, one or more compounds provided herein can be administered in combination or alternation with an anti-hepatitis C virus polymerase inhibitor, such as ribavirin, viramidine, HCV POL, NM-283 (valopicitabine), PSI-7977, PSI-938, MK-0608, 7-Fluoro-MK-0608, PSI-6130, R1626, IDX-184, INX-189, PSI-6206, PSI-35938, R1479, HCV-796 or R7128.

In one embodiment, one or more compounds provided herein can be administered in combination or alternation with an anti-HCV protease inhibitor such as ITMN-191, SCH 503034, VX950 (telaprevir), GNS-227, or Medivir HCV Protease Inhibitor.

In one embodiment, one or more compounds provided herein can be administered in combination or alternation with an anti-HCV vaccine, such as TG4040, PeviPRO™, CGI-5005, HCV/MF59, GV1001, IC41 or INNO0101 (E1).

In one embodiment, one or more compounds provided herein can be administered in combination or alternation with an anti-HCV monoclonal antibody, such as AB68 or XTL-6865 (formerly HepX-C); or an anti-hepatitis C virus polyclonal antibody, such as cicavir.

In one embodiment, one or more compounds provided herein can be administered in combination or alternation with an anti-hepatitis C virus immunomodulator, such as Zadaxin® (thymalfasin), NOV-205 or Oglufanide.

In one embodiment, one or more compounds provided herein can be administered in combination or alternation with Nexavar, doxorubicin, PI-88, amantadine, JBK-122, VGX-4 IOC, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

Prodrug Forms

The 5'-hydroxyl moiety in the nucleosides described herein, and hydroxy groups on the JAK inhibitors described herein, can be modified to be in prodrug form. For example, the 5'-hydroxy in nucleosides can be replaced with a 5'-OR$^1$ moiety, where R$^1$ is an optionally substituted alkyl, an optionally substituted cycloalkyl, an optionally substituted aralkyl, dialkylaminoalkylene, alkyl-C(=O)—, aryl-C(=O)—, alkoxyalkyl-C(=O)—, aryloxyalkyl-C(=O)—, alkylsulfonyl, arylsulfonyl, aralkylsulfonyl, an —O-linked amino acid, diphosphate, triphosphate or derivatives thereof, or

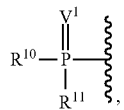

wherein:

V$^1$ is O or S;

R$^{10}$ is selected from O$^-$, —OH, an optionally substituted aryloxy or heteroaryl-oxy-, alkyl-C(=O)—O—CH$_2$—O—, alkyl-C(=O)—S—CH$_2$CH$_2$—O—, pivaloyloxymethyl, —NH—CH$_2$-aryl, —O—CH$_2$—O—C(O)—OR$^{a1}$, an —N-linked amino acid, an —N-linked amino acid ester,

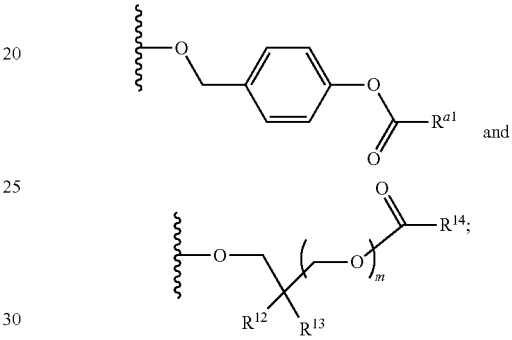

or OR$^1$ can be

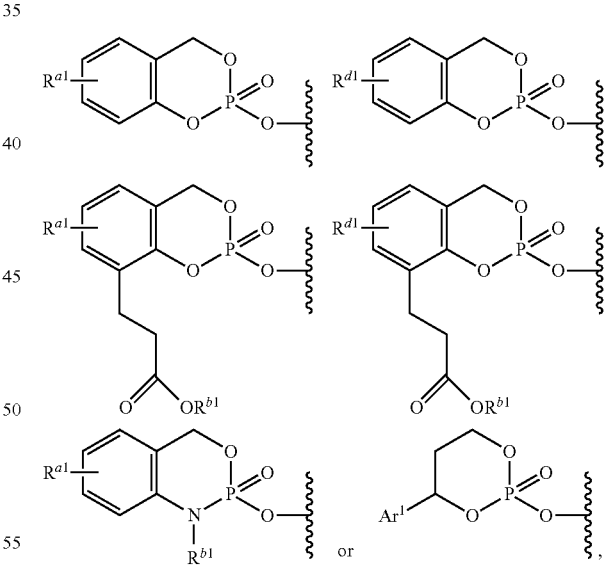

where Ar$^1$ is selected from phenyl, pyridinyl, monocyclic heteroaryl, substituted phenyl with 1-3 substituents, and monoheterocyclic heteroaryl with 1-2 substitutents, wherein each substituent is independently selected from the group consisting of —F, —Cl, —Br, —I, C$_{1-6}$ alkyl, —CF$_3$, —OMe, —NMe$_2$, —OEt, —CO$_2$R$^{a1}$, —CONH$_2$, —SMe, —S(=O)$_2$Me, —S(=O)$_2$NH$_2$, and CN;

or R$^1$ and R$^{10}$ can combine to form a cyclic phosphate of the formula:

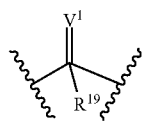

where $R^{19}$ is selected from N-linked amino acid ester, $OR^{a1}$ or $OR^{20}$, wherein $R^{20}$ is substituted aryl with 1-3 substituents, or substituted heteroaryl with 1-2 substituents, wherein each substituent is independently selected from $R^{a1}$ and $R^{d1}$.

$R^{11}$ is selected from $O^-$, —OH, an optionally substituted aryloxy or aryl-O—, alkyl-C(=O)O—CH$_2$O—, alkyl-C(=O)—S—CH$_2$CH$_2$O—, pivaloyloxymethyl, —NH—CH$_2$-aryl, —O—CH$_2$—O—C(O)—$OR^{a1}$, an —N-linked amino acid, an —N-linked amino acid ester,

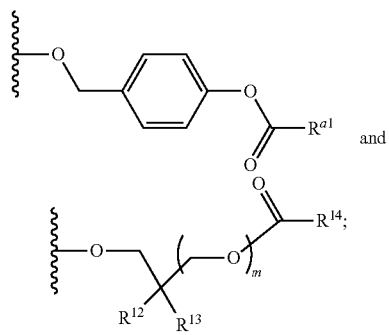

or $OR^1$ can be

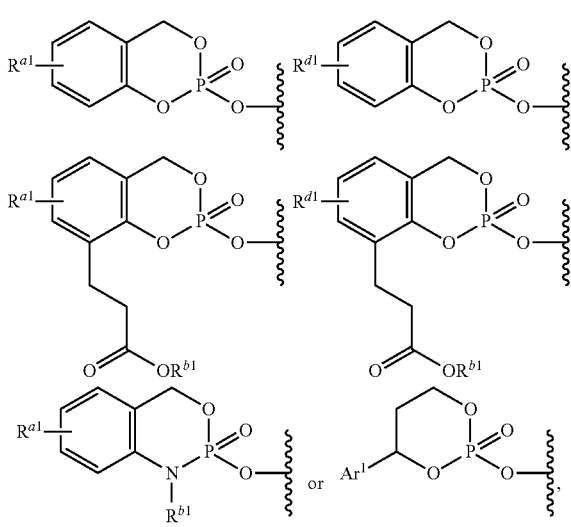

where $Ar^1$ is selected from phenyl, pyridinyl, monocyclic heteroaryl, substituted phenyl with 1-3 substituents, and monoheterocyclic heteroaryl with 1-2 substitutents, wherein each substituent is independently selected from the group consisting of —F, —Cl, —Br, —I, $C_{1-6}$ alkyl, —CF$_3$, —OMe, —NMe$_2$, —OEt, —CO$_2R^{a1}$, —CONH$_2$, —SMe, —S(=O)$_2$Me, —S(=O)$_2$NH$_2$, and CN;

or $R^1$ and $R^{10}$ can combine to form a cyclic phosphate of the formula:

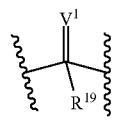

where $R^{19}$ is selected from N-linked amino acid ester, $OR^{a1}$ or $OR^{20}$, wherein $R^{20}$ is substituted aryl with 1-3 substituents, or substituted heteroaryl with 1-2 substituents, wherein each substituent is independently selected from $R^{a1}$ and $R^{d1}$, each $R^{12}$ and $R^{13}$ are, independently, —C≡N or an optionally substituted substituent selected from $C_{1-8}$ organylcarbonyl, $C_{1-8}$ alkoxycarbonyl and $C_{1-8}$ organylaminocarbonyl;

each $R^{14}$ is hydrogen or an optionally substituted $C_{1-6}$ alkyl;

each m is independently 1 or 2, and if both $R^{10}$ and $R^{11}$ are

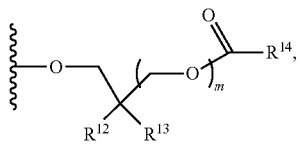

each $R^{12}$, each $R^{13}$, each $R^{14}$ and each m can be the same or different.

$R^{a1}$, $R^{b1}$, $R^{c1}$ and $R^{d1}$ are each independently selected from hydrogen, an optionally substituted alkyl, an optionally substituted alkenyl, an optionally substituted alkynyl, an optionally substituted aryl, an optionally substituted heteroaryl, an optionally substituted aralkyl and an optionally substituted heteroaryl-($C_{1-6}$ alkyl).

In one embodiment, $R^1$ is a mono-phosphate, di-phosphate, tri-phosphate, or phosphate prodrug.

V. Pharmaceutical Compositions

Humans suffering from effects caused by any of the diseases described herein, and in particular, HIV infection, can be treated by administering to the patient an effective amount of the compositions described above, in the presence of a pharmaceutically acceptable carrier or diluent, for any of the indications or modes of administration as described in detail herein. The active materials can be administered by any appropriate route, for example, orally, parenterally, enterally, intravenously, intradermally, subcutaneously, transdermally, intranasally or topically, in liquid or solid form.

The active compounds are included in the pharmaceutically acceptable carrier or diluent in an amount sufficient to deliver to a patient a therapeutically effective amount of compound to inhibit viral propagation in vivo, especially HIV propagation, without causing serious toxic effects in the treated patient. While not wishing to be bound to a particular theory, it is believed that the JAK inhibitors render the cellular milieu non-supportive of productive replication. By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside or other agent to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3,000 mg, preferably 70 to 1,400 mg of active ingredient per unit dosage form. An oral dosage of 50 to 1,000 mg is usually convenient.

Ideally, the active ingredient should be administered to achieve peak plasma concentrations of the active compound of from about 0.02 to 70 micromolar, preferably about 0.5 to 10 micromolar. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers, these may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

In one embodiment, the composition is a co-formulated pill, tablet, or other oral drug delivery vehicle including one or more of the JAK inhibitors described herein, and optionally including one or more additional antiviral agents.

In another embodiment, the JAK inhibitors described herein are co-formulated with ATRIPLA® (efavirenz 600 mg/emtricitabine [(−)-FTC] 200 mg/tenofovir disoproxil fumarate 300 mg), and, optionally, with a thymidine nRTI such as AZT and a guanine nRTI (or a compound such as DAPD which is deaminated in vivo to form a guanine nRTI, in this case, DXG). Because efavirenz is an NNRTI, tenofovir is an adenine nRTI, (−)-FTC is a cytosine nRTI, and AZT is a thymidine nRTI, and DAPD is deaminated in vivo to form DXG (a guanine NRTI), the combination of the coformulated compounds will provide, in addition to the JAK inhibitors, all four bases (ACTG) plus an additional agent capable of interacting with HIV in a different mechanism.

Controlled Release Formulations

All of the U.S. patents cited in this section on controlled release formulations are incorporated by reference in their entirety.

The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer the combination of the thymidine and non-thymidine nucleoside antiviral agents, or prodrugs thereof. U.S. Pat. No. 5,749,847 discloses a method for the delivery of nucleotides into organisms by electrophoration. U.S. Pat. No. 5,718,921 discloses microspheres comprising polymer and drug dispersed there within. U.S. Pat. No. 5,629,009 discloses a delivery system for the controlled release of bioactive factors. U.S. Pat. No. 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase which comprises the active drug, its salt or prodrug, in admixture with a hydrogel forming agent, and an external phase which comprises a coating which resists dissolution in the stomach. U.S. Pat. Nos. 5,736,159 and 5,558,879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

Prodrug Formulations

The JAK inhibitors, as well as the nucleosides or other compounds which are described herein for use in combination or alternation therapy with the JAK inhibitors or their related compounds, can be administered as an acylated prodrug or a nucleotide prodrug, as described in detail below.

Any of the JAK inhibitors, nucleosides, or other compounds described herein that contain a hydroxyl or amine function can be administered as a nucleotide prodrug to increase the activity, bioavailability, stability or otherwise alter the properties of the nucleoside. A number of nucleotide prodrug ligands are known. In general, alkylation, acylation or other lipophilic modification of the hydroxyl group of the compound or of the mono, di or triphosphate of the nucleoside will increase the stability of the nucleotide. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, Antiviral Research, 27 (1995) 1 17. Any of these can be used in combination with the disclosed nucleosides or other compounds to achieve a desire effect.

The active nucleoside or other hydroxyl containing compound can also be provided as an ether lipid (and particularly a 5'-ether lipid for a nucleoside), as disclosed in the following references, Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res. Hum. Retroviruses. 6:491 501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." J. Med. Chem. 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." Antimicrob. Agents Chemother. 36:2025.2029; Hostetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." J. Biol. Chem. 265:61127.

Nonlimiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et-al.), Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." Cancer Res. 33, 2816 2820; Holy, A. (1993) Isopolar phosphorous-modified nucleotide analogues," In: De Clercq (Ed.), Advances in Antiviral Drug Design, Vol. I, JAI Press, pp. 179 231; Hong, C. I., Nechaev, A., and West, C. R. (1979a) "Synthesis and antitumor activity of 1β-D-arabino-furanosylcytosine conjugates of cortisol and cortisone." Biochem. Biophys. Rs. Connun. 88, 1223 1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(Q-D-arabinofuranosyl)cytosine conjugates of corticosteroids and selected lipophilic alcohols." J. Med. Chem. 28, 171 177; Hosteller, K. Y., Stuhmiller, L. M., Lenting, H. B. M. van den Bosch, H. and Richman J Biol. Chem. 265, 6112 6117; Hosteller, K. Y., Carson, D. A. and Richman, D. D. (1991); "Phosphatidylazidothymidine: mechanism of antiretroviral action in CEM cells." J. Biol Chem. 266, 11714 11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." Antiviral Res. 24, 59 67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." Antimicrobial Agents Chemother. 38, 2792 2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." J. Med. Chem. 27,440 444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." J. Med. Chem. 33 2264 2270; Jones, A. S., McGuigan, C., Walker, R. T., Balzarini, J. and DeClercq, E. (1984) "Synthesis, properties, and biological activity of some nucleoside cyclic phosphoramidates." J. Chem. Soc. Perkin Trans. I, 1471 1474; Juodka, B. A. and Smart, J. (1974) "Synthesis of diribonucleoside phosph (P.fwdarw.N) amino acid derivatives." Coll. Czech. Chem. Comm. 39, 363 968; Kataoka, S., Imai, J., Yamaji, N., Kato, M., Saito, M., Kawada, T. and Imai, S. (1989) "Alkylated cAMP derivatives; selective synthesis and biological activities." Nucleic Acids Res. Sym. Ser. 21, 1 2; Kataoka, S., Uchida, "(cAMP) benzyl and methyl triesters." Heterocycles 32, 1351 1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivatives against HIV and ULV in vitro." Antiviral Chem. Chemother. 3, 107 112; Kodama, K., Morozumi, M., Saithoh, K. T., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-Darabinofuranosylcytosine." Jpn. J. Cancer Res. 80, 679 685; Korty, M. and Engels, J. (1979) "The effects of adenosine- and guanosine 3',5' phosphoric and acid benzyl esters on guinea-pig ventricular myocardium." Naunyn-Schmiedeberg's Arch. Pharmacol. 310, 103 111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." J. Med. Chem, 33, 2368 2375; LeBec, C., and Huynh-Dinh, T. (1991) "Synthesis of lipophilic phosphate triester derivatives of 5-fluorouridine an arabinocytidine as anticancer prodrugs." Tetrahedron Lett. 32, 6553 6556; Lichtenstein, J., Barner, H. D. and Cohen, S. S. (1960) "The metabolism of exogenously supplied nucleotides by *Escherichia coli*.," J. Biol. Chem. 235, 457 465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". Mitt. Geg. Lebensmittelunters. Hyg. 72, 131 133 (Chem. Abstr. 95, 127093); McGigan, C. Tollerfield, S. M. and Riley, P. a. (1989) "Synthesis and biological evaluation of some phosphate triester derivatives of the anti-viral drug Ara." Nucleic Acids Res. 17, 6065 6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107 113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." Antiviral Chem. Chemother. 1, 355 360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." Antiviral Chem. Chemother. 1, 25 33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." Antiviral Res. 15, 255 263; McGuigan, C., Pathirana, R. N., Balzarini, J. and DeClercq, E. (1993b) "Intracellular delivery of bioactive AZT nucleotides by aryl phosphate derivatives of AZT." J. Med. Chem. 36, 1048 1052.

Alkyl hydrogen phosphate derivatives of the anti-HIV agent AZT may be less toxic than the parent nucleoside analogue. Antiviral Chem. Chemother. 5, 271 277; Meyer, R. B., Jr., Shuman, D. A. and Robins, R. K. (1973) "Synthesis of purine nucleoside 3',5'-cyclic phosphoramidates." Tetrahedron Lett. 269 272; Nagyvary, J. Gohil, R. N., Kirchner, C. R. and Stevens, J. D. (1973) "Studies on neutral esters of cyclic AMP," Biochem. Biophys. Res. Commun. 55, 1072 1077; Namane, A. Gouyette, C., Fillion, M. P., Fillion, G. and Huynh-Dinh, T. (1992) "Improved brain delivery of AZT using a glycosyl phosphotriester prodrug." J. Med. Chem. 35, 3039 3044; Nargeot, J. Nerbonne, J. M. Engels, J. and Leser, H. A. (1983) Natl. Acad. Sci. U.S.A. 80, 2395 2399; Nelson, K. A., Bentrude, W. G. Stser, W. N. and Hutchinson, J. P. (1987) "The question of chair-twist equilibria for the phosphate rings of nucleoside cyclic 3',5'-monophosphates. $^1$HNMR and x-ray crystallographic study of the diastereomers of thymidine phenyl cyclic 3',5'-monophosphate." J. Am. Chem. Soc. 109, 4058 4064; Nerbonne, J. M., Richard, S., Nargeot, J. and Lester, H. A. (1984) "New photoactivatable cyclic nucleotides produce intracellular jumps in cyclic AMP and cyclic GMP concentrations." Nature 301, 74 76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." J. Am. Chem. Soc. 111, 4270 4277; Ohno, R., Tatsunii, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine-5' stearylphosphate." Oncology 48, 451 455. Palomino, E., Kessle, D. and Horwitz, J. P. (1989) "A dihydropyridine carrier system for sustained delivery of 2',3' dideoxynucleosides to the brain." J. Med. Chem. 32, 22 625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." Antiviral Res. 20 (Suppl. 1). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." J. Med. Chem. 34, 1408 1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the on-line ISRP-cleaning HPLC technique." Antiviral Chem Chemother. 5, 91 98; Postemark, T. (1974) "Cyclic AMP and cyclic GMP." Annu. Rev. Pharmacol. 14, 23 33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1, 3-dihydroxy-2-propoxy)methyl]guanine." J. Med. Chem. 29, 671 675; Pucch, F., Gosselin, G., Lefebvre, I., Pompon, a., Aubertin, A. M. Dim, and Imbach, J. L. (1993) "Intracellular delivery of nucleoside monophosphate through a reductase-mediated activation process." Antiviral Res. 22, 155 174; Pugaeva, V. P., Klochkeva, S. I., Mashbits, F. D. and Eizengart, R. S. (1969). "Toxicological assessment and health standard ratings for ethylene sulfide in the industrial atmosphere." Gig. Trf. Prof. Zabol. 14, 47 48 (Chem. Abstr. 72, 212); Robins, R. K. (1984) "The potential of nucleotide analogs as inhibitors of Retro viruses and tumors." Pharm. Res. 11 18; Rosowsky, A., Kim. S. H., Ross and J. Wick, M. M. (1982) "Lipophilic 5'-(alkylphosphate) esters of 1-β-D-arabinofiiranosylcytosine and its $N^4$-acyl and 2,2'-anhydro-3'-O-acyl derivatives as potential prodrugs." J. Med. Chem. 25, 171 178; Ross, W. (1961) "Increased sensitivity of the walker turnout towards aromatic nitrogen mustards carrying basic side chains following glucose pretreatment." Biochem. Pharm. 8, 235 240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-Q-D-arabinofuranosylcytosine 5'diphosphate [–], 2-diacylglycerols." J. Med. Chem. 25, 1322 1329; Saffhill, R. and Hume, W. J. (1986) "The degradation of 5-iododeoxyuridine and 5-bromoethoxyuridine by serum from different sources and its consequences for the use of these compounds for incorporation into DNA." Chem. Biol. Interact. 57, 347 355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." Chem Pharm. Bull. 28, 2915 2923; Sastry, J. K., Nehete, P. N., Khan, S., Nowak, B. J., Plunkett, W., Arlinghaus, R. B. and Farquhar, D. (1 992) "Membrane-permeable dideoxyuridine 5'-monophosphate analogue inhibits human immunodeficiency virus infection." Mol. Pharmacol. 41, 441 445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." 9th Annual AAPS Meeting. San Diego, Calif. (Abstract). Shuto, S., Ueda, S., Imamura, S., Fukukawa, K. Matsuda, A. and Ueda, T. (1987) "A facile one-step synthesis of 5' phosphatidiylnucleosides by an enzymatic two-phase reaction." Tetrahedron Lett. 28, 199 202; Shuto, S. Itoh, H., Ueda, S., Imamura, S., Kukukawa, K., Tsujino, M., Matsuda, A. and Ueda, T. (1988) Pharm. Bull. 36, 209 217. An example of a useful phosphate prodrug group is the S-acyl-2-thioethyl group, also referred to as "SATE".

VI. Methods of Treatment

The compositions described herein can be used to treat patients infected with HIV-1 and HIV-2, to prevent an infection by HIV-1 and HIV-2, or to eradicate an HIV-1 or HIV-2 infection.

When the treatment involves co-administration of the JAK inhibitors described herein and nucleoside antiviral agents and/or non-thymidine nucleoside antiviral agents, the HIV-1 or HIV-2 may already have developed one or more mutations, such as the M184V, K65R mutation or TAMS. In such a case, the second agent will ideally be selected to be active against HIV-1 or HIV-2 that has these mutations. Methods for selecting appropriate antiretroviral therapy for patients with various mutations in their HIV-1 or HIV-2 are known to those of skill in the art.

When the treatment involves the co-administration of an adenine, cytosine, thymidine, and guanine nucleoside antiviral agent, as well as the additional antiviral agent(s), ideally the administration is to a patient who has not yet developed any resistance to these antiviral agents or has been off therapy for at least three months. In that case, it may be possible to actually cure an infected patient if the therapy can treat substantially all of the virus, substantially everywhere it resides in the patient. However, even in the case of infection by a resistant virus, the combination therapy should be effective against all known resistant viral strains, because there is at least one agent capable of inhibiting such a virus in this combination therapy, and because the JAK inhibitors do not function in the same manner as the conventional NRTI, NNRTI, protease inhibitors, entry inhibitors, integrase inhibitors, and the like, and thus remain effective against strains that have mutated following exposure to these agents.

The compounds can be used in different ways to treat or prevent HIV, and, in one embodiment, to cure an HIV infection. In one embodiment, a combination of a JAK inhibitor as described herein, a macrophage depleting agent (e.g., clodronate-loaded liposomes, gadolinium chloride (GdCl)), plus HAART therapy is used. The strategy involves reducing viral loads with traditional HAART and JAK inhibitor therapy. Then, macrophages are systemically depleted (typically without discrimination for infected versus infected macrophages). HAART and JAK inhibitor therapy would be maintained during macrophage depletion. Then, treatment with the macrophage depleting agent is withdrawn, while treatment with HAART and the JAK inhibitor is maintained.

In one aspect of this embodiment, HAART is then withdrawn, while JAK inhibitor therapy is maintained, optionally while monitoring viral rebound.

In another aspect of this embodiment, both HAART and JAK inhibitor therapy are then withdrawn, optionally while monitoring viral rebound.

In another embodiment, viral loads are reduced with traditional HAART+JAK inhibitors, specifically one or both of Tofacitinib and Jakafi, as described herein. Then, macrophages are systemically depleted (typically without discrimination for infected versus infected macrophages) with Boniva or Fosamax (both of these drugs are potent macrophage depleting agents). HAART+JAK inhibitor therapy is maintained during macrophage depletion. Then, treatment with the macrophage depleting agent is withdrawn, while treatment with HAART and the JAK inhibitor is maintained.

In one aspect of this embodiment, HAART is then withdrawn, while JAK inhibitor therapy with one or both of Tofacitinib and Jakafi is maintained, optionally while monitoring viral rebound.

In another aspect of this embodiment, both HAART and JAK inhibitor therapy with one or both of Tofacitinib and Jakafi are then withdrawn, optionally while monitoring viral rebound.

In another embodiment, a combination of a histone deacetylase inhibitor (HDAC inhibitor) or interleukin 7 (IL-7) and HAART and a JAK inhibitor is used. One limitation associated with treating HIV is that while it is not fully understood how HIV-1 evades the immune response and establishes latency in resting cells, it is believed that a variety of signalling molecules and transcription factors appear to play a role, and thus offer potential targets for intervention. Thus, in this embodiment, IL-7 is used to confer reactivation of resting cells, effectively flushing HIV-1 out of hiding, and histone deacetylase (HDAC) inhibitors are used to confer reactivation by up regulation of pro-HIV genes, effectively coaxing virus out from previously resting cells. In this manner, latent HIV is eradicated. An example of a reactivation agent that could be used in this manner is panobinostate, which is described, for example, in Lewin, et al., "HIV cure and eradication: how will we get from the laboratory to effective clinical trials?" AIDS:24 Apr. 2011. Representative HDAC inhibitors include Vorinostat, Romidepsin (trade name Istodax), Panobinostat (LBH589), Valproic acid (including Mg valproate and other salt forms), Belinostat (PXD101), Mocetinostat (MGCD0103), PCI-24781, Entinostat (MS-275), SB939, Resminostat (4SC-201), Givinostat (ITF2357), CUDC-101, AR-42, CHR-2845, CHR-3996, 4SC-202, sulforaphane, suberoylanilide hydroxamic acid (SAHA), BML-210, M344, CI-994; CI-994 (Tacedinaline); BML-210; M344; MGCDO103 (Mocetinostat); and Tubastatin A. Additional HDAC inhibitors are described in U.S. Pat. No. 7,399,787.

The strategy involves reducing viral loads with traditional HAART and JAK inhibitor therapy. Then, the patient is treated with a reactivation agent (as defined in Lewin et al., supra), such as panobinostat.

In one aspect of this embodiment, both HAART and JAK inhibitor therapy are maintained during reactivation, and in another aspect of this embodiment, HAART, but not JAK inhibitor therapy, is maintained during reactivation.

Treatment with the reactivation agent is then withdrawn, while continuing treatment with HAART and one or more JAK inhibitors, such as Tofacitinib and Jakafi as defined herein.

In one aspect of this embodiment, HAART is then withdrawn, while JAK inhibitor therapy is maintained, optionally while monitoring viral rebound.

In another aspect of this embodiment, both HAART and JAK inhibitor therapy are then withdrawn, optionally while monitoring viral rebound.

In another embodiment, the JAK inhibitors are administered to a patient before, during, or after administration of a vaccine and/or an immunostimulant. The use of immunostimulants can provide an optimal antiretroviral regimen. The immunostimulatory treatments include, but are not limited to, therapies from two functional classes: 1) agents that target actively replicating cells and 2) agents activating latently infected cells.

In addition to the JAK inhibitors and immunomodulatory agents, HAART can also be provided. The JAK inhibitors, optionally with co-administered HAART, can suppress virus to undetectable or virtually undetectable levels. The addition of an immunomodulatory therapy that specifically targets viral reservoirs can, ideally, lead to a cure, or at least remove virus from one or more viral reservoirs.

Immunostimulants

The term "immunostimulant" is used herein to describe a substance which evokes, increases and/or prolongs an immune response to an antigen. While the present application distinguishes between an "antigen" and an "immunostimulant" it should be noted that this is merely for reasons of clarity and ease of description. It should be understood that the immunostimulant could have, and in many cases preferably has, antigenic potential itself.

Immunomodulatory agents modulate the immune system, and, as used herein, immunostimulants are also referred to as immunomodulatory agents, where it is understood that the desired modulation is to stimulate the immune system.

There are two main categories of immunostimulants, specific and non-specific. Specific immunostimulants provide antigenic specificity in immune response, such as vaccines or any antigen, and non-specific immunostimulants act irrespective of antigenic specificity to augment immune response of other antigen or stimulate components of the immune system without antigenic specificity, such as adjuvants and non-specific immunostimulators.

Examples of immunostimulants include levamisole, thalidomide, erythema nodosum leprosum, BCG, cytokines such as interleukins or interferons, including recombinant cytokines and interleukin 2 (aldeslukin), 3D-MPL, QS21, CpG ODN 7909, miltefosine, anti-PD-1 or PD-1 targeting drugs, and acid (DCA, a macrophage stimulator), imiquimod and resiquimod (which activate immune cells through the toll-like receptor 7), chlorooxygen compounds such as tetrachlorodecaoxide (TCDO), agonistic CD40 antibodies, soluble CD40L, 4-1BB:4-1BBL agonists, OX40 agonists, TLR agonists, moieties that deplete regulatory T cells, arabinitol-ceramide, glycerol-ceramide, 6-deoxy and 6-sulfono-myo-insitolceramide, iNKT agonists, TLR agonists.

WF 10 [Immunokine, Macrokine] is a 1:10 dilution of tetrachlorodecaoxide (TCDO) formulated for intravenous injection. WF 10 specifically targets macrophages, and modulates disease-related up-regulation of immune responses in vivo. 3D-MPL is an immunostimulant derived from the lipopolysaccharide (LPS) of the Gram-negative bacterium *Salmonella minnesota*. MPL has been deacylated and is lacking a phosphate group on the lipid A moiety. This chemical treatment dramatically reduces toxicity while preserving the immunostimulant properties (Ribi, 1986). Ribi Immunochemistry produces and supplies MPL to GSK-Biologicals.

QS21: is a natural saponin molecule extracted from the bark of the South American tree *Quillaja saponaria* Molina. A purification technique developed to separate the individual saponins from the crude extracts of the bark, permitted the isolation of the particular saponin, QS21, which is a triterpene glycoside demonstrating stronger adjuvant activity and lower toxicity as compared with the parent component. QS21 has been shown to activate MHC class I restricted CTLs to several subunit Ags, as well as to stimulate Ag specific lymphocytic proliferation (Kensil, 1992). Aquila (formally Cambridge Biotech Corporation) produces and supplies QS21 to GSK-Biologicals.

CpG ODN 7909 is a synthetic single-stranded phosphorothioate oligodeoxynucleotide (ODN) of 24 bases length. Its base sequence, which is 5'-TCGTCGTTTTG-TCGTTTTGTCGTT-3', has been optimized for stimulation of the human immune system. CpG DNA or synthetic ODN containing CpG motifs are known to activate dendritic cells, monocytes and macrophages to secrete TH1-like cytokines and to induce TH1 T cell responses including the generation of cytolytic T cells, stimulate NK cells to secrete IFNg and increase their lytic activity, they also activate B cells to proliferate (Krieg A et al. 1995 Nature 374: 546, Chu R et al. 1997 J. Exp. Med. 186: 1623). CpG 7909 is not antisense to any known sequence of the human genome. CpG 7909 is a proprietary adjuvant developed by and produced on behalf of Coley Pharmaceutical Group, Inc., Mass., US.

iNKT Agonists

A subset of T cells known as iNKT (invariant natural killer T) cells are defined by their expression of a restricted TCR repertoire, consisting of a canonical V-alpha-4-J-alpha-18 or V-alpha-24-J-alpha-8-alpha chain in mice and humans respectively. iNKT cells recognize and become activated in response to self or foreign antigenic lipids presented by non-polymorphic CD1d molecules expressed on the surface of APCs. iNKT cells are activated in response to a variety of infections, and during inflammatory and autoimmune diseases. iNKT cells provide a means of linking and coordinating innate and adaptive immune responses, as their stimulation can induce the downstream activation of DCs, NK cells, B and T cells. It has been demonstrated in vitro that iNKT cells stimulate B cell proliferation and antibody production.

NKT cells can be activated by alpha-galactosyl-ceramide (alpha-GalCer) or its synthetic analog KRN 7000 (U.S. 2003/0157135). Alpha-GalCer can stimulate NK activity and cytokine production by NKT cells (U.S. 2003/0157135). Alpha-GalCer and related glycosylceramides not only function as antigens, but can also be used as soluble adjuvants capable of enhancing and/or extending the duration of the protective immune responses induced by other antigens.

Thus, in some embodiments of the present invention the immunostimulant may be an iNKT cell agonist. The agonist may be an exogenous or endogenous agonist. It may be a glycosidic agonist (such as alpha-galactasylceramide) or a non-glycosidic agonist (such as threitolceramide).

Imunostimulatory Lipids or Glycolipids

In some embodiments, the immunostimulant may be a lipid or a glycolipid. Glycolipids presented by CD1 can be grouped into different classes including for example diacylglycerolipids, sphingolipids, mycolates and phosphomycoketides (Zajonc and Krenenberg, Current Opinion in Structural Biology, 2007, 17:521-529). Microbial antigens from pathogenic mycobacteria, such as glucose monomycolates (GMM), mannosyl phosphomycoketides and phosphatidylinositol mannosides are known to be potent ligands for human T cells when presented by group I CD1 molecules (Zajonc an Kronenberg, supra). The immunostimulant can be a glycosylceramide, for example alpha-galactosylceramide (KRN 7000, US2003/0157135) or an analogue thereof, such as for example threitolceramide (IMM47) or other non-glycosidic iNKT cell agonists (as described in Silk et al. Cutting Edge J. Immunol, 2008). Further analogues which may be used in accordance with the invention and methods of producing such analogues are disclosed in WO2007/050668, which is incorporated herein by reference.

TLR Agonists

Intracellular TLRs such as TLRs 3, 7, 8 and 9 recognize nucleic acids. As such, synthetic oligodeoxynucleotides (ODN) such as the TLR9 agonist CpG have previously been used as immunostimulants. These TLR immunostimulants operate by a different mechanism than that employed by lipids such as alphaGalCer. These immunostimulants directly activate the cell that they are taken up by, culminating in, for example, the secretion of cytokines and chemokines that result in the further stimulation of immune responses.

The TLR expression pattern is specific for each cell type (Chiron et al, 2009). TLR expression in human B cells is characterized by high expression of TLR 1, 6, 7, 9 and 10, with the expression pattern varying during B-cell differentiation.

Soluble CpG ODNs are rapidly internalized by immune cells and interact with TLR9 that is present in endocytic vesicles. Cellular activation by most members of the TLR family (including TLR9) involves a signaling cascade that proceeds through myeloid differentiation primary response gene 88 (MYD88), interleukin-1 (IL-1), receptor-activated kinase (IRAK) and tumor-necrosis factor receptor (TNFR)-associated factor 6 (TRAF6), and culminates in the activation of several transcription factors, including nuclear factor-kappaB (NF-kappaB), activating protein 1 (AP1), CCAAT-enhancer binding protein (CEBP) and cAMP-responsive element binding protein (CREB). These transcription factors directly upregulate cytokine/chemokine gene expression. B cells and plasmacytoid dendritic cells (pDCs) are the main human cell types that express TLR9 and respond directly to CpG stimulation. Activation of these cells by CpG DNA initiates an immunostimulatory cascade that culminates in the indirect maturation, differentiation and proliferation of natural killer (NK) cells, T cells and monocytes/macrophages. Together, these cells secrete cytokines and chemokines that create a pro-inflammatory (IL-1, IL-6, IL-18 and TNF) and T.sub.H1-biased (interferon-.gamma., IFN-.gamma., and IL-12) immune milieu (Klinman, 2004, Nature Reviews, 4:249).

Thus, in some embodiments the immunostimulant is a TRL agonist. For example, it is an endosomal TLR agonist, in particular a nucleic acid, such as for example DNA, RNA (either double or single stranded). The immunostimulant may, for example comprise a CpG oligodeoxynucleotide or a poly-U nucleic acid.

Saponins

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria* Molina), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising Quil A or fractions thereof, have been used in the manufacture of vaccines (Morein, B., EP 0 109 942 B1). These structures have been reported to have adjuvant activity (EP 0 109 942 B1; WO 96/11711). The hemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Other saponins which have been used in systemic vaccination studies include those derived from other plant species such as *Gypsophila* and *Saponaria* (Bomford et al., Vaccine, 10(9):572-577, 1992).

Cytokines

TH-1 type cytokines, e.g., IFN-gamma, TNF-alpha, IL-2, IL-12, IL-18, etc, tend to favor the induction of cell mediated immune responses to an administered antigen. In contrast, high levels of Th2-type cytokines (e.g., IL4, IL-5, IL-6 and IL-10) tend to favor the induction of humoral immune responses. Interleukin-18 (IL-18), also known as interferon-gamma (IFNg) inducing factor, has been described as an pleotropic cytokine with immunomodulatory effects that stimulates patient's own immune system against disease. IL-18 has several bioactivities, including the ability to promote the differentiation of naive CD4 T cells into Th cells, to stimulate natural killer (NK) cells, natural killer T (NKT) cells, and to induce the proliferation of activated T cells, predominantly cytotoxic T cells (CD8+ phenotype) to secrete gamma interferon (IFN-gamma) (Okamura H. et al. 1998, Adv. Immunol. 70: 281-312). IL-18 also mediates Fas-induced tumor death, promotes the production of IL-1a and GMCSF, and has anti-angiogenic activity. IFN-α 2a, including pegylated versions thereof (Pegasys), can also be used. Recombinant human Interleukin-7 (r-hIL-7/CYT107) can also be used.

Vaccines

As used herein, "vaccine" includes all prophylactic and therapeutic vaccines. A vaccine includes an antigen or immunogenic derivative, and an adjuvant. As used herein, the vaccines can be any vaccine that inhibits any of the viruses described herein, including anti-HIV vaccines which inhibit HIV through any mechanism.

Where the vaccine is an anti-HIV vaccine, it ideally inhibits or stops the HIV virion replication cycle at any one of the following phases of the HIV virion cycle:
Phase I. Free State
Phase II. Attachment
Phase III. Penetration
Phase IV. Uncoating
Phase V. Replication
Phase VI. Assembling
Phase VII. Releasing While many antiviral vaccines use live viruses, with respect to HIV vaccines, it is not advisable to use live viruses, due to the risk of infection. However, it is known that deletion of the HIV nef gene attenuates the virus. Desrosiers and his associates have demonstrated that vaccination of macaques with nef-deleted SIV protected wild-type SIV challenge (Daniels, M. D. et al. Science 258:1938 (1992); Desrosiers, R. C., et al. Proc. Natl. Acad. Sci. USA 86:6353 (1989)) and others have demonstrated that nef gene is dispensable for SIV and HIV replication (Daniels, M. D. et al. Science 258:1938 (1992); Gibbs, J. S., et al. AIDS Res. and Human Retroviruses 10:343 (1994); Igarashi, T., et al. J. Gen. Virol. 78:985 (1997); Kestler III, H. W., et al. Cell 65:651 (1991)). Furthermore, deletion of nef gene renders the virus to be non-pathogenic in the normally susceptible host (Daniels, M. D. e t al. Science 258:1938 (1992)).

In terms of antigens, subunit vaccines can be used (Cooney E L, et al., Proc Natl Acad Sci USA 1993; 90; 1882-86; McElrath M J, et al. J Infect Dis. 169: 41-47 (1994); Graham B S, et al. J Infect Dis 166: 244-52 (1992); and Graham B S, et al. J Infect Dis 167: 533-37 (1993)). HIV-derived antigens include HIV-1 antigen gp120, tat, nef, reverse transcriptase, gag, gp120 and gp160, and various targets in pol One examples of an HIV vaccine is the DermaVir therapeutic HIV vaccine, currently in Phase II clinical studies.

The vaccines of the present invention may additionally contain suitable diluents, adjuvants and/or carriers. In some embodiments, the vaccines contain an adjuvant which can enhance the immunogenicity of the vaccine in vivo. The adjuvant may be selected from many known adjuvants in the art, including the lipid-A portion of gram negative bacteria endotoxin, trehalose dimycolate of mycobacteria, the phospholipid lysolecithin, dimethyldictadecyl ammonium bromide (DDA), certain linear polyoxypropylene-polyoxyethylene (POP-POE) block polymers, aluminum hydroxide, and liposomes. The vaccines may also include cytokines that are known to enhance the immune response including GM-CSF, IL-2, IL-12, TNF-α and IFNγ.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

The vaccines may be administered in a convenient manner such as by injection (subcutaneous, intravenous, intramuscular, etc.), oral administration, inhalation, transdermal administration (such as topical cream or ointment, etc.), or suppository applications.

Recombinant Retrovirus

The recombinant retrovirus of the present invention can be any retrovirus, including HIV-1, HIV-2, SIV, HTLV-1. Preferably the retrovirus is a human immunodeficiency virus selected from HIV-1 and HIV-2, more preferably, the retrovirus is HIV-1.

The vaccine can be an essentially non-cytolytic retrovirus, wherein the term "essentially non-cytolytic" means that the retrovirus does not significantly damage or kill the cells it infects. In one embodiment, the natural signal sequence of HIV-1 envelope glycoprotein gp120 (NSS) is modified to be essentially non-cytolytic, or is replaced with an essentially non-cytolytic signal sequence.

In one embodiment, the present invention provides an essentially non-cytolytic recombinant HIV-1 capable of highly efficient replication wherein the NSS of the virus' envelope glycoprotein is modified sufficiently to prevent cell damage by the virus, preferably by eliminating positively charged amino acids, even more preferably, such elimination or modification resulting in no more than one (1) and preferably zero (0) positively charged amino acids. The positively charged amino acids which may be modified or replaced include lysine and arginine.

In another embodiment, replacement of the natural signal sequence results in a more efficient replication of HIV. Accordingly the present invention provides an essentially non-cytolytic recombinant HIV-1 capable of highly efficient replication wherein the NSS of the virus' envelope glycoprotein is replaced with an essentially non-cytolytic and more efficient signal sequence. In a preferred embodiment, replacement of the NSS of the envelope glycoprotein of HIV-1 with either the mellitin or IL-3 signal sequence decreases the cytotoxicity of the retrovirus. As such, the present invention includes within its scope replacement of NSS with any signal sequence which renders the retrovirus essentially non-cytolytic. The inventors have also shown that replacement of the NSS with mellitin or IL-3 signal sequences results in a greater level of production and secretion of gp120, in addition to the reduced cytotoxicity. The inventors have also shown that replacement of the NSS results in partial deletion the vpu gene. Studies have shown the vpu gene can be completely deleted without any measurable impact on the virus' ability to replicate (James et al. AIDS Res. Human Retrovirus 10:343-350, 1994).

In another embodiment, the retrovirus is rendered avirulent. In a preferred embodiment, the virus is rendered avirulent by deleting the nef gene. Accordingly, the present invention provides an avirulent, essentially non-cytolytic retrovirus which contains a sufficient deletion of the nef gene to render the virus non-pathogenic and wherein the virus' envelope glycoprotein gp120 coding sequence is replaced with a more efficient signal sequence. As used herein, "sufficient deletion" means deletion of enough of the sequence to prevent transcription and thereby production of the nef protein product.

In a further embodiment, the retrovirus is rendered avirulent, essentially non-cytolytic, and contains a sufficient deletion of the nef gene and the vpu gene to render the virus non-pathogenic.

Recombinant retroviruses be prepared using techniques known in the art. In one embodiment, the retrovirus can be introduced in a host cell under conditions suitable for the replication and expression of the retrovirus in the host.

The essentially non-cytolytic and avirulent retroviruses can typically be produced in large quantities and in a form that is non-pathogenic to the patient. The viruses can be used, in combination with the JAK inhibitors and, optionally, with HAART, for preventing or treating a retroviral infection. In this use, an effective amount of a killed recombinant essentially non-cytolytic avirulent retrovirus is administered to a patient in need of treatment or prophylaxis of a retroviral infection. The term "effective amount" as used herein means an amount effective and at dosages and for periods of time necessary to achieve the desired result.

In one embodiment, the natural signal sequence of the virus' envelope glycoprotein, such as gp120, is modified to provide an essentially non-cytolytic signal sequence, and/or the virus is rendered avirulent by deleting the nef gene. In one aspect of this embodiment, the modification to provide a non-cytolytic NSS results in no more than one positively charged amino acid in the NSS sequence, more preferably zero positively charged amino acids.

In another aspect of this embodiment, the natural signal sequence of the virus' envelope glycoprotein, preferably gp120, is replaced with an essentially non-cytolytic signal sequence, and, optionally, the virus is rendered avirulent by deleting the nef gene.

In another aspect of this embodiment, where the NSS is replaced, the non-cytolytic signal sequence is selected from the group consisting of the mellitin sequence and the IL-3 signal sequence.

Chimaeric Antigens

The vaccines can comprise chimaeric antigens, for example, a chimaeric influenza-HIV vaccine. In one embodiment, the vaccine comprises the A-antigenic loop of influenza haemagglutinin (HA-A), modified to resemble the principle neutralizing determinant (PND) of HIV envelope glycoprotein gp120. The Chimaeric antigens can be presented as killed or attenuated virus.

Vaccine Production

To produce a vaccine, the antigen is typically combined with a pharmaceutically acceptable carrier, and, typically, an adjuvant, to make a composition comprising a vaccine. This vaccine composition is optionally combined with an immunostimulant and administered to a patient in need of treatment or prevention of a viral infection.

In one embodiment, the vaccine includes antigens selected for more than one virus, particularly where co-infection rates are known to be high. One example is HIV and HBV or HCV, or HIV and influenza.

A variety of adjuvants known to one of ordinary skill in the art may be administered in conjunction with the protein in the vaccine composition. Such adjuvants include, but are not limited to the following: polymers, co-polymers such as polyoxyethylene-polyoxypropylene copolymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; or combinations thereof.

The vaccine formulations can be presented in unit dosage form, and can be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, and topical. The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. Initial injections may range from about 1 mg to 1 gram, with a preferred range of about 10 mg to 800 mg, and a more preferred range of from approximately 25 mg to 500 mg. Booster injections may range from 1 mg to 1 gram, with a preferred range of approximately 10 mg to 750 mg, and a more preferred range of about 50 mg to 500 mg.

The volume of administration will vary depending on the route of administration. Intramuscular injections may range from about 0.1 ml to 1.0 ml.

The vaccines can be administered before, during or after an infection. An infected individual can receive a vaccine directed to the virus infecting the individual, even though the levels are reduced via treatment with the JAK inhibitors and/or HAART, stimulating the immune system to fight the virus that remains in the individual.

The vaccine may be stored at temperatures of from about 4 C. to −100 C. The vaccine may also be stored in a lyophilized state at different temperatures including room temperature. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Treatment or Prevention of Other Viral Infections

The invention includes methods for treating or preventing, and uses for the treatment or prophylaxis, of a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus).

Viruses Characterized by the Flaviviridae Family

The Flaviviridae is a group of positive single-stranded RNA viruses with a genome size from 9-15 kb. They are enveloped viruses of approximately 40-50 nm. An overview of the Flaviviridae taxonomy is available from the International Committee for Taxonomy of Viruses. The Flaviviridae consists of three genera.

Flaviviruses. This genus includes the Dengue virus group (Dengue virus, Dengue virus type 1, Dengue virus type 2, Dengue virus type 3, Dengue virus type 4), the Japanese encephalitis virus group (Alfuy Virus, Japanese encephalitis virus, Kookaburra virus, Koutango virus, Kunjin virus, Murray Valley encephalitis virus, St. Louis encephalitis virus, Stratford virus, Usutu virus, West Nile Virus), the Modoc virus group, the Rio Bravo virus group (Apoi virus, Rio Brovo virus, Saboya virus), the Ntaya virus group, the Tick-Borne encephalitis group (tick born encephalitis virus), the Tyuleniy virus group, Uganda S virus group and the Yellow Fever virus group. Apart from these major groups, there are some additional Flaviviruses that are unclassified.

Pestiviruses. This genus includes Bovine Viral Diarrhea Virus-2 (BVDV-2), Pestivirus type 1 (including BVDV), Pestivirus type 2 (including Hog Cholera Virus) and Pestivirus type 3 (including Border Disease Virus).

Hepaciviruses. This genus contains only one species, the Hepatitis C virus (HCV), which is composed of many clades, types and subtypes.

Chikungunya virus, an RNA virus of the genus Alphavirus, can also be treated using the compounds described herein.

Those of skill in the art can effectively follow the administration of these therapies, and the development of side effects and/or resistant viral strains, without undue experimentation.

The present invention will be better understood with reference to the following non-limiting examples.

Example 1: Comparison of JAK Inhibitors to Conventional Antiretroviral Therapy

Current first line highly active antiretroviral therapy (HAART) for the treatment of human immunodeficiency virus (HIV-1) infections combines two nucleoside reverse transcriptase inhibitors (NRTI) together with either a protease inhibitor (PI) or non-nucleoside reverse transcriptase inhibitor (NNRTI). These drug combinations have markedly decreased mortality and morbidity from HIV-1 infections in the developed world.

Existing therapies cannot eradicate HIV-1 infection because of the compartmentalization of the virus and its latent properties. Therefore, chronic therapy remains the standard of care for the foreseeable future. Although HAART regimens are selected in part to minimize cross resistance, and thereby delay the emergence of resistant viruses, all regimens eventually fail, due primarily to lack of adherence to strict regimens, delayed toxicities and/or the emergence of drug-resistant HIV-1 strains, making it a major imperative to develop regimens that delay, prevent or attenuate the onset of resistance for second line treatments for infected individuals who have already demonstrated mutations. The occurrence of common resistance mutations, including thymidine analog mutations (TAM), K65R and M184V, need to be a continued focus in the rational design of HIV-1 NRTI drug development.

The objectives of this study were to evaluate JAK inhibitors that do not appear to function in the same manner as NRTI, NNRTI, protease inhibitors, entry inhibitors, integrase inhibitors, and the like. In the data shown in this example, the JAK inhibitors that were evaluated were Jakafi (Incyte) and Tofacitinib (Pfizer).

PBM Cell and Mφ Protocol for Antiviral Potency

Macrophages were isolated as follows: Monocytes were isolated from buffy coats of HIV-1 negative, HBV/HCV-negative donors with density gradient centrifugation coupled with enrichment for CD14+ monocytes with Rosette Sep antibody cocktail (Stem Cell Technologies, Vancouver, British Columbia). Cells were seeded at a concentration of $1.0\times10^6$ cells/well for 1 hr at 37° C. and 5% $CO_2$ to confer plastic adherence prior to repeated washes with 1×PBS. Macrophages were maintained in medium containing 100 U/ml macrophage colony-stimulating factor (m-CSF, R&D Systems, Minneapolis, Minn.), supplemented with 20% fetal calf serum (Atlanta Biologicals, Lawrenceville, Ga.) and 1% penicillin/streptomyocin (Invitrogen, Carlsbad, Calif.) for 7 days (37° C., 5% CO2) prior to testing.

Macrophage infections: Macrophages were cultured as described above for 7 days. For acute infection, macrophages were serum starved for 8 hrs prior to infection and cultured for 2 hr in medium containing various concentrations of AZT (positive control) or Tofacitinib and Jakafi for 2 hr prior to removal of drug-containing medium and 4 hr infection with HIV-1BaL at 0.1 MOI in the absence of drug. 4 hrs after infection, virus was removed and drug-containing medium was returned to the cultures. Supernatants were collected on day 7 post-infection and HIV-1 p24 was quantified via ELISA (Zeptometrix Corporation, Buffalo, N.Y.). EC50 analysis was performed using CalcuSyn software (BioSoft Corporation, Cambridge, UK).

PBM cells were isolated as follows: Lymphocytes were isolated from buffy coats derived from healthy donors obtained from Life South Laboratories (Dunwoody, Ga.). Activated lymphocytes were maintained for 72 hrs in medium that was supplemented with 6 μg/ml phytohemagglutinin (PHA) (Cape Cod associates, East Falmouth, Mass.). Media was comprised of RPMI media supplemented with 20% fetal calf serum, 1% penicillin/streptomyocin and 2% L-glutamine (Sigma Aldrich, San Jose, Calif.).

PBM cell infections: Testing was performed in duplicate with at least 3 independent assays. Cells were incubated in RPMI medium (HyClone, Logan, Utah) containing HR-TL2 (26.5 units/ml) and 20% fetal calf serum. Infections were performed by adding HIV-$1_{LAI}$ followed by a further incubation at 37° C., 5% CO2, 1 hr prior to addition of drugs. Assays were performed in 24 well plates (BD Biosciences, Franklin Lakes, N.J.). One ml of supernatant was collected after 5 days in culture and then centrifuged at 12,000 rpm for 2 hr at 4° C. in a Jouan Br43i (Thermo Electron Corp., Marietta, Ohio). The product of the RT assay was quantified using a Packard harvester and direct beta counter and the data were analyzed as previously described (Schinazi et al, 1990).

Cytotoxicity Assay

The toxicity of the compounds was assessed in Vero, human PBM, CEM (human lymphoblastoid), as described previously (see Schinazi R. F., Sommadossi J.-P., Saalmann V., Cannon D. L., Xie M.-Y., Hart G. C., Smith G. A. & Hahn E. F. Antimicrob. Agents Chemother. 1990, 34, 1061-67), and also in MO cells. Cycloheximide was included as positive cytotoxic control, and untreated cells exposed to cell culture medium were included as negative controls.

The cytotoxicity $IC_{50}$ was obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11).

Figure 1:

The potency and toxicity of JAK inhibitors Tofacitinib and Jakafi versus FDA approved controls AZT and 3TC was evaluated in acutely infected activated MO, as well as in PBM cells. The $EC_{50}$ data (μM) is shown in FIG. 1. Also shown in FIG. 1 are the $IC_{50}$ values (μM) for these compounds in PBM, MO cells, CEM cells, and Vero cells.

The data show a very large therapeutic window (ratio of toxicity/potency), and that the JAK inhibitor compounds have substantially the same $EC_{50}$ and substantially lower $IC_{50}$ values as AZT and 3TC.

Figure 2:
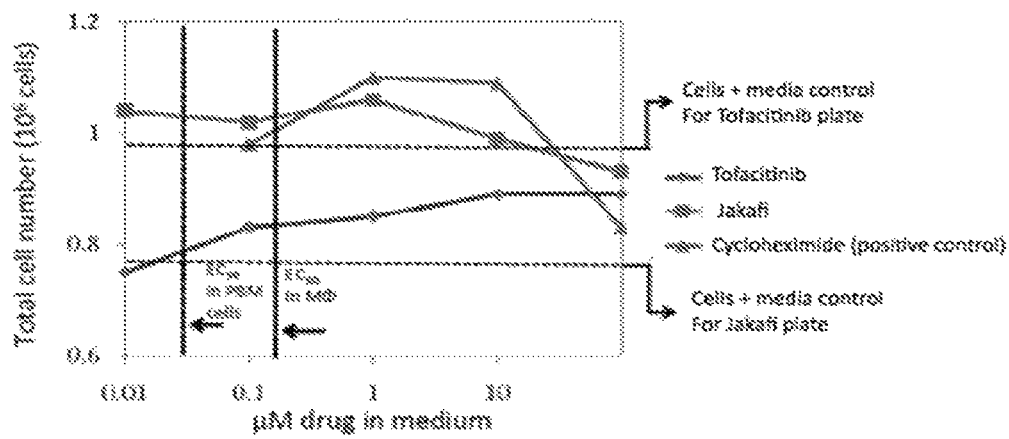

Cell proliferation was evaluated in activated PBM cells incubated for 5 days with various concentrations of Tofacitinib and Jakafi, with cycloheximide as a positive control, and a "cells plus media" control used as well. The data is shown in FIG. 2, in terms of total cell number ($10^6$ cells) versus μM drug in medium. The data shows that Tofacitinib and Jakafi do not affect total cell proliferation at antiviral concentrations.

Figure 3:
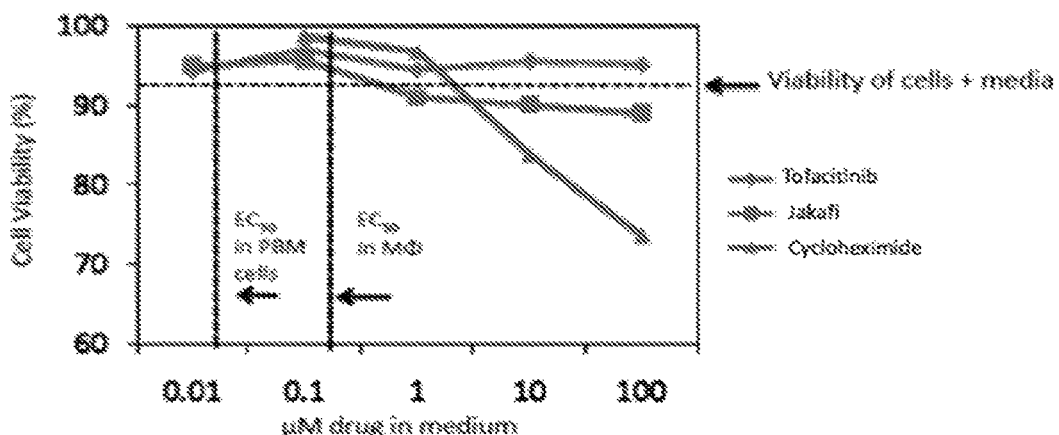

Cell viability was evaluated in activated PBM cells incubated for 5 days with various concentrations of Tofacitinib and Jakafi, with cycloheximide as a positive control, and a "cells plus media" control used as well. The data is shown in FIG. 3, in terms of cell viability (%) versus μM drug in medium. The data shows that Tofacitinib and Jakafi do not affect total cell viability at antiviral concentrations.

Conclusion

In conclusion, Tofacitinib and Jakafi are potent, sub-micromolar inhibitors of HIV-1 replication in both PBM cells and Mø cells. The compounds do not affect viability or proliferation for PBM cells and Mø cells, or total cell number, up to around 10 μM (2-3 logs above $EC_{50}$). The therapeutic window (ratio of toxicity:potency) is wide for both cell types (24->100).

Example 2: Mitochondrial Toxicity Assays in HepG2 Cells i) Effect of the JAK Inhibitors described herein on Cell Growth and Lactic Acid Production: The effect on the growth of HepG2 cells can be determined by incubating cells in the presence of 0 μM, 0.1 μM, 1 μM, 10 μM and 100 μM drug. Cells ($5\times10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the compounds on lactic acid production, HepG2 cells from a stock culture can be diluted and plated in 12-well culture plates at $2.5 \times 10^4$ cells per well. Various concentrations (0 μM, 0.1 μM, 1 μM, 10 μM and 100 μM) of the compounds can be added, and the cultures incubated at 37° C. in a humidified 5% $CO_2$ atmosphere for 4 days. At day 4 the number of cells in each well can be determined and the culture medium collected. The culture medium was filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of the compounds would indicate a drug-induced cytotoxic effect.

ii) Effect on the compounds on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay can be used to determine the effect of the compounds on mitochondrial DNA content. In this assay, low-passage-number HepG2 cells are seeded at 5,000 cells/well in collagen-coated 96-well plates. The compounds are added to the medium to obtain final concentrations of 0 μM, 0.1 μM, 10 μM and 100 μM. On culture day 7, cellular nucleic acids are prepared by using commercially available columns (RNeasy 96 kit; Qiagen). These kits co-purify RNA and DNA, and hence, total nucleic acids were eluted from the columns. The mitochondrial cytochrome c oxidase subunit II (COXII) gene and the ß-actin or rRNA gene were amplified from 5 μl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3' (SEQ ID No. 1), 5'-tetrachloro-6-carboxyfluorescein-TCCTCATCGCCC-TCCCATCCC-TAMRA-3' (SEQ ID No. 2), and 5'-CGTCTGTTATGTAAAGGATGCGT-3' (SEQ ID No. 3). For exon 3 of the ß-actin gene (GenBank accession number E01094) the sense, probe, and antisense primers are 5'-GCGCGGCTACAGCTTCA-3' (SEQ ID No. 4), 5'-6-FAMCACCACGGCCGAGCGGGATAMRA-3' (SEQ ID No. 5), and 5'-TCTCCTTAATGTCACGCACGAT-3' (SEQ ID No. 6), respectively. The primers and probes for the rRNA gene are commercially available from Applied Biosystems. Since equal amplification efficiencies are obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample–CT for target control)–(CT for average reference test –CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

iii) Electron Microscopic Morphologic Evaluation: NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells. Biochem. Pharmacol. 1996, 52, 1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, X J Zhou, J P Sonunadossi, V M Darley-Usmar. Differential effects of antiretroviral nucleoside analogs on mitochondrial function in HepG2 cells. *Antimicrob. Agents Chemother.* 2000, 44, 496-503). For example, electron micrographs of HepG2 cells incubated with 10 μM fialuridine (FIAU; 1,2'-deoxy-2'-fluoro-1-D-arabinofuranosly-5-iodo-uracil) showed the presence of enlarged mitochondria with morphological changes consistent with mitochondrial dysfunction. To determine if the JAK inhibitor compounds promote morphological changes in mitochondria, HepG2 cells ($2.5 \times 10^4$ cells/mL) can be seeded into tissue cultures dishes (35 by 10 mm) in the presence of 0 μM, 0.1 μM, 1 μM, 10 μM and 100 μM nucleoside analog. At day 8, the cells can be fixed, dehydrated, and embedded in Eponas described previously. Thin sections can be prepared, stained with uranyl acetate and lead citrate, and then examined using transmission electron microscopy.

Example 3: Mitochondrial Toxicity Assays in Neuro2A Cells

To estimate the potential of the JAK inhibitor compounds to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% ($CC_{50}$) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above.

Example 4: Assay for Bone Marrow Cytotoxicity

Primary human bone marrow mononuclear cells were obtained commercially from Cambrex Bioscience (Walkersville, Md.). CFU-GM assays can be carried out using a bilayer soft agar in the presence of 50 units/mL human recombinant granulocyte/macrophage colony-stimulating factor, while BFU-E assays used a methylcellulose matrix containing 1 unit/mL crythropoictin (see Sommadossi J P, Carlisle R. Toxicity of 3'-azido-3'-deoxythymidine and 9-(1, 3-dihydroxy-2-propoxymethyl) guanine for normal human hepatopoietic progenitor cells in vitro. Antimicrob. Agents Chemother. 1987; 31: 452-454; Sonmnadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT can be used as a positive control. Cells can be incubated in the presence of a JAK inhibitor compound for 14-18 days at 37° C. with 5% CO2, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 5: Anti-HBV Assay

The anti-HBV activity of the JAK inhibitor compounds can be determined by treating the AD-38 cell line carrying wild type HBV under the control of tetracycline (see Ladner S. K., Otto M. J., Barker C. S., Zaifert K., Wang G. H., Guo J. T., Seeger C. & King R. W. Antimicrob. Agents Chemother. 1997, 41, 1715-20). Removal of tetracycline from the medium [Tet (−)] results in the production of HBV. The levels of HBV in the culture supernatant fluids from cells treated with the compounds can be compared with that of the untreated controls. Control cultures with tetracycline [Tet (+)] can also be maintained to determine the basal levels of HBV expression. 3TC can be included as positive control.

Example 6: Cytotoxicity Assay

The toxicity of the compounds can be assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. Antimicrob. Agents Chemother. 1990, 34, 1061-67). Cycloheximide can be included as positive cytotoxic control, and untreated cells exposed to solvent can be included as negative controls. The cytotoxicity IC50 can be obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11).

Example 7: HCV Replicon Assay[1]

Huh 7 Clone B cells containing HCV Replicon RNA can be seeded in a 96-well plate at 5000 cells/well, and the JAK inhibitor compounds tested at 10 µM in triplicate immediately after seeding. Following five days incubation (37° C., 5% CO$_2$), total cellular RNA can be isolated by using versaGene RNA purification kit from Gentra. Replicon RNA and an internal control (TaqMan rRNA control reagents, Applied Biosystems) can be amplified in a single step multiplex Real Time RT-PCR Assay. The antiviral effectiveness of the compounds can be calculated by subtracting the threshold RT-PCR cycle of the test compound from the threshold RT-PCR cycle of the no-drug control (ΔCt HCV).

A ΔCt of 3.3 equals a 1-log reduction (equal to 90% less starting material) in Replicon RNA levels. The cytotoxicity of the compounds can also be calculated by using the ΔCt rRNA values. (2'-Me-C) can be used as the control. To determine $EC_{90}$ and $IC_{50}$ values[2], ΔCt: values can first be converted into fraction of starting material[3] and then were used to calculate the % inhibition.

References:
1. Stuyver L et al., Ribonucleoside analogue that blocks replication or bovine viral diarrhea and hepatitis C viruses in culture. Antimicrob. Agents Chemother. 2003, 47, 244-254.
2. Reed I J & Muench H, A simple method or estimating fifty percent endpoints. Am. J. Hyg. 27: 497, 1938.
3. Applied Biosystems Handbook Example 8: Assay for Effectiveness Against West Nile Virus West Nile virus drug susceptibility assays can also be done as previously described in: Song, G. Y., Paul, V., Choo, H., Morrey, J., Sidwell, R. W., Schinazi, R. F., Chu, C. K. Enantiomeric synthesis of D- and L-cyclopentenyl nucleosides and their antiviral activity against HIV and West Nile virus. J. Med. Chem. 2001, 44, 3985-3993.

Example 9: Assay for Effectiveness Against Yellow Fever

Yellow fever drug susceptibility assays can also be done as previously described in: Julander, J. G., Furuta, Y., Shafer, K., Sidwell, R. W. Activity of T-1106 in a Hamster Model of Yellow Fever Virus Infection. Antimicrob. Agents Chemother. 2007, 51, 1962-1966.

Example 10: Assay for Effectiveness Against Dengue

One representative high throughput assay for identifying compounds useful for treating Dengue is described in Lim et al., A scintillation proximity assay for dengue virus NS5 2'-O-methyltransferase-kinetic and inhibition analyses, Antiviral Research, Volume 80, Issue 3, December 2008, Pages 360-369.

Dengue virus (DENV) NS5 possesses methyltransferase (MTase) activity at its N-terminal amino acid sequence and is responsible for formation of a type 1 cap structure, m7GpppAni2'-O in the viral genomic RNA. Optimal in vitro conditions for DENV2 2'-O-MTase activity can be characterized using purified recombinant protein and a short biotinylated GTP-capped RNA template. Steady-state kinetics parameters derived from initial velocities can be used to establish a robust scintillation proximity assay for compound testing. Pre-incubation studies by Lim et al., Antiviral Research, Volume 80, Issue 3, December 2008, Pages 360-369, showed that MTase-AdoMet and MTase-RNA complexes were equally catalytically competent and the enzyme supports a random bi bi kinetic mechanism. Lim validated the assay with competitive inhibitory agents, S-adenosyl-homocysteine and two homologues, sinefungin and dehydrosinefungin. A GTP-binding pocket present at the N-terminal of DENV2 MTase was previously postulated to be the cap-binding site. This assay allows rapid and highly sensitive detection of 2'-O-MTase activity and can be readily adapted for high-throughput screening for inhibitory compounds. It is suitable for determination of enzymatic activities of a wide variety of RNA capping MTases.

Example 11. Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473)

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay may be useful for screening entry inhibitors.

Example 12: Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives approximately 250 µCi of $^3$H activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (TmaX), area under the curve (AUC), half life of the dosage concentration (TV), clearance (CL), steady state volume and distribution (Vss) and bioavailability (F).

Example 13: Cell Protection Assay (CPA)

The assay can be performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate.

Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm.

The 50% effective concentration ($EC_{50}$) values are defined as the compound concentration that achieved 50% reduction of cytopathic effect of the virus.

Example 14: Plaque Reduction Assay

For a compound, the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Example 15: Yield Reduction Assay

For a compound, the concentration to obtain a 6-log reduction in viral load is determined in duplicate 24-well plates by yield reduction assays. The assay is performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986, with minor modifications.

Briefly, MDBK cells are seeded onto 24-well plates ($2\times10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates (5×10$^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 16: Diagnosis of Norovirus Infection

One can diagnose a norovirus infection by detecting viral RNA in the stools of affected persons, using reverse transcription-polymerase chain reaction (RT-PCR) assays. The virus can be identified from stool specimens taken within 48 to 72 hours after onset of symptoms, although one can obtain satisfactory results using RT-PCR on samples taken as long as 7 days after the onset of symptoms. Other diagnostic methods include electron microscopy and serologic assays for a rise in titer in paired sera collected at least three weeks apart. There are also commercial enzyme-linked immunoassays available, but these tend to have relatively low sensitivity, limiting their use to diagnosis of the etiology of outbreaks. Clinical diagnosis of norovirus infection is often used, particularly when other causative agents of gastroenteritis have been ruled out.

Example 17: In Vitro Antiviral Activity

In vitro anti-viral activity can be evaluated in the following cell lines:
The Norwalk G-I strain (Chang, K. O., et al. (2006) Virology 353:463-473), the GII-4 strain replicon, as well other Norovirus replicons can be used in assays to determine the in vitro antiviral activity of the compounds described herein, or other compounds or compound libraries.

In some embodiments, the replicon systems are subgenomic and therefore allow evaluation of small molecule inhibitors of non-structural proteins. This can provide the same benefits to Norovirus drug discovery that Hepatitis C replicons contributed to the discovery of therapeutics useful for treatment of that virus (Stuyver, L. J., et al. (2006) Antimicrob. Agents Chemother. 47:244-254). Both Norovirus replicons and Hepatitis C replicons require viral helicase, protease, and polymerase to be functional in order for replication of the replicon to occur. It is believed that the compounds described herein inhibit viral polymerase and/or viral helicase.

The in vitro cell culture infectivity assay reported using Norovirus genogroup I and II inoculums (Straub, T. M. et al. (2007) Emerg. Infect. Dis. 13(3):396-403) can also be used. This assay can be performed in a rotating-wall bioreactor utilizing small intestinal epithelial cells on microcarrier beads. The infectivity assay can be used for evaluating compounds for their ability to inhibit the desired virus.

Example 18: Antiviral Potency and Toxicity of Jakafi and Tofacitinib in Primary Human Lymphocytes and Macrophages The antiviral potency and toxicity of jakafi and tofacitinib was evaluated in primary human lymphocytes and macrophages, using the methodology outlined above.

The antiviral potency against HIV-1LAI in primary human lymphocytes was 0.1-0.8 μM (EC$_{50}$) and 4.7-15.1 μM (EC$_{90}$). Antiviral potency against HIV-2 in primary human lymphocytes was 0.02-0.07 μM (EC$_{50}$) and 0.4-1.8 μM (EC$_{90}$). Antiviral potency against HIV-1BaL in primary human macrophages was approximately 0.3 μM (EC$_{50}$) and 3.0 μM (EC$_{90}$). AZT (control) demonstrated antiviral potency against HIV-1LAI, HIV-2, and HIV-1BaL as expected. Toxicity (IC$_{50}$) measured with the MTT assay ranged from 1.3 to >100 μM depending on the cell type tested. Propidium Iodide (primary human lymphocytes) demonstrated IC$_{50}$>50 μM. Data are mean and standard deviations from at least three independent experiments.

The data is shown below in Tables 1 and 2.

TABLE 1

| Compound | Anti-HIV-1 EC$_{50}$ in acutely infected PBM cells (μM) | Anti-HIV-1 EC$_{90}$ in acutely infected PBM cells (μM) | Anti-HIV-2 EC$_{50}$ in acutely infected PBM cells (μM) | Anti-HIV-2 EC$_{90}$ in acutely infected PBM cells (μM) | Anti-HIV-1 EC$_{50}$ in acutely infected MΦ (μM) | Anti-HIV-1 EC$_{90}$ in acutely infected MΦ (μM) |
|---|---|---|---|---|---|---|
| Jakafi | 0.1 ± 0.02 | 4.7 ± 0.07 | 0.02 ± 0.01 | 0.4 ± 0.2 | 0.3 ± 0.1 | 3.1 ± 1.8 |
| Tofacitinib | 0.8 ± 0.3 | 17.1 ± 15.1 | 0.07 ± 0.006 | 1.8 ± 1.1 | 0.2 ± 0.08 | 2.9 ± 1.4 |
| AZT | 0.02 ± 0.008 | 0.13 ± 0.03 | 0.001 ± 0.0008 | 0.01 ± 0.01 | 0.01 ± 0.02 | 0.07 ± 0.12 |

TABLE 2

| Compound | IC$_{50}$ in PHA + IL-2 PBM cells(μM) *MTT Assay | IC$_{50}$ in PHA stimulated PBM cells(μM) *MTT Assay | IC$_{50}$ in PBM cells(μM) *Propidium Iodide assay | IC$_{50}$ in MΦ(μM) *MTT Assay | IC$_{50}$ in CEM cells (μM) *MTT Assay | IC$_{50}$ in Vero cells(μM) *MTT Assay |
|---|---|---|---|---|---|---|
| Jakafi | 3.1 ± 1.7 | 9.1 ± 1.3 | >50 | >100 | 11.8 ± 1.1 | 29.3 ± 3.7 |
| Tofacitinib | 1.3 ± 0.9 | 6.3 ± 1.8 | >50 | 49.2 | >100 | >100 |
| AZT | >100 | >100 | >50 | >100 | 14.3 | 56.0 |

Example 19: Therapeutic Index for Jakafi and Tofacitinib in Primary Human Lymphocytes and Macrophages The therapeutic index (ratio of toxicity:potency) for Jakafi and Tofacitinib was evaluated in primary human lymphocytes and macrophages using the methodology described above. The therapeutic index ranged from 1.0-31.0 for HIV-1 infection in primary human lymphocytes when using MTT assay toxicity values, and were >100 using propidium iodide toxicity values. The therapeutic Index ranged from 18 to >100 for HIV-2 infection in primary human lymphocytes when using MTT assay toxicity values, and were >100 using propidium iodide toxicity values. The therapeutic index for HIV-1 infection in primary human macrophages was >100 (MTT assay toxicity values).

The data are shown below in Tables 3 and 4.

FIGS. 4a-f show the results of flow cytometric analysis of PHA+IL-2 stimulated primary human lymphocytes exposed to various concentrations of Jakafi or Tofacitinib for 5 days prior to assessment of viability using propidium iodide (flow cytometry).

Figure 4A:
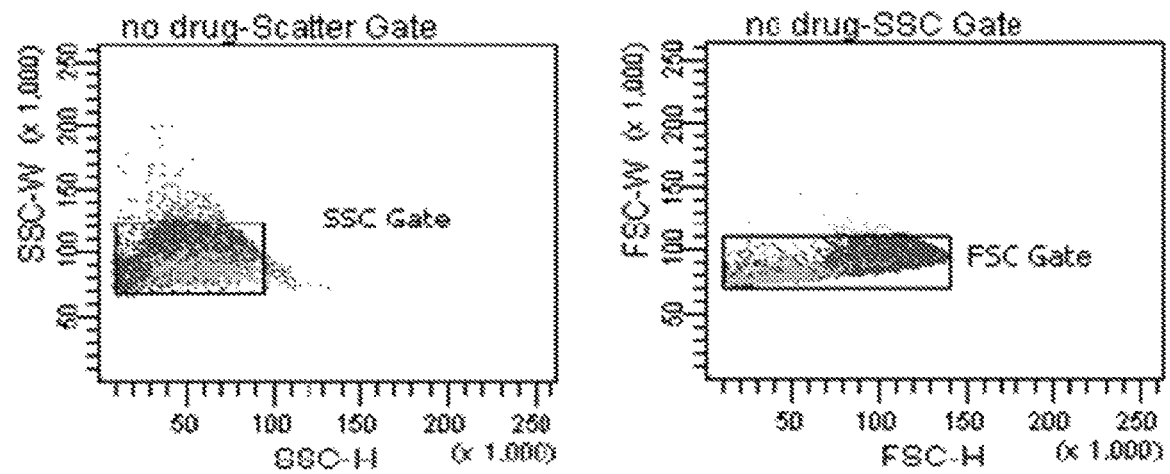
FIG. 4c shows histograms comparing the cell viability for cells exposed to Jakafi and to no drug (i.e., controls) for concentrations of 0.1 μM Jakafi, 1.0 μM Jakafi, 10 μM Jakafi, and 50 μM Jakafi.
FIG. 4d shows histograms comparing the cell viability for cells exposed to Tofacitinib and to no drug (i.e., controls) for concentrations of 0.1 μM Tofacitinib, 1.0 μM Tofacitinib, 10 μM Tofacitinib, and 50 μM Tofacitinib.
FIGS. 4e and 4f are charts showing the mean and standard deviations from the experiments shown in FIGS. 4c (Jakafi) and 4d (Tofacitinib), respectively.

A gating strategy based on forward scatter (FSC) and side scatter (SSC) was established, and used uniformly across all samples. FIG. 4a is a scatter plot showing a Side Scatter (SSC) gating strategy, where the X-axis in the first chart is Side Scatter Pulse Height (SSC-h) and the Y-axis is Side Scatter Pulse Width (SSC-w), and in the second chart, the forward-scattered light (FSC) is shown with the X axis being Forward Scatter Pulse Height (FSC-H) and the Y axis being Forward Scatter Pulse Width (FSC-W). The gating strategy based on forward scatter (FSC) and side scatter (SSC) was established and used uniformly across all samples.

TABLE 3

| Compound | TI forantiviral potency against acute HIV-1 infection in PBM cells versus toxicity * Calculated using MTT assay toxicity values for PHA + IL-2 stimulated PBM cells | TI forantiviral potency against acute HIV-1 infection in PBM cells versus toxicity * Calculated using MTT assay toxicity values for PHA stimulated PBM cells | TI for antiviral potency against acute HIV-1 infection in PBM cells versus toxicity * Calculated using Propidium Iodide toxicity values |
|---|---|---|---|
| Jakafi | 31.0 | >100 | >100 |
| Tofacitinib | 1.0 | 8.0 | >100 |
| AZT | >100 | >100 | >100 |

TABLE 4

| Compound | TI for antiviral potency against acute HIV-2 infection in PBM cells versus toxicity * Calculated using MTT assay toxicity values | TI for antiviral potency against acute HIV-2 infection in PBM cells versus toxicity * Calculated using Propidium Iodide toxicity values | TI for antiviral potency against acute HIV-1 infection versus toxicity in macrophages * Calculated using MTT assay toxicity values |
|---|---|---|---|
| Jakafi | >100 | >100 | >100 |
| Tofacitinib | 18.5 | >50 | >100 |
| AZT | >100 | >50 | >100 |

Example 20: Viability of Primary Human Lymphocytes Exposed to Various Concentrations of Jakafi or Tofacitinib The viability of primary human lymphocytes exposed to various concentrations of Jakafi or Tofacitinib was determined using the techniques discussed above.

PHA and interleukin-2 (IL-2) stimulated primary human lymphocytes were exposed to various concentrations of Jakafi or Tofacitinib for 5 days prior to assessment of viability using propidium Iodide (flow cytometry).

Figure 4B:
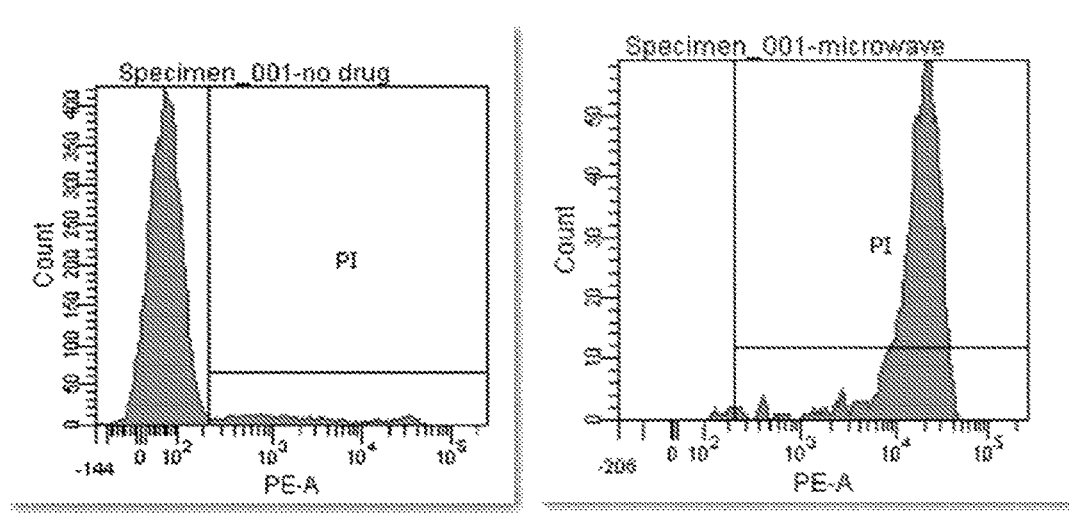

Cells incubated in the absence of drug were 92.8% viable, and cells exposed to 95° C. heat for 1 minute (positive control for dead cells) were 2.8% viable (FIG. 4b).

Gating was established based on viable cells cultured in the absence of drug (FIG. 4b). Histograms and scatter plots are representative data from at least 3 independent experiments conducted with pooled cells from 8 donors. Graphs (E, F) are mean and standard deviations compiled from each independent experiment.

FIG. 4B is a histogram showing the results of flow cytometry studies using Propidium Iodide stain quantified with the phycoerythrin (PE-A) channel. Only dead/dying cells will stain positive for Propidium Iodide, therefore only dead/dying cells will be detected by the PE channel using flow cytometry. Living, viable cells will not be stained by Propidium Iodide, therefore they will not be detected in the PE channel. Cells incubated in the absence of drug were 92.8% viable (meaning that 92.8% of cells did not uptake Propidium Iodide stain), and the positive control of cells exposed to 95° C. heat for 1 minute were 2.8% viable (meaning that 97.2% of these cells stained positive for Propidium Iodide and are therefore dead) (B). The data is shown in terms of total percent of cells in each sample, where gating was established based on viable cells cultured in the absence of drug.

Figure 4C:
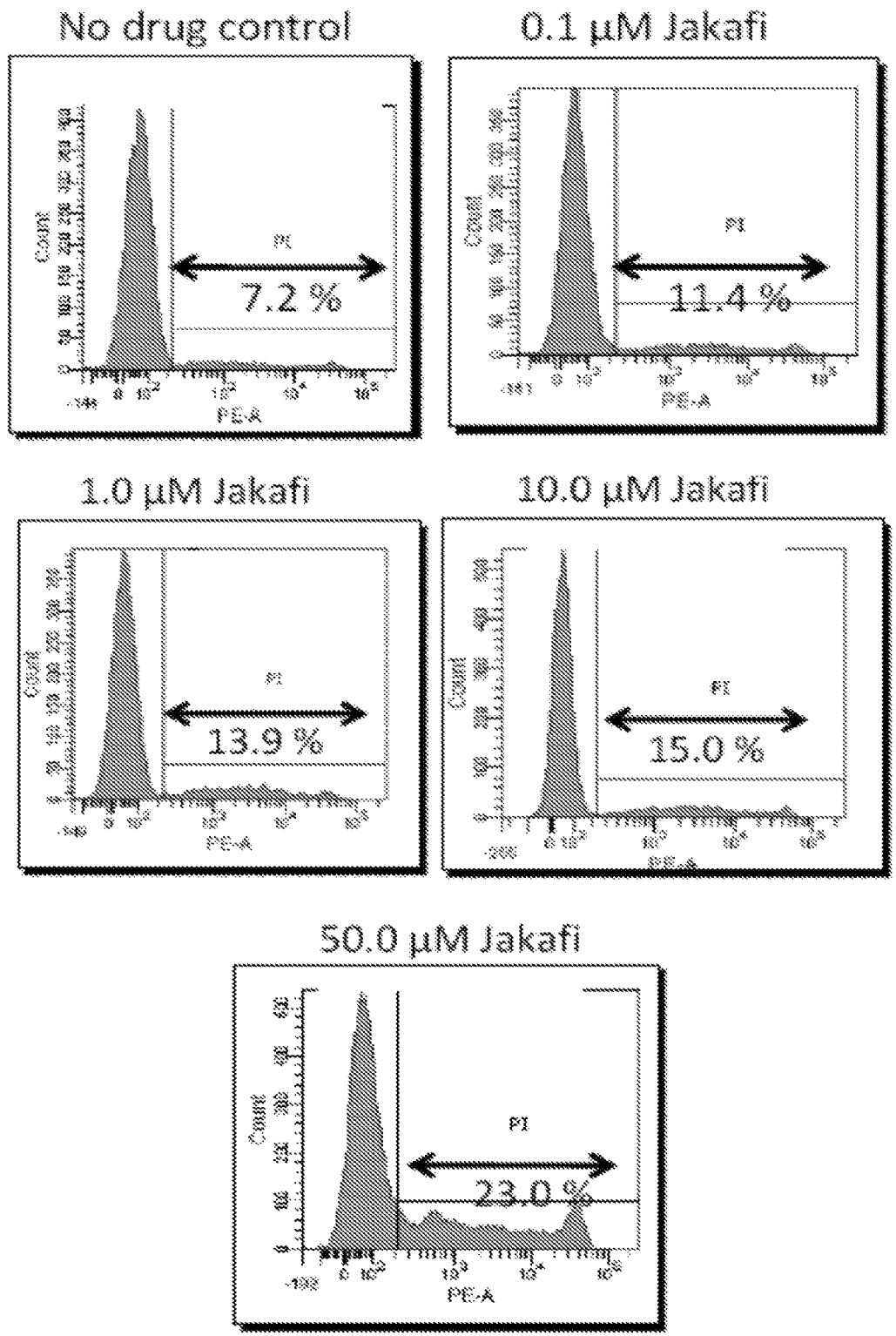

FIG. 4c shows histograms comparing the cell viability for cells exposed to Jakafi and to no drug (i.e., controls) for concentrations of 0.1 µM Jakafi, 1.0 µM Jakafi, 10 µM Jakafi, and 50 µM Jakafi.

Figure 4D:
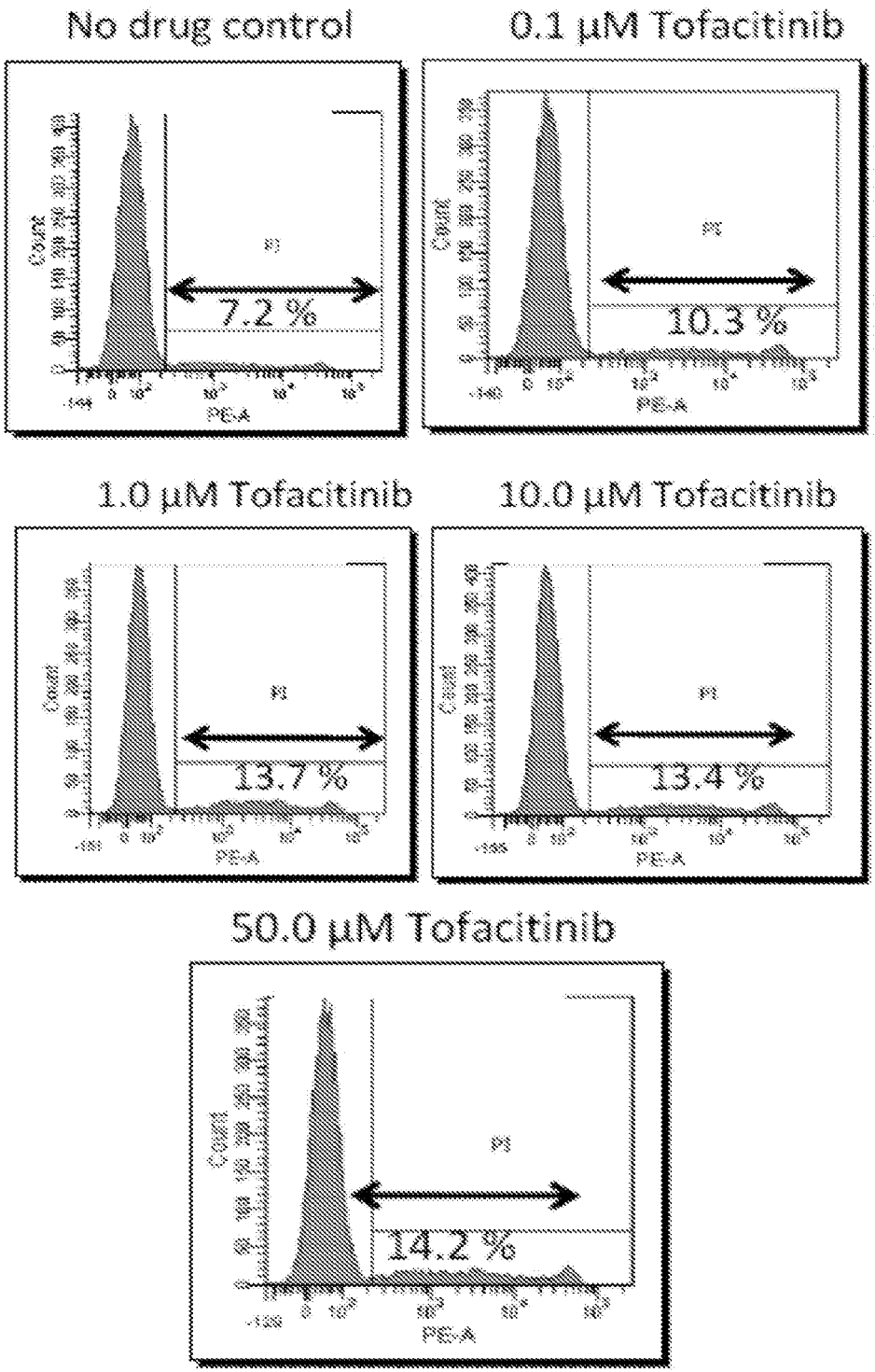

FIG. 4d shows histograms comparing the cell viability for cells exposed to Tofacitinib and to no drug (i.e., controls) for concentrations of 0.1 µM Tofacitinib, 1.0 µM Tofacitinib, 10 µM Tofacitinib, and 50 µM Tofacitinib.

Figure 4E:
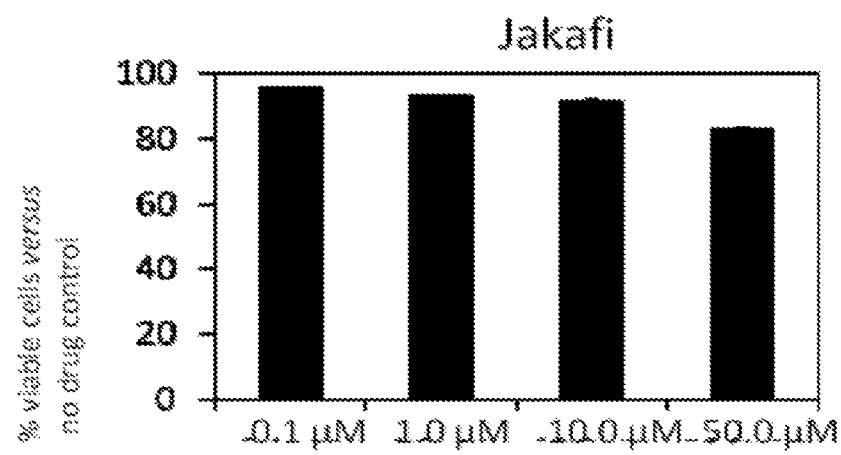
Figure 4F:
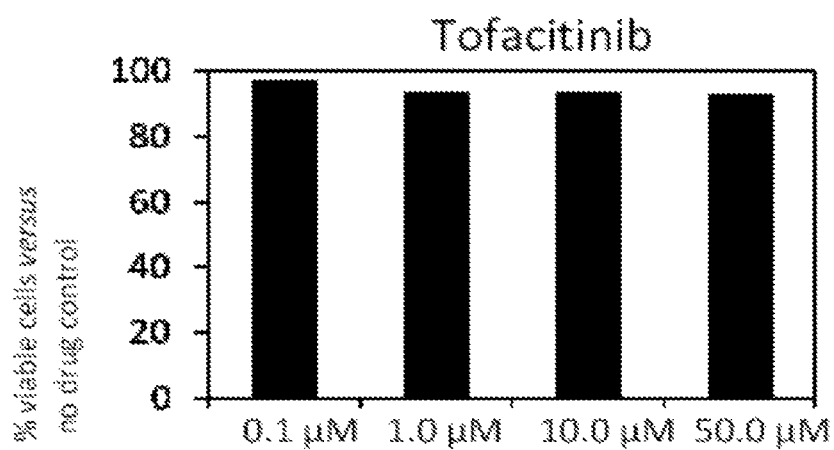

FIGS. 4e and 4f are charts showing the mean and standard deviations from the experiments shown in FIGS. 4c (Jakafi) and 4d (Tofacitinib), respectively.

The data showed that Jakafi did not significantly reduce viability versus no drug controls for all concentrations tested with the exception of 50 µM (p<0.05)(FIG. 4c). The data also showed that Tofacitinib did not significantly reduce viability versus no drug controls for all concentrations tested (FIG. 4d).

Example 21: Viability of Primary Human Lymphocytes Exposed to Various Concentrations of Jakafi or Tofacitinib The antiviral potency of Jakafi and Tofacitinib was evaluated in primary rhesus macaque lymphocytes and macrophages using the techniques discussed above. The antiviral potency was approximately 0.4 µM ($EC_{50}$) and 4.0 µM ($EC_{90}$) for both Jakafi and Tofacitinib in primary rhesus macaque macrophages. The antiviral potency was 0.09±0.1 ($EC_{50}$) and 1.3±0.8 ($EC_{90}$) in primary rhesus macaque macrophages. An AZT control demonstrated antiviral potency as expected. The data (Shown in Table 5 below) are mean and standard deviations from at least three independent experiments.

TABLE 5

| Drug | Acute infection in rhesus macaque macrophages $EC_{50}$ (µM) | Acute infection in rhesus macaque macrophages $EC_{90}$ (µM) | Acute infection in rhesus macaque lymphocytes $EC_{50}$ (µM) | Acute infection in rhesus macaque lymphocytes $EC_{90}$ (µM) |
|---|---|---|---|---|
| Jakafi | 0.4 ± 0.2 | 4.2 ± 1.3 | 0.09 ± 0.1 | 1.3 ± 0.8 |
| Tofacitinib | 0.3 ± 0.2 | 3.1 ± 0.9 | 0.3 ± 0.1 | 2.9 ± 0.5 |
| AZT | 0.08 ± 0.1 | 0.9 ± 0.7 | 0.002 ± 0.001 | 0.03 0.02 |

Example 22: Synergistic Antiviral Potency for Co-Administration of Jakafi and Tofacitinib in Primary Human Lymphocytes and Macrophages The synergistic antiviral potentency for co-administration of Jakafi and Tofacitinib was evaluated in primary human lymphocytes and macrophages, using the techniques described above.

Figure 5A:
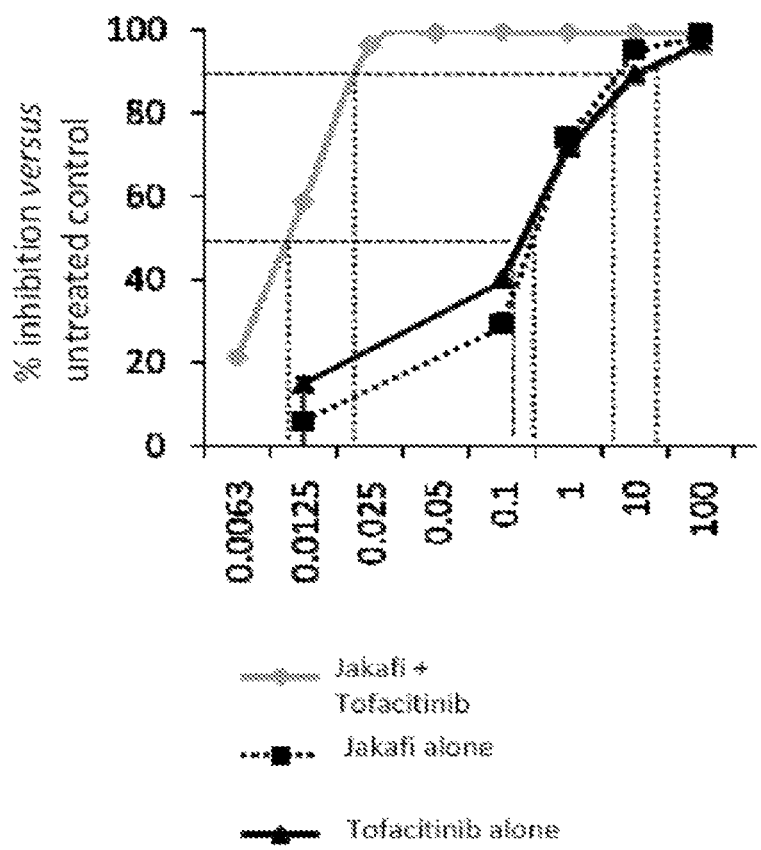
FIGS. 5a and 5b are charts showing the percent inhibition of HIV-1 replication versus untreated control for the co-administration of Jakafi and Tofacitinib in primary human lymphocytes (FIG. 5a) and macrophages (FIG. 5b). The data is shown in terms of percent inhibition (%) on the Y axis versus drug concentration (μM) on the X axis.
Figure 5B:
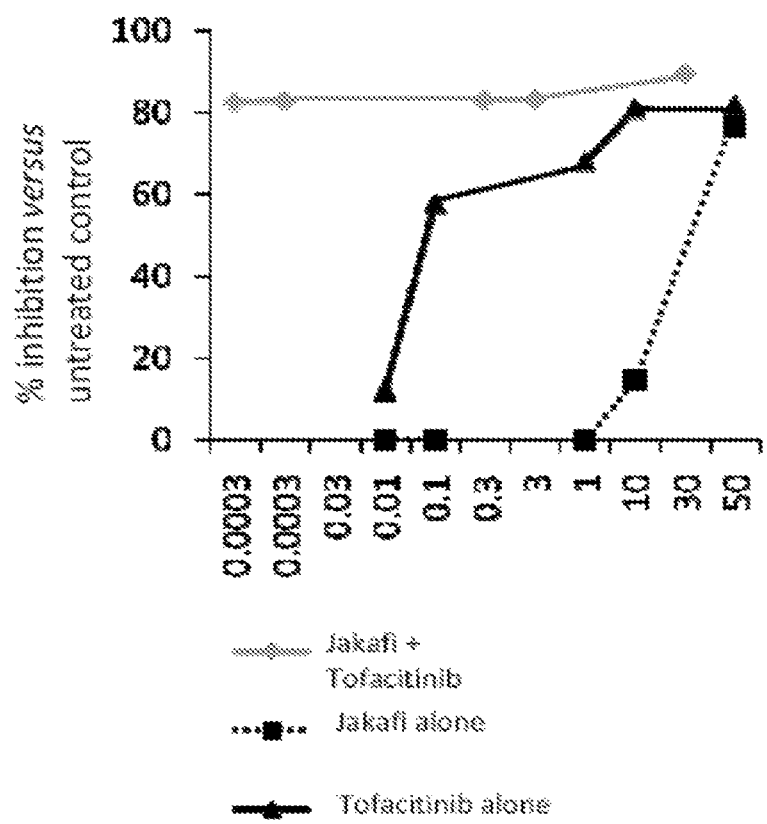

Co-administration of Jakafi and Tofacitinib at a ratio of 1:4 (lymphocytes) or 1:1 (macrophages) demonstrated synergistic antiviral potency, as calculated by CalcuSyn (Biosoft, Inc., Cambridge, Great Britain). The results are shown in FIGS. 5a and 5b. $EC_{50}$ and $EC_{90}$ in lymphocytes were decreased by 5-fold and 117-fold, respectively (dotted lines, FIG. 5a). $EC_{50}$ and EC90 were markedly decreased in macrophages (FIG. 5b).

Example 23: Antiviral Potency and of Jakafi and Tofacitinib Against Various NRTI-Resistant HIV-1 in Primary Human Lymphocytes The antiviral potency of Jakafi and Tofacitinib against various NRTI-resistant HIV-1 was evaluated in primary human lymphocytes using the techniques described above.

The antiviral potency of Jakafi and Tofacitinib was not significantly different for wild-type HIV-1xxLAI versus that of HIV-1 containing mutations K65R, M184V, L74V, A62V/V75I/F77L/F116Y/Q151M, or 4×AZT (D67N/K70R/T215Y/K219Q). Various controls for each mutation demonstrated potency or resistance as expected. Efavirenz (EFV) was similarly potent across all NRTI resistant strains as expected. Data are mean and standard deviations calculated from at least 4 independent experiments, with pooled cells from 8 donors and duplicates in each experiment.

The $EC_{50}$ data is shown in Table 6, and the $EC_{90}$ data is shown in Table 7.

TABLE 6

| | ($EC_{50}$) | | | | |
|---|---|---|---|---|---|
| | AZT | (−)FTC | 3TC | Tofacitinib | Jakafi |
| xxLAI | 0.03 ± 0007 | 0.09 ± 0.02 | 0.8 ± 0.4 | 2.6 ± 1.3 | 0.3 ± 0.3 |
| M184V | 0.01 ± 0.02 | 10.1 ± 7.3 | >10 | 1.6 ± 0.7 | 0.3 ± 0.3 |
| K65R | 0.04 ± 0.02 | 0.5 ± 0.4 | 2.5 ± 3.0 | 1.8 ± 0.8 | 0.2 ± 0.3 |
| L74V | 0.02 ± 0.02 | 0.2 ± 0.2 | 0.6 ± 0.8 | 0.9 ± 1.0 | 0.1 ± 0.2 |
| A62V/V75I/F77L/F116Y/Q151M | 4.6 ± 7.7 | 0.4 ± 0.3 | 0.5 ± 0.7 | 0.2 ± 0.2 | 0.03 ± 0.02 |
| 4xAZT (D67N/K70R/T215Y/K219Q) | 0.1 ± 0.1 | 0.2 ± 0.1 | 0.7 ± 0.8 | 0.3 ± 0.2 | 0.09 ± 0.1 |

| | D4T | ddI | EFV | TDF |
|---|---|---|---|---|
| xxLAT | 1.0 ± 0.5 | 11.5 ± 6.6 | 0.02 ± 0.03 | 0.2 ± 0.2 |
| M184V | 0.6 ± 0.8 | 11.5 ± 9.1 | 0.01 ± 0.006 | 0.09 ± 0.03 |
| K65R | 1.5 ± 0.6 | 21.2 ± 18.3 | 0.007 | 0.4 ± 0.1 |
| L74V | 0.9 ± 0.8 | 13.2 ± 8.5 | 0.06 ± 0.07 | 0.2 ± 0.1 |
| A62V/V75I/F77L/F116Y/Q151M | 6.8 ± 05.7 | 40.5 ± 52.1 | 0.2 ± 0.3 | 0.7 ± 0.8 |
| 4xAZT (D67N/K70R/T215Y/K219Q) | 27.8 ± 37.1 | 35.5 ± 31.0 | 0.07 ± 0.04 | 0.07 ± 0.04 |

TABLE 7

| | ($EC_{90}$) | | | | |
|---|---|---|---|---|---|
| | AZT | (−)FTC | 3TC | Tofacitinib | Jakafi |
| xxLAI | 0.1 ± 0.08 | 0.8 ± 0.4 | 3.1 ± 1.2 | 28.4 ± 16.7 | 6.1 ± 7.6 |
| M184V | 0.02 ± 0.01 | 41.3 ± 29.3 | >10 | 27.1 ± 15.7 | 3.2 ± 2.3 |
| K65R | 0.3 ± 0.1 | 2.4 ± 1.4 | 6.0 ± 5.3 | 81.2 ± 26.7 | 8.5 ± 8.1 |
| L74V | 0.2 ± 0.1 | 1.3 ± 1.0 | 2.9 ± 2.9 | 47.7 ± 45.3 | 3.2 ± 2.6 |
| A62V/V75I/F77L/F116Y/Q151M | 41.2 ± 50.2 | 2.1 ± 1.6 | 2.7 ± 1.7 | 8.9 ± 8.8 | 1.5 ± 1.5 |
| 4xAZT (D67N/K70R/T215Y/K219Q) | 53.3 ± 66.1 | 1.2 ± 0.1 | 3.4 ± 1.1 | 17.1 ± 4.5 | 2.4 ± 2.0 |

| | D4T | ddI | EFV | TDF |
|---|---|---|---|---|
| xxLAI | 6.4 ± 0.4 | 55.4 ± 23.0 | 0.2 ± 0.3 | 0.9 ± 0.8 |
| M184V | 2.6 ± 2.5 | 44.9 ± 26.2 | 0.08 ± 0.08 | 0.5 ± 0.3 |
| K65R | 7.9 ± 0.3 | 86.7 ± 0.8 | 0.02 ± 0.01 | 1.6 ± 0.5 |
| L74V | 9.8 ± 2.4 | 80.9 ± 16.6 | 0.2 ± 0.3 | 0.2 ± 0.1 |
| A62V/V75I/F77L/F116Y/Q151M | 70.3 ± 51.4 | 83.5 ± 28.6 | 0.44 ± 0.6 | 3.6 ± 2.2 |
| 4xAZT (D67N/K70R/T215Y/K219Q) | 53.2 ± 66.3 | 77.1 ± 32.4 | 0.2 ± 0.2 | 1.2 ± 1.1 |

Example 24: Fold Increase 50 ($FI_{50}$) and Fold Increase 90 ($FI_{90}$) for Jakafi and Tofacitinib Against Various NRTI-Resistant HIV-1 in Primary Human Lymphocytes The fold increase 50 ($FI_{50}$) and fold increase 90 ($FI_{90}$) for Jakafi and Tofacitinib against various NRTI-resistant HIV-1 was evaluated in primary human lymphocytes, using the techniques described above. $FI_{50}$ is the ratio of $EC_{50}$ against mutant virus:$EC_{50}$ against wild-type xxLAI. $FI_{90}$ is the ratio of $EC_{90}$ against mutant virus:$EC_{90}$ against wild-type xxLAI. There was not significant increase in $F_{50}$ or $FI_{90}$ for Jakafi or Tofacitinib treated cells. Controls of AZT, (−)FTC, 3TC, d4T, ddI, Efavirenz (EFV), TDF demonstrated sensitivity or resistance as expected.

The data is shown below in Table 8 ($F_{50}$) and Table 9 ($FI_{90}$)

TABLE 8

| | ($FI_{50}$) | | | | |
|---|---|---|---|---|---|
| | AZT | (−)FTC | 3TC | Tofacitinib | Jakafi |
| M184V | 0.5 | 117 | 13.3 | 0.6 | 1.3 |
| K65R | 1.5 | 5.5 | 3.3 | 0.7 | 0.8 |
| L74V | 0.8 | 2 | 0.7 | 0.4 | 0.5 |
| A62V/V75VF77L/F116Y/Q151M | 184 | 4.2 | 0.6 | 0.1 | 0.1 |
| 4xAZT (D67N/K70R/T215Y/K219Q) | 5.2 | 2 | 0.9 | 0.1 | 0.3 |

| | D4T | ddI | EFV | TDF |
|---|---|---|---|---|
| M184V | 0.6 | 1 | 0.5 | 0.6 |
| K65R | 1.5 | 1.8 | 0.3 | 2.2 |

TABLE 8-continued

| | ($FI_{50}$) | | | |
|---|---|---|---|---|
| L74V | 0.9 | 1.1 | 2.6 | 1.4 |
| A62V/V75I/F77L/F116Y/Q151M | 6.9 | 3.5 | 7.7 | 3.9 |
| 4xAZT (D67N/K70R/T215Y/K219Q) | 28.1 | 3.1 | 3.1 | 1.3 |

TABLE 9

| | ($FI_{90}$) | | | | |
|---|---|---|---|---|---|
| | AZT | (−)FTC | 3TC | Tofacitinib | Jakafi |
| M184V | 0.13 | 50 | 3.2 | 1.0 | 0.5 |
| K65R | 1.5 | 2.9 | 1.9 | 2.9 | 1.4 |
| L74V | 0.9 | 1.6 | 0.9 | 1.7 | 0.5 |
| A62V/V75I/F77L/F116Y/Q151M | 242 | 2.5 | 0.9 | 0.3 | 0.3 |
| 4xAZT (D67N/K70R/T215Y/K219Q) | 314 | 1.4 | 1.1 | 0.61 | 0.4 |

| | D4T | ddI | EFV | TDF |
|---|---|---|---|---|
| M184V | 0.4 | 0.8 | 0.4 | 0.6 |
| K65R | 1.2 | 1.6 | 0.1 | 1.7 |
| L74V | 1.5 | 1.1 | 1.1 | 1.2 |
| A62V/V75I/F77L/F116Y/Q151M | 11 | 1.5 | 2 | 3.9 |
| 4xAZT (D67N/K70R/T215Y/K219Q) | 8.3 | 1.4 | 1 | 1.3 |

The data is also shown in FIGS. 6a and 6b. Jakafi and Tofacitinib did not display a significant difference in $FI_{50}$ (FIG. 6a) or $FI_{90}$ (FIG. 6b) versus wild type HIV-1xxLAI for HIV-1 containing M184V, K65R, L74V, A62V/V75I/F77L/F116Y/Q151M, or 4xAZT (D67N/K70R/T215Y/K219Q) containing mutations.

Example 25: Effect of Various Jak Inhibitors on Proliferation and Viability of PHA or PHA+IL-2 Stimulated Primary Human Lymphocytes The effect of various Jak inhibitors on proliferation and viability of PHA or PHA+IL-2 stimulated primary human lymphocytes was evaluated using the techniques described above. For PHA stimulated lymphocytes, viability and proliferation were not significantly different than that of cell exposed to media alone for all concentrations of either Jakafi or Tofacitinib (FIG. 7a and FIG. 7c). For PHA+IL-2 stimulated lymphocytes, viability was not significantly different than that of cells exposed to media alone for all concentrations of either Jakafi or Tofacitinib (FIG. 7b), however proliferation was significantly inhibited by 1.0 μM of Jakafi or Tofacitinib (FIG. 7d).

For all experiments, cells were incubated with media alone or drug-containing medium for 5 days prior to assessment of cell count and viability. Data are mean and standard deviations for at least three independent experiments conducted with at least 4 pooled donors, and duplicates within each experiment. The dotted bar represents mean cell count or viability for cells maintained in drug-free medium.

Example 26: Tofacitinib and Jakafi Inhibit Reactivation of Latent HIV-1

The ability of Tofacitinib and Jakafi to inhibit reactivation of latent HIV-1 was evaluated using the techniques described in Bosque and Planelles (2009) Induction of HIV-1 latency and reactivation in primary memory CD4+ T cells; Blood 113: 58-65, and Jordan et al, (2003) HIV reproducibly establishes a latent infection after acute infection of T cells in vitro; The EMBO Journal, Vol. 22 No. 8 pp. 1868±1877. Tofacitinib (diamonds) and Jakafi (squares) inhibit reactivation of latent HIV-1 in a primary central memory-based T cell latency model (FIG. 8a) and in the J-Lat latency T cell system (FIG. 8b). Jakafi was the more potent inhibitor across both systems, and inhibited >50% of reactivation at concentrations found during steady-state or $C_{max}$ in vivo (shaded boxes).

The ability of Tofacitinib and Jakafi to inhibit reactivation of latent HIV-1 was also evaluated in primary human macrophages. Primary human monocytes were obtained by elutriation and differentiated to terminally differentiated macrophages in the presence of m-CSF for 5 days. Cells were subsequently infected with VSV-pseudotyped HIV-1 (envelope region), allowing for 100% infection rate of cultures. Cells were further cultured for 40 days until cultures were no longer producing HIV-1. At this time, all macrophages are now resting, latently infected cells. 41 days post infection, 10 ng/ml phorbol myristate acetate (PMA) was applied to the latently infected macrophages for 24 hr in either the absence of drug (positive control), or in the presence of 1.0 or 10.0 μM Jakafi or Tofacitinib. After 24 hr, both PMA and drug containing mediums were removed, and cells were cultured in media alone. Samples were taken at various days post reactivation and extracellular, reactivated virus production was quantified using p24 ELISA. Results are reported as percent inhibition of reactivation of latent HIV-1 versus no drug control. The results are shown in FIGS. 9a (Tofacitinib) and 9b (Jakafi). Both Tofacitinib and Jakafi inhibit reactivation of latent HIV-1 in primary human macrophages when drug is applied to cells during reactivation, but removed thereafter. Tofacitinib inhibits~40% of reactivation while Jakafi inhibits~35% of reactivation within 72 hr post reactivation.

Example 27: Tofacitinib and Jakafi Inhibit a Pro-HIV Cytokine (IFN-α) Induced Activation of the Jak-STAT Pathway Tofacitinib and Jakafi inhibit a pro-HIV cytokine (IFN-a) induced activation of the Jak-STAT pathway. Jakafi and Tofacitinib inhibit IFN-α induced phosphorylation of STAT1, 3, and 5 in primary CD4+ T lymphocytes at submicromolar concentrations (A, B, C).

Example 28: Tofacitinib and Jakafi Inhibit a Pro-HIV Cytokine (IFN-α) Induced Activation of the Jak-STAT Pathway The ability of Tofacitinib and Jakafi to inhibit a pro-HIV cytokine (IFN-α) induced activation of the Jak-STAT pathway was evaluated using techniques described above. Jakafi and Tofacitinib inhibit IFN-α induced phosphorylation of STAT1, 3, and 5 in primary CD4+T lymphocytes at submicromolar concentrations, as shown below in Table 10. Both drugs also inhibit pSTAT1, 3, and 5 with similar $EC_{50/90}$ in CD8 T cells and CD14 monocytes (data not shown).

TABLE 10

| Drug | EC$_{50}$/$_{90}$ pSTAT1 (μM) | EC$_{50}$/$_{90}$ pSTAT3 (μM) | EC$_{50}$/$_{90}$ pSTAT5 (μM) |
|---|---|---|---|
| (Tofacitinib/Xalijenz) | <0.01/0.01 | 0.02/0.9 | <0.01/0.01 |
| (Jakafi) | <0.01/<0.01 | <0.01/0.01 | <0.01/<0.01 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references cited herein are incorporated by reference in their entirety for all purposes.

Example 29: Jak Inhibitors Tofacitinib and Ruxolitinib Reduce the Frequency of Cells Harboring Integrated Viral DNA and IL-15-Induced Reactivation of Latent HIV-1 in CD4 T Cells (FIG. 11)

FIG. 11 shows that tofacitinib and ruxolitinib block reservoir reactivation and decay the size of the HIV reservoir in CD4 T cells from HIV-infected individuals, both alone and in the presence of HAART.

Example 30: Jak Inhibitors Block Bystander Infection in Primary CD4 T Cells

FIG. 12 shows that ruxolitinib blocks bystander CD4 T cells from becoming infected by their neighbor cells, thereby preventing seeding and expansion of the HIV reservoir, and also preventing establishment of the HIV reservoir.

Example 31: Jak Inhibitor can Block the HIV Establishment, Maintenance, Lifespan, and HIV-Induced Inflammatory Events (HIV-Associated Neurocognitive Impairment System) in Primary Human Macrophages and Monocytes FIG. 13 shows that baricitinib blocks HIV infection, HIV-induced inflammation and activation, HIV reactivation, and decays the lifespan of the HIV reservoir in primary human macrophages and monocytes, which are resident cells of the CNS. These data show that baricitinib blocks key events that drive HIV-associated neurocognitive dysfunction (HAND) in monocytes and macrophages.

The invention claimed is:

1. A method for treating or preventing an AIDS-related neurological disorder, comprising administering to a patient in need thereof an effective amount of a compound of Formula A:

Formula A wherein:
or the pharmaceutically acceptable salt thereof; wherein $R^1$ is a group of the formula wherein y is 0, 1 or 2;
$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or
$R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl $(C_1-C_6)$alkyl, $(C_1-C_6)$acylamino, $(C_1-C_6)$acylamino $(C_1-C_6)$alkyl, $(C_1-C_6)$alkoxy$(C_1-C_6)$acylamino, amino $(C_1-C_6)$acyl, amino$(C_1-C_6)$acyl$(C_1-C_6)$alkyl, $(C_1-C_6)$ alkylamino$(C_1-C_6)$acyl, $((C_1-C_6)$alkyl$)_2$amino$(C_1-C_6)$ acyl, $R^{15}R^{16}N—CO—O—$, $R^{15}R^{16}N—CO—(C_1-C_6)$ alkyl, $(C_1-C_6)$alkyl-S(O)$_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}(C_1-C_6)$alkyl wherein m is 0, 1 or 2 and $R^{15}$ and $R^{16}$ are each independently selected from hydrogen or $(C_1-C_6)$alkyl; or a group of the formula wherein a is 0, 1, 2, 3 or 4;
b, c, e, f and g are each independently 0 or 1;
d is 0, 1, 2, or 3;
X is S(O)$_n$ wherein n is 0, 1 or 2; oxygen, carbonyl or —C(=N-cyano)-;
Y is S(O)$_n$ wherein n is 0, 1 or 2; or carbonyl; and
Z is carbonyl, C(O)O—, C(O)NR— or S(O)$_n$ wherein n is 0, 1 or 2;
$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$ alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$ alkyl, $(C_1-C_6)$alkylamino$(C_1-C_6)$acyl, $((C_1-C_6)$alkyl$)_2$ amino$(C_1-C_6)$acyl, $R^{15}R^{16}N—CO—O—$, $R^{15}R^{16}N—CO—(C_1-C_6)$alkyl, $R^{15}C(O)NH$, $R^{15}OC(O)NH$, $R^{15}NHC(O)NH$, $(C_1-C_6)$alkyl-S(O)$_m$, $(C_1-C_6)$alkyl-S (O)$_m$—$(C_1-C_6)$alkyl, $R^{15}R^{16}NS(O)_m$, $R^{15}R^{16}NS(O)_m$ ($C_1$-$C_6$)alkyl, $R^{15}S(O)_mR^{16}N$, $R^{15}S(O)_mR^{16}N(C_1$-$C_6)$alkyl wherein m is 0, 1 or 2 and $R^{15}$ and $R^{16}$ are each independently selected from hydrogen or ($C_1$-$C_6$)alkyl;

$R^2$ and $R^3$ are each independently selected from the group consisting of hydrogen, deuterium, amino, halo, hydroxy, nitro, carboxy, ($C_2$-$C_6$)alkenyl, ($C_2$-$C_6$)alkynyl, trifluoromethyl, trifluoromethoxy, ($C_1$-$C_6$)alkyl, ($C_1$-$C_6$)alkoxy, ($C_3$-$C_{10}$)cycloalkyl wherein the alkyl, alkoxy or cycloalkyl groups are optionally substituted by one to three groups selected from halo, hydroxy, carboxy, amino ($C_1$-$C_6$)alkylthio, ($C_1$-$C_6$)alkylamino, (($C_1$-$C_6$)alkyl)$_2$amino, ($C_5$-$C_9$)heteroaryl, ($C_2$-$C_9$)heterocycloalkyl, ($C_3$-$C_9$)cycloalkyl or ($C_6$-$C_{10}$)aryl; or $R^2$ and $R^3$ are each independently ($C_3$-$C_{10}$)cycloalkyl, ($C_3$-$C_{10}$)cycloalkoxy, ($C_1$-$C_6$)alkylamino, (($C_1$-$C_6$)alkyl)$_2$amino, ($C_6$-$C_{10}$)arylamino, ($C_1$-$C_6$)alkylthio, ($C_6$-$C_{10}$)arylthio, ($C_1$-$C_6$)alkylsulfinyl, ($C_6$-$C_{10}$)arylsulfinyl, ($C_1$-$C_6$)alkylsulfonyl, ($C_6$-$C_{10}$)arylsulfonyl, ($C_1$-$C_6$)acyl, ($C_1$-$C_6$)alkoxy-CO—NH—, ($C_1$-$C_6$) alkylamino-CO—, ($C_5$-$C_9$)heteroaryl, ($C_2$-$C_9$) heterocycloalkyl or ($C_6$-$C_{10}$)aryl wherein the heteroaryl, heterocycloalkyl and aryl groups are optionally substituted by one to three halo, ($C_1$-$C_6$)alkyl, ($C_1$-$C_6$)alkyl-CO—NH—, ($C_1$-$C_6$)alkoxy-CO—NH—, ($C_1$-$C_6$)alkyl-CO—NH—($C_1$-$C_6$)alkyl, ($C_1$-$C_6$)alkoxy-CO—NH—($C_1$-$C_6$)alkyl, ($C_1$-$C_6$)alkoxy-CO—NH—($C_1$-$C_6$)alkoxy, carboxy, carboxy($C_1$-$C_6$)alkyl, carboxy ($C_1$-$C_6$)alkoxy, benzyloxycarbonyl($C_1$-$C_6$)alkoxy, ($C_1$-$C_6$)alkoxycarbonyl($C_1$-$C_6$)alkoxy, ($C_6$-$C_{10}$)aryl, amino, amino($C_1$-$C_6$)alkyl, ($C_1$-$C_6$)alkoxycarbonylamino, ($C_6$-$C_{10}$)aryl($C_1$-$C_6$)alkoxycarbonylamino, ($C_1$-$C_6$)alkylamino, (($C_1$-$C_6$)alkyl)$_2$amino, ($C_1$-$C_6$)alkylamino($C_1$-$C_6$)alkyl, (($C_1$-$C_6$)alkyl)$_2$amino($C_1$-$C_6$) alkyl, hydroxy, ($C_1$-$C_6$)alkoxy, carboxy, carboxy($C_1$-$C_6$)alkyl, ($C_1$-$C_6$)alkoxycarbonyl, ($C_1$-$C_6$) alkoxycarbonyl($C_1$-$C_6$)alkyl, ($C_1$-$C_6$)alkoxy-CO—NH—, ($C_1$-$C_6$)alkyl-CO—NH—, cyano, ($C_5$-$C_9$) heterocycloalkyl, amino-CO—NH—, ($C_1$-$C_6$) alkylamino-CO—NH—, (($C_1$-$C_6$)alkyl)$_2$amino-CO—NH—, ($C_6$-$C_{10}$)arylamino-CO—NH—, ($C_5$-$C_9$) heteroarylamino-CO—NH—, ($C_1$-$C_6$)alkylamino-CO—NH—($C_1$-$C_6$)alkyl, (($C_1$-$C_6$)alkyl)$_2$amino-CO—NH—($C_1$-$C_6$)alkyl, ($C_6$-$C_{10}$)arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$) alkylsulfonylamino, ($C_1$-$C_6$)alkylsulfonylamino($C_1$-$C_6$)alkyl, ($C_6$-$C_{10}$)arylsulfonyl, ($C_6$-$C_{10}$) arylsulfonylamino, ($C_6$-$C_{10}$)arylsulfonylamino($C_1$-$C_6$) alkyl, ($C_1$-$C_6$)alkylsulfonylamino, ($C_1$-$C_6$) alkylsulfonylamino($C_1$-$C_6$)alkyl, ($C_5$-$C_9$)heteroaryl or ($C_2$-$C_9$)heterocycloalkyl;

or of Formula B:

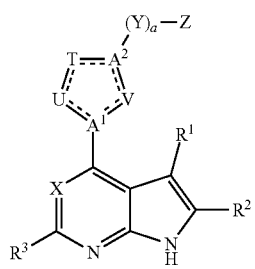

Formula B including pharmaceutically acceptable salt forms or prodrugs thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—($C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—($C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR_c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$alkyl)$R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $N_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl))$R^b$, and $S(O)_2NR^cR^d$;

wherein when Z is H, n is 1;

or the —$(Y)_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$ $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —$(W)_m$-Q;

W is $C_{1-8}$ alkylenyl, $C_{2-8}$ alkenylenyl, $C_{2-8}$ alkynylenyl, O, S, C(O), $C(O)NR^{c'}$, C(O)O, OC(O), $OC(O)NR^{c'}$, $NR^{c'}$, $NR^{c'}C(O)NR^{d'}$, S(O), $S(O)NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^cR^{d'}$, $C(O)OR^{a'}$, $OC(O)R^{b'}$, $OC(O)NR^cR^{d'}$, NR$^{c'}$R$^{d'}$, NR$^{c'}$C(O)R$^{b'}$, NR$^{c'}$C(O)NR$^{c'}$R$^{d'}$, NR$^{c'}$C(O)OR$^{a'}$, S(O)R$^{b'}$, S(O)NR$^{c'}$R$^{d'}$, S(O)$_2$R$^{b'}$, NR$^{c'}$S(O)$_2$R$^{b'}$, and S(O)$_2$NR$^{c'}$R$^{d'}$;

Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$, NR$^{c''}$S(O)R$^{b''}$, NR$^{c''}$S(O)$_2$R$^{b''}$, S(O)R$^{b''}$, S(O)NR$^{c''}$R$^{d''}$, S(O)$_2$R$^{b''}$, and S(O)$_2$NR$^{c''}$R$^{d''}$;

R$^1$, R$^2$, R$^3$, and R$^4$ are independently selected from H, halo, C$_{1-4}$ alkyl, C$_{2-4}$ alkenyl, C$_{2-4}$ alkynyl, C$_{1-4}$ haloalkyl, halosulfanyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$OC(O)R$^8$, OC(O)NR$^9$R$^{10}$, NR$^9$R$^{10}$, NR$^9$C(O)R$^8$, NR$^c$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$;

R$^5$ is H, halo, C$_{1-4}$ alkyl, C$_{2-4}$ alkenyl, C$_{2-4}$ alkynyl, C$_{1-4}$ haloalkyl, halosulfanyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$;

R$^6$ is H, C$_{1-4}$ alkyl, C$_{2-4}$ alkenyl, C$_{2-4}$ alkynyl, C$_{1-4}$ haloalkyl, OR$^7$, C(O)R$^8$, C(O)NR$^9$R$^{10}$, C(O)OR$^7$, S(O)R$^8$, S(O)NR$^9$R$^{10}$, S(O)$_2$R$^8$, or S(O)$_2$NR$^9$R$^{10}$;

R$^7$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^8$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^9$ and R$^{10}$ are independently selected from H, C$_{1-10}$ alkyl, C$_{1-6}$ haloalkyl, C$_{2-6}$ alkenyl, C$_{2-6}$ alkynyl, C$_{1-6}$ alkylcarbonyl, arylcarbonyl, C$_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or R$^9$ and R$^{10}$ together with the N atom to which they are attached form a 4-, 5-, 6- or 7-membered heterocycloalkyl group;

R$^{11}$ and R$^{12}$ are independently selected from H and -E$^1$-E$^2$-E$^3$-E$^4$;

D$^1$ and E$^1$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^2$ and E$^2$ are independently absent or independently selected from C$_{1-6}$ alkylene, C$_{2-6}$ alkenylene, C$_{2-6}$ alkynylene, (C$_{1-6}$ alkylene)$_r$-O—(C$_{1-6}$ alkylene)$_s$, (C$_{1-6}$ alkylene)$_r$-S—(C$_{1-6}$ alkylene)$_s$, (C$_{1-6}$ alkylene)$_r$-NR$^c$—(C$_{1-6}$ alkylene)$_s$, (C$_{1-6}$ alkylene)$_r$-CO—(C$_{1-6}$ alkylene)$_s$, (C$_{1-6}$ alkylene)$_r$-COO—(C$_{1-6}$ alkylene)$_s$, (C$_{1-6}$ alkylene)$_r$-CONR$^c$—(C$_{1-6}$ alkylene)$_s$, (C$_{1-6}$ alkylene)$_r$-SO—(C$_{1-6}$ alkylene)$_s$, (C$_{1-6}$ alkylene)$_r$-SO$_2$—(C$_{1-6}$ alkylene)$_s$, (C$_{1-6}$ alkylene)$_r$-SONR$^c$—(C$_{1-6}$ alkylene)$_s$, and (C$_{1-6}$ alkylene)$_r$-NR$^c$CONR$^f$—(C$_{1-6}$ alkylene)$_s$, wherein each of the C$_{1-6}$ alkylene, C$_{2-6}$ alkenylene, and C$_{2-6}$ alkynylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^3$ and E$^3$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^4$ and E$^4$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^a$, C(O)OR$^a$, OC(O)R$^b$OC(O)NR$^c$R$^d$, NR$^c$R$^d$, NR$^c$C(O)R$^b$, NR$^c$C(O)NR$^c$R$^d$, NR$^c$C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^b$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{a''}$ and R$^{a''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^{b'}$ and R$^{b''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^c$ and $R^d$ are independently selected from H, $Cy^1$, —($C_{1-6}$ alkyl)-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

or $R^c$ and $R^d$ together with the N atom to which they are attached form a 4-, 5-, 6- or 7-membered heterocycloalkyl group optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_2$-6 alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^i$ is H, CN, $NO_2$, or $C_{1-6}$ alkyl;

$R^e$ and $R^f$ are independently selected from H and $C_{1-6}$ alkyl;

$R^i$ is H, CN, or $NO_2$;

m is 0 or 1;

n is 0 or 1;

p is 0, 1, 2, 3, 4, 5, or 6;

q is 0, 1, 2, 3, 4, 5 or 6;

r is 0 or 1; and s is 0 or 1.

2. A method for treating or preventing an AIDS-related neurological disorder, comprising administering to a patient in need thereof an effective antiviral amount of a JAK inhibitors selected from the group consisting of CEP-701 (Lestaurtinib), AZD1480, LY3009104/INCB28050 Pacritinib/SB1518, VX-509, GLPG0634, INC424, R-348, CYT387, TG 10138, AEG 3482, 7-iodo-N-(4-morpholinophenyl)thieno[3,2-d]pyrimidin-2-amine, 7-(4-aminophenyl)-N-(4-morpholinophenyl)thieno[3,2-d]pyrimidin-2-amine, N-(4-(2-(4-morpholinophenylamino)thieno[3,2-d]pyrimidin-7-yl)phenyl)acryl amide, 7-(3-aminophenyl)-N-(4-morpholinophenyl)thieno[3,2-d]pyrimidin-2amine, N-(3-(2-(4-morpholinophenylamino)thieno[3,2-d]pyrimidin-7-yl)phen-yl)acrylamide, N-(4-morpholinophenyl)thieno[3,2-d]pyrimidin-2-amine, methyl 2-(4-morpholinophenylamino)thieno[3,2-d]pyrimidine-7-carboxylate, N-(4-morpholinophenyl)-5H-pyrrolo[3,2-d]pyrimidin-2-amine, 7-(4-amino-3-methoxyphenyl)-N-(4-morpholinophenyl)thieno[3,2-d]pyrimidin-2-amine, 4-(2-(4-morpholinophenylamino)thieno[3,2-d]pyrimidin-7-yl)benzenesulfonamide, N,Ndimethyl-3-(2-(4-morpholinophenylamino)thieno[3,2-d]pyrimidin-7-yl)benzenesulfonamide, 1-ethyl-3-(2-methoxy-4-(2-(4-morpholinophenylamino)thieno[3,2-d]pyrimidin-7-yl)phenyl)urea, N-(4-(2-(4-morpholinophenylamino)thieno[3,2-d]pyrimidin-7-yl)phenyl)metha-nesulfonamide, 2-methoxy-4-(2-(4-morpholinophenylamino)thieno[3,2-d]pyrimidin-7-yl)pheno-1,2-cyano-N-(3-(2-(4-morpholinophenylamino)thieno[3,2-d]pyrimidin-7-yl-)phenyl)acetamide, N-(cyanomethyl)-2-(4-morpholinophenylamino)thieno[3,2-d]pyrimidine-7-carboxamide, N-(3-(2-(4-morpholinophenylamino)thieno[3,2-d]pyrimidin-7-yl)phenyl)methanesulfonamide, 1-ethyl-3-(4-(2-(4-morpholinophenylamino)thieno[3,2-d]pyrimidin-7-yl)-2-(-trifluoromethoxy)phenyl)urea N-(3-nitrophenyl)-7-phenylthieno[3,2-d]pyrimidin2-amine, 7-iodo-N-(3-nitrophenyl)thieno[3,2-d]pyrimidin-2-amine, N1-(7-(2-ethylphenyl)thieno[3,2-d]pyrimidin-2-yl)benzene-1,3-diamine, N-tert-butyl-3-(2-(4-morpholinophenylamino)thieno[3,2-d]pyrimidin-7-yl)benzenesulfonamide, N1-(7-iodothieno[3,2-d]pyrimidin-2-yl)benzene-1,3-diamine, 7-(4-amino-3-(trifluoromethoxy)phenyl)-N-(4-morpholinophenyl)thieno[3,2-d]pyrimidin-2-amine, 7-(2-ethylphenyl)-N-(4-morpholinophenyl)thieno[3,2-d]pyrimidin-2-amine, N-(3-(2-(4-morpholinophenylamino)thieno[3,2-d]pyrimidin-7-yl)phenyl-)acetamide, N-(cyanomethyl)-N-(3-(2-(4-morpholinophenylamino)thieno[3,2-d]pyrimidin-7-yl)phenyl)methanesulfonamide, N-(cyanomethyl)-N-(4-(2-(4-morpholinophenylamino)thieno[3,2-d]pyrimidin-7-yl)phenyl)methanesulfonamide, N-(3-(5-methyl-2-(4-morpholinophenylamino)-5H-pyrrolo[3,2-5d]pyrimidin-7-yl)phenyl)methanesulfonamide, 4-(5-methyl-2-(4-morpholinophenylamino)-5Hpyrrolo[3,2-d]pyrimidin-7-yl)b-enzenesulfonamide, N-(4-(5-methyl-2-(4-morpholinophenylamino)-5H-pyrrolo[3,2-d]pyrimidin-7-yl)phenyl)methanesulfonamide, 7-iodo-N-(4-morpholinophenyl)-5H-pyrrolo[3,2-d]pyrimidin-2-amine, 7-(2-isopropylphenyl)-N-(4-morpholinophenyl)thieno[3,2-d]pyrimidin-2-amine, 7-bromo-N-(4-morpholinophenyl)thieno[3,2-d]pyrimidin-2-amine N7-(2-isopropylphenyl)-N2-(4-morpholinophenyl)thieno[3,2-d]pyrimidine-2,7-diamine, N7-(4-isopropylphenyl)-N2-(4-morpholinophenyl)thieno[3,2-d]pyrimidine-2,7-diamine, 7-(5-amino-2- methylphenyl)-N-(4-morpholinophenyl)thieno[3,2-d]pyrimidin-2-amine, N-(cyanomethyl)-4-(2-(4-morpholinophenylamino)thieno[3,2-d]pyrimidin-7-yl)benzamide, 7-iodo-N-(3-morpholinophenyl)thieno[3,2-d]pyrimidin-2-amine, 7-(4-amino-3-nitrophenyl)-N-(4-morpholinophenyl)thieno[3,2-d]pyrimidin-2-amine, 7-(2-methoxypyridin-3-yl)-N-(4-morpholinophenyl)thieno[3,2-d]pyrimidin-2-amine, (3-(7-iodothieno[3,2-d]pyrimidin-2-ylamino)phenyl)methanol, N-tert-butyl-3-(2-(3-morpholinophenylamino)thieno[3,2-d]pyrimidin-7-yl)benzenesulfonamide, N-tertbutyl-3-(2-(3-(hydroxymethyl)phenylamino)thieno[3,2-d]pyrimidin-7-yl)benzenesulfonamide, N-(4-morpholinophenyl)-7-(4-nitrophenylthio)-5Hpyrrolo[3,2-d]pyrimidin-2-amine, N-tert-butyl-3-(2-(3,4,5-trimethoxyphenylamino)thieno[3,2-d]pyrimidin-7-yl)benzenesulfonamide, 7-(4-amino-3-nitrophenyl)-N-(3,4-dimethoxyphenyl)thieno[3,2-d]pyrimidin-2-amine N-(3,4-dimethoxyphenyl)-7-(2-methoxypyridin-3-yl)thieno[3,2-d]pyrimidin-2-amine, N-tert-butyl-3-(2-(3,4-dimethoxyphenylamino)thieno[3,2-d]pyrimidin-7-yl)benzenesulfonamide, 7-(2-aminopyrimidin-5-yl)-N-(3,4-dimethoxyphenyl)thieno[3,2-d]pyrimidin-2-amine, N-(3,4-dimethoxyphenyl)-7-(2,6-dimethoxypyridin-3-yl)thieno[3,2-d]pyrimidin-2-amine, N-(3,4-dimethoxyphenyl)-7-(2,4-dimethoxypyrimidin-5-yl)thieno[3,2-d]pyrimidin-2-amine, 7-iodo-N-(4-(morpholinomethyl)phenyl)thieno[3,2-d]pyrimidin-2-amine, N-tert-butyl-3-(2-(4-(morpholinomethyl)phenylamino)thieno[3,2-d]pyrimidin-7-yl)2-cyano-N-(4-methyl-3-(2-(4-morpholinophenylamino)thieno[3,2-d]pyrimidin-7-yl)phenyl)acetamide, ethyl 3-(2-(4-morpholinophenylamino)thieno[3,2-d]pyrimidin-7-yl)benzoate, 7-bromo-N-(4-(2-(pyrrolidin-1-yl)ethoxy)phenyl)thieno[3,2-d]pyrimidin-2-amine, N-(3-(2-(4-(2-(pyrrolidin-1-yl)ethoxy)phenylamino)thieno[3,2-d]pyrimidin-7-yl)phenyl)acetamide, N-(cyanomethyl)-5 3-(2-(4-morpholinophenylamino)thieno[3,2-d]pyrimidin-7-yl-)benzamide, N-tert-butyl-3-(2-(4-morpholinophenylamino)thieno[3,2-d]pyrimidin-7-yl)benzamide, N-tert-butyl-3-(2-(4-(1-ethylpiperidin-4-yloxy)phenylamino)thieno[3,2-d]pyrimidin-7-yl)benzenesulfonamide, tert-butyl-4-(2-(4-(morpholinomethyl)phenylamino)thieno[3,2-d]pyrimidin-7-yl)-1H-pyrazole-1-carboxylate, 7-bromo-N-(4-((4-ethylpiperazin-1-yl)methyl)phenyl)thieno[3,2-d]pyrimidin-2-amine, N-tert-butyl-3-(2-(4-((4-ethylpiperazin-1-yl)methyl)phenylamino)thieno[3,-2-d]pyrimidin-7-yl)benzenesulfonamide, N-(4-((4-ethylpiperazin-1-yl)methyl)phenyl)-7-(1H-pyrazol-4-yl)thieno[3,2-d]pyrimidin-2-amine, N-(cyanomethyl)-3-(2-(4-(morpholinomethyl)phenylamino)thieno[3,2-d]pyrimidin-7-yl)benzamide, N-tert-butyl-3-(2-(4-(2-(pyrrolidin-1-yl)ethoxy)phenylamino)thieno[3,2-d]-pyrimidin-7-yl)benzenesulfonamide, tert-butylpyrrolidin-1-yl)ethoxy)phenylamino)thieno[3,2-d]pyrimidin-7-yl)benzylcarbamate, 3-(2-(4-(2-(pyrrolidin-1-yl)ethoxy)phenylamino)thieno[3,2-d]pyrimidin-7-yl)benzenesulfonamide, 7-(3-chloro-4-fluorophenyl)-N-(4-(2-(pyrrolidin-1-yl)ethoxy)phenyl)thieno-[3,2-d]pyrimidin-2-amine, tert-butyl 4-(2-(4-(1-ethylpiperidin-4-yloxy)phenylamino)thieno[3,2-d]pyrimidin-7-yl-)-1H-pyrazole-1-carboxylate, 7-(benzo[d][1,3]dioxol-5-yl)-N-(4-(morpholinomethyl)phenyl)thieno[3,2-d]pyrimidin-2-amine, tert-butyl 5-(2-(4-(morpholinomethyl)phenylamino)thieno[3,2-d]pyrimidin-7-yl)-1H-indole-1-carboxylate, 7-(2-aminopyrimidin-5-yl)-N-(4-(morpholinomethyl)phenyl)thieno[3,2-d]pyrimidin-2-amine, tert-butyl 4-(2-(4-(morpholinomethyl)phenylamino)thieno[3,2-d]pyrimidin-7-yl)-5,6-di-hydropyridine-1(2H)-carboxylate, tert-butylmorpholinomethyl)phenylamino)thieno[3,2-d]pyrimidin-7-yl)benzylcarbamate, N-(3-(2-(4-(morpholinomethyl)phenylamino)thieno[3,2-d]pyrimidin-7-yl)-phenyl)acetamide, N-(4-(2-(4-(morpholinomethyl)phenylamino)thieno[3,2-d]pyrimidin-7-yl)phenyl)acetamide, N-(3-(2-(4-(morpholinomethyl)phenylamino)thieno[3,2-d]pyrimidin-7-yl)phenyl)methanesulfonamide, 7-(4-(4-methylpiperazin-1-yl)phenyl)-N-(4-(morpholinomethyl)phenyl)thieno-[3,2-d]pyrimidin-2-amine, N-(2-methoxy-4-(2-(4-(morpholinomethyl)phenylamino)thieno[3,2-d]pyrimidin-7-yl)phenyl)acetamide, 7-bromo-N-(3,4,5-trimethoxyphenyl)thieno[3,2-d]pyrimidin-2-amine, (3-(2-(3,4,5-trimethoxyphenylamino)thieno[3,2-d]pyrimidin-7-yl)phenyl)methanol, (4-(2-(3,4,5-trimethoxyphenylamino)thieno[3,2-d]pyrimidin-7-yl)phenyl)5 methanol, (3-(2-(4-morpholinophenylamino)thieno[3,2-d]pyrimidin-7-yl)phenyl)methanol, (4-(2-(4-morpholinophenylamino)thieno[3,2-d]pyrimidin-7-yl)phenyl)methanol, N-(pyrrolidin-1-yl)ethoxy)phenylamino)thieno[3,2-d]pyrimidin-7-yl)benzyl)methanesulfonamide, tert-butylmorpholinomethyl)phenylamino)thieno[3,2-d]pyrimidin-7-yl)benzylcarbamate, N-(4-(morpholinomethyl)phenyl)-7-(3-(piperazin-1-yl)phenyl)thieno[3,2-d]pyrimidin-2-amine, 7-(6-(2-morpholinoethylamino)pyridin-3-yl)-N-(3,4,5-trimethoxyphenyl)thieno[3,2-d]pyrimidin-2-amine, 7-(2-ethylphenyl)-N-(4-(2-(pyrrolidin-1-yl)ethoxy)phenyl)thieno[3,2-d]pyrimidin-2-amine, 7-(4-(aminomethyl)phenyl)-N-(4-(morpholinomethyl)phenyl)thieno[3,2-d]pyrimidin-2-amine, N-(4-(1-ethylpiperidin-4-yloxy)phenyl)-7-(1H-pyrazol-4-yl)thieno[3,2-d]pyrimidin-2-amine, N-(2,4-dimethoxyphenyl)-7-phenylthieno[3,2-d]pyrimidin-2-amine, 7-bromo-N-(3,4-dimethoxyphenyl)thieno[3,2-d]pyrimidin-2-amine, N-(3,4-dimethoxyphenyl)-7-phenylthieno[3,2-d]pyrimidin-2-amine, and pharmaceutically acceptable salts and prodrugs thereof.

3. The method of claim 1, further comprising the coadministration of
   a) at least one each of an adenine, cytosine, thymidine, and guanine nucleoside antiviral agent, or
   b) at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors.

4. The method of claim 3, wherein the thymidine nucleoside antiretroviral agent is zidovudine (AZT).

5. The method of claim 3, wherein the nucleoside antiretroviral agents comprise:
   a) (−)-FTC or 3TC,
   b) TDF,
   c) DAPD or APD,
   d) AZT, and
   e) a NNRTI, a protease inhibitor, or an integrase inhibitor.

6. The method of claim 3, wherein the NNRTI is Sustiva, the protease inhibitor is Kaletra, or the integrase inhibitor is Raltegravir or Elvitegravir.

7. The method of claim 3, wherein the compound of Formula A or B, and the at least one each of an adenine, cytosine, thymidine, and guanine antiviral agent, or at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors, are administered in combination.

8. The method of claim 1, wherein the compound of Formula A is

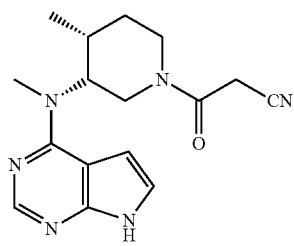

or a pharmaceutically acceptable salt or prodrug thereof.

9. The method of claim 1, wherein the compound of Formula B is

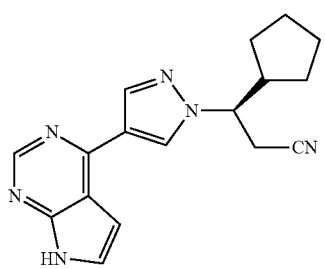 [SMILES: N#CC[C@H](C1CCCC1)n1cc(-c2ncnc3[nH]ccc23)cn1]

or a pharmaceutically acceptable salt or prodrug thereof.

10. The method of claim 1, further comprising the co-administration of a macrophage depleting agent.

11. A method for treating or preventing AIDS-related complex (ARC), persistent generalized lymphadenopathy (PGL), anti-HIV antibody positive and HIV-positive conditions, Kaposi's sarcoma, thrombocytopenia purpurea or HIV-1-related opportunistic infections, comprising administering to a patient in need thereof an effective amount of a compound of Formula A:

Formula A

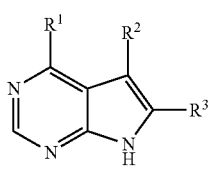

wherein:
or the pharmaceutically acceptable salt thereof; wherein R is a group of the formula

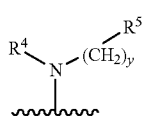

wherein y is 0, 1 or 2;
$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO-NH, $(C_1-C_6)$alkylamino-CO-, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$-CO-O-, $R^{15}R^{16}N$-CO-$(C_1-C_6)$alkyl, $(C_1-C_6)$alkyl-S(O)$_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}(C_1-C_6)$alkyl wherein m is 0, 1 or 2 and $R^{15}$ and $R^{16}$ are each independently selected from hydrogen or $(C_1-C_6)$alkyl; or a group of the formula

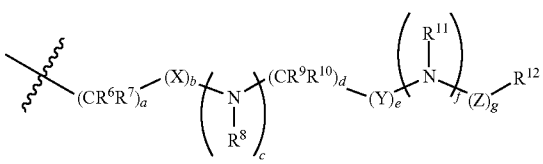

wherein a is 0, 1, 2, 3 or 4;
b, c, e, f and g are each independently 0 or 1;
d is 0, 1, 2, or 3;
X is $S(O)_n$ wherein n is 0, 1 or 2; oxygen, carbonyl or —C(=N-cyano)-;
Y is $S(O)_n$ wherein n is 0, 1 or 2; or carbonyl; and
Z is carbonyl, C(O)O—, C(O)NR— or $S(O)_n$ wherein n is 0, 1 or 2;
$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, $R^{15}C(O)NH$, $R^{15}OC(O)NH$, $R^{15}NHC(O)NH$, ($C_1$-$C_6$)alkyl-S(O)$_m$, ($C_1$-$C_6$)alkyl-S(O)$_m$—($C_1$-$C_6$)alkyl, $R^{15}R^{16}NS(O)_m$, $R^{15}R^{16}NS(O)_m$($C_1$-$C_6$)alkyl, $R^{15}S(O)_mR^{16}N$, $R^{15}S(O)_mR^{16}N(C_1$-$C_6$)alkyl wherein m is 0, 1 or 2 and $R^{15}$ and $R^{16}$ are each independently selected from hydrogen or ($C_1$-$C_6$)alkyl;

$R^2$ and $R^3$ are each independently selected from the group consisting of hydrogen, deuterium, amino, halo, hydroxy, nitro, carboxy, ($C_2$-$C_6$)alkenyl, ($C_2$-$C_6$)alkynyl, trifluoromethyl, trifluoromethoxy, ($C_1$-$C_6$)alkyl, ($C_1$-$C_6$)alkoxy, ($C_3$-$C_{10}$)cycloalkyl wherein the alkyl, alkoxy or cycloalkyl groups are optionally substituted by one to three groups selected from halo, hydroxy, carboxy, amino ($C_1$-$C_6$)alkylthio, ($C_1$-$C_6$)alkylamino, (($C_1$-$C_6$)alkyl)$_2$amino, ($C_5$-$C_9$)heteroaryl, ($C_2$-$C_9$)heterocycloalkyl, ($C_3$-$C_9$)cycloalkyl or ($C_6$-$C_{10}$)aryl; or $R^2$ and $R^3$ are each independently ($C_3$-$C_{10}$)cycloalkyl, ($C_3$-$C_{10}$)cycloalkoxy, ($C_1$-$C_6$)alkylamino, (($C_1$-$C_6$)alkyl)$_2$amino, ($C_6$-$C_{10}$)arylamino, ($C_1$-$C_6$)alkylthio, ($C_6$-$C_{10}$)arylthio, ($C_1$-$C_6$)alkylsulfinyl, ($C_6$-$C_{10}$)arylsulfinyl, ($C_1$-$C_6$)alkylsulfonyl, ($C_6$-$C_{10}$)arylsulfonyl, ($C_1$-$C_6$)acyl, ($C_1$-$C_6$)alkoxy-CO—NH—, ($C_1$-$C_6$) alkylamino-CO—, ($C_5$-$C_9$)heteroaryl, ($C_2$-$C_9$) heterocycloalkyl or ($C_6$-$C_{10}$)aryl wherein the heteroaryl, heterocycloalkyl and aryl groups are optionally substituted by one to three halo, ($C_1$-$C_6$)alkyl, ($C_1$-$C_6$)alkyl-CO—NH—, ($C_1$-$C_6$)alkoxy-CO—NH—, ($C_1$-$C_6$)alkyl-CO—NH—($C_1$-$C_6$)alkyl, ($C_1$-$C_6$)alkoxy-CO—NH—($C_1$-$C_6$)alkyl, ($C_1$-$C_6$)alkoxy-CO—NH—($C_1$-$C_6$)alkoxy, carboxy, carboxy($C_1$-$C_6$)alkyl, carboxy($C_1$-$C_6$)alkoxy, benzyloxycarbonyl($C_1$-$C_6$)alkoxy, ($C_1$-$C_6$)alkoxycarbonyl($C_1$-$C_6$)alkoxy, ($C_6$-$C_{10}$)aryl, amino, amino($C_1$-$C_6$)alkyl, ($C_1$-$C_6$)alkoxycarbonylamino, ($C_6$-$C_{10}$)aryl($C_1$-$C_6$)alkoxycarbonylamino, ($C_1$-$C_6$)alkylamino, (($C_1$-$C_6$)alkyl)$_2$amino, ($C_1$-$C_6$)alkylamino($C_1$-$C_6$)alkyl, (($C_1$-$C_6$)alkyl)$_2$amino($C_1$-$C_6$)alkyl, hydroxy, ($C_1$-$C_6$)alkoxy, carboxy, carboxy($C_1$-$C_6$)alkyl, ($C_1$-$C_6$)alkoxycarbonyl, ($C_1$-$C_6$) alkoxycarbonyl($C_1$-$C_6$)alkyl, ($C_1$-$C_6$)alkoxy-CO—NH—, ($C_1$-$C_6$)alkyl-CO—NH—, cyano, ($C_5$-$C_9$) heterocycloalkyl, amino-CO—NH—, ($C_1$-$C_6$) alkylamino-CO—NH—, (($C_1$-$C_6$)alkyl)$_2$amino-CO—NH—, ($C_6$-$C_{10}$)arylamino-CO—NH—, ($C_5$-$C_9$) heteroarylamino-CO—NH—, ($C_1$-$C_6$)alkylamino-CO—NH—($C_1$-$C_6$)alkyl, (($C_1$-$C_6$)alkyl)$_2$amino-CO—NH—($C_1$-$C_6$)alkyl, ($C_6$-$C_{10}$)arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$) alkylsulfonylamino, ($C_1$-$C_6$)alkylsulfonylamino($C_1$-$C_6$)alkyl, ($C_6$-$C_{10}$)arylsulfonyl, ($C_6$-$C_{10}$) arylsulfonylamino, ($C_6$-$C_{10}$)arylsulfonylamino($C_1$-$C_6$)alkyl, ($C_1$-$C_6$)alkylsulfonylamino, ($C_1$-$C_6$) alkylsulfonylamino($C_1$-$C_6$)alkyl, ($C_5$-$C_9$)heteroaryl or ($C_2$-$C_9$)heterocycloalkyl;

or of Formula B:

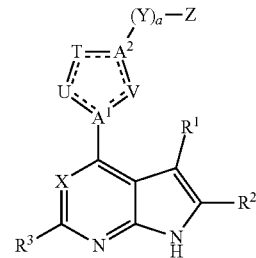

Formula B including pharmaceutically acceptable salt forms or prodrugs thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR_c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_p$ $OC(O)NR(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$ wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}alkyl)R$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $N_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R$, $NR^cS(O)_2R^b$, $C(=NOH)R$, $C(=NO(C_{1-6}$ alkyl))R, and $S(O)_2NR^cR^d$;

wherein when Z is H, n is 1;

or the —(Y)$_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$ $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —(W)$_m$-Q;

W is $C_{1-8}$ alkylenyl, $C_{2-8}$ alkenylenyl, $C_{2-8}$ alkynylenyl, O, S, C(O), C(O)NR$^{c'}$, C(O)O, OC(O), OC(O)NR$^{c'}$, NR$^{c'}$, NR$^{c'}$C(O)NR$^{d'}$, S(O), S(O)NR$^{c'}$, S(O)$_2$, or S(O)$_2$NR$^{c'}$;

Q is H, halo, CN, NO$_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, Cy$^2$, CN, NO$_2$, OR$^{a'}$, SR$^{a'}$, C(O)R$^{b'}$, C(O)NR$^{c'}$R$^{d'}$, C(O)OR$^{a'}$, OC(O)R$^{b'}$, OC(O)NR$^{c'}$R$^{d'}$, NR$^{c'}$R$^{d'}$, NR$^{c'}$C(O)R$^{b'}$, NR$^{c'}$C(O)NR$^{c'}$R$^{d'}$, NR$^{c'}$C(O)OR$^{a'}$, S(O)R$^{b'}$, S(O)NR$^{c'}$R$^{d'}$, S(O)$_2$R$^{b'}$, NR$^{c'}$S(O)$_2$R$^{b'}$, and S(O)$_2$NR$^{c'}$R$^{d'}$;

Cy$^1$ and Cy$^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$, NR$^{c''}$S(O)R$^{b''}$, NR$^{c''}$S(O)$_2$R$^{b''}$, S(O)R$^{b''}$, S(O)NR$^{c''}$R$^{d''}$, S(O)$_2$R$^{b''}$, and S(O)$_2$NR$^{c''}$R$^{d''}$;

R$^1$, R$^2$, R$^3$, and R$^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$OC(O)R$^8$, OC(O)NR$^9$R$^{10}$, NR$^9$R$^{10}$, NR$^9$C(O)R$^8$, NR$^c$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$;

R$^5$ is H, halo, $C_{1-4}$ alkyl, $C_{2-4}$ alkenyl, $C_{2-4}$ alkynyl, $C_{1-4}$ haloalkyl, halosulfanyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$;

R$^6$ is H, $C_{1-4}$ alkyl, $C_{2-4}$ alkenyl, $C_{2-4}$ alkynyl, $C_{1-4}$ haloalkyl, OR$^7$, C(O)R$^8$, C(O)NR$^9$R$^{10}$, C(O)OR$^7$, S(O)R$^8$, S(O)NR$^9$R$^{10}$, S(O)$_2$R$^8$, or S(O)$_2$NR$^9$R$^{10}$;

R$^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

R$^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

R$^9$ and R$^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or R$^9$ and R$^{10}$ together with the N atom to which they are attached form a 4-, 5-, 6- or 7-membered heterocycloalkyl group;

R$^{11}$ and R$^{12}$ are independently selected from H and -E$^1$-E$^2$-E$^3$-E$^4$;

D$^1$ and E$^1$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

D$^2$ and E$^2$ are independently absent or independently selected from $C_{1-6}$ alkylene, $C_{2-6}$ alkenylene, $C_{2-6}$ alkynylene, (C$_{1-6}$ alkylene)$_r$-O—(C$_{1-6}$ alkylene)$_s$, (C$_{1-6}$ alkylene)$_r$-S—(C$_{1-6}$ alkylene)$_s$, (C$_{1-6}$ alkylene)$_r$-NR$^c$—(C$_{1-6}$ alkylene)$_s$, (C$_{1-6}$ alkylene)$_r$-CO—(C$_{1-6}$ alkylene)$_s$, (C$_{1-6}$ alkylene)$_r$-COO—(C$_{1-6}$ alkylene)$_s$, (C$_{1-6}$ alkylene)$_r$-CONR$^c$—(C$_{1-6}$ alkylene)$_s$, (C$_{1-6}$ alkylene)$_r$-SO—(C$_{1-6}$ alkylene)$_s$, (C$_{1-6}$ alkylene)$_r$-SO$_2$—(C$_{1-6}$ alkylene)$_s$, (C$_{1-6}$ alkylene)$_r$-SONR$^c$—(C$_{1-6}$ alkylene)$_s$, and (C$_{1-6}$ alkylene)$_r$-NR$^c$CONR$^f$—(C$_{1-6}$ alkylene)$_s$, wherein each of the $C_{1-6}$ alkylene, $C_{2-6}$ alkenylene, and $C_{2-6}$ alkynylene is optionally substituted by 1, 2 or 3 substituents independently selected from halo, CN, NO$_2$, N$_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

D$^3$ and E$^3$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

D$^4$ and E$^4$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, Cy$^1$, CN, NO$_2$, OR$^a$, SR$^a$, C(O)R$^b$, C(O)NR$^c$R$^a$, C(O)OR$^a$, OC(O)R$^b$OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

R$^b$ is H, Cy$^1$, —(C$_{1-6}$ alkyl)-Cy$^1$, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

R$^{a'}$ and R$^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^c$ and $R^d$ are independently selected from H, Cy, —($C_{1-6}$ alkyl)-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

or $R^c$ and $R^d$ together with the N atom to which they are attached form a 4-, 5-, 6- or 7-membered heterocycloalkyl group optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

$R^{c'}$ and $R^{d'}$ are independently selected from H, $C_{1-10}$ alkyl, $C_{1-6}$ haloalkyl, $C_{2-6}$ alkenyl, $C_2$-6 alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2 or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^i$ is H, CN, $NO_2$, or $C_{1-6}$ alkyl;

$R^e$ and $R^f$ are independently selected from H and $C_{1-6}$ alkyl;

$R^i$ is H, CN, or $NO_2$;

m is 0 or 1;

n is 0 or 1;

p is 0, 1, 2, 3, 4, 5, or 6;

q is 0, 1, 2, 3, 4, 5 or 6;

r is 0 or 1; and s is 0 or 1.

12. A method for treating or preventing AIDS-related complex (ARC), persistent generalized lymphadenopathy (PGL), anti-HIV antibody positive and HIV-positive conditions, Kaposi's sarcoma, thrombocytopenia purpurea or HIV-1-related opportunistic infections, comprising administering to a patient in need thereof an effective antiviral 5 amount of a JAK inhibitors selected from the group consisting of CEP-701 (Lestaurtinib), AZD1480, LY3009104/ INCB28050 Pacritinib/SB1518, VX-509, GLPG0634, INC424, R-348, CYT387, TG 10138, AEG 3482, 7-iodo-N-(4-morpholinophenyl)thieno[3,2-d]pyrimidin-2-amine, 7-(4-aminophenyl)-N-(4-morpholinophenyl)thieno[3,2-d]pyrimidin-2-amine, N-(4-(2-(4-morpholinophenylamino)thieno[3,2-d]pyrimidin-7-yl)phenyl)acryl amide, 7-(3-aminophenyl)-N-(4-morpholinophenyl)thieno[3,2-d]pyrimidin-2amine, N-(3-(2-(4-morpholinophenylamino)thieno[3,2-d]pyrimidin-7-yl)phen-yl)acrylamide, N-(4-morpholinophenyl)thieno[3,2-d]pyrimidin-2-amine, methyl 2-(4-morpholinophenylamino)thieno[3,2-d]pyrimidine-7-carboxylate, N-(4-morpholinophenyl)-5H-pyrrolo[3,2-d]pyrimidin-2-amine, 7-(4-amino-3-methoxyphenyl)-N-(4-morpholinophenyl)thieno[3,2-d]pyrimidin-2-amine, 4-(2-(4-morpholinophenylamino)thieno[3,2-d]pyrimidin-7-yl) benzenesulfonamide, N,Ndimethyl-3-(2-(4-morpholinophenylamino)thieno[3,2-d]pyrimidin-7-yl) benzenesulfonamide, 1-ethyl-3-(2-methoxy-4-(2-(4-morpholinophenylamino)thieno[3,2-d]pyrimidin-7-yl) phenyl)urea, N-(4-(2-(4-morpholinophenylamino)thieno[3, 2-d]pyrimidin-7-yl)phenyl)metha-nesulfonamide, 2-methoxy-4-(2-(4-morpholinophenylamino)thieno[3,2-d] pyrimidin-7-yl)pheno-1,2-cyano-N-(3-(2-(4-morpholinophenylamino)thieno[3,2-d]pyrimidin-7-yl-)phenyl)acetamide, N-(cyanomethyl)-2-(4-morpholinophenylamino) thieno[3,2-d]pyrimidine-7-carboxamide, N-(3-(2-(4-morpholinophenylamino)thieno[3,2-d]pyrimidin-7-yl) phenyl)methanesulfonamide, 1-ethyl-3-(4-(2-(4-morpholinophenylamino)thieno[3,2-d]pyrimidin-7-yl)-2-(-trifluoromethoxy)phenyl)urea N-(3-nitrophenyl)-7-phenylthieno[3,2-d]pyrimidin2-amine, 7-iodo-N-(3-nitrophenyl)thieno[3,2-d]pyrimidin-2-amine, N1-(7-(2-ethylphenyl)thieno[3,2-d]pyrimidin-2-yl)benzene-1,3-diamine, N-tert-butyl-3-(2-(4-morpholinophenylamino) thieno[3,2-d]pyrimidin-7-yl)be-nzenesulfonamide, N1-(7-iodothieno[3,2-d]pyrimidin-2-yl)benzene-1,3-diamine, 7-(4-amino-3-(trifluoromethoxy)phenyl)-N-(4-morpholinophenyl)thieno[3,2-d]pyrimidin-2-amine, 7-(2-ethylphenyl)-N-(4-morpholinophenyl)thieno[3,2-d]pyrimidin-2-amine, N-(3-(2-(4-morpholinophenylamino)thieno[3,2-d]pyrimidin-7-yl)phenyl-)acetamide, N-(cyanomethyl)-N-(3-(2-(4-morpholinophenylamino)thieno[3,2-d]pyrimidin-7-yl)phenyl)methanesulfonamide, N-(cyanomethyl)-N-(4-(2-(4-morpholinophenylamino)thieno[3,2-d]pyrimidin-7-yl)phenyl)methanesulfonamide, N-(3-(5-methyl-2-(4-morpholinophenylamino)-5H-pyrrolo[3,2-5d]pyrimidin-7-yl)phenyl)methanesulfonamide, 4-(5-methyl-2-(4-morpholinophenylamino)-5Hpyrrolo[3,2-d]pyrimidin-7-yl)b-enzenesulfonamide, N-(4-(5-methyl-2-(4-morpholinophenylamino)-5H-pyrrolo[3,2-d]pyrimidin-7-yl)phenyl)methanesulfonamide, 7-iodo-N-(4-morpholinophenyl)-5H-pyrrolo[3,2-d]pyrimidin-2-amine, 7-(2-isopropylphenyl)-N-(4-morpholinophenyl)thieno[3,2-d]pyrimidin-2-amine, 7-bromo-N-(4-morpholinophenyl)thieno[3,2-d]pyrimidin-2-amine N7-(2-isopropylphenyl)-N2-(4-morpholinophenyl)thieno[3,2-d]pyrimidine-2,7-diamine, N7-(4-isopropylphenyl)-N2-(4-morpholinophenyl)thieno[3,2-d]pyrimidine-2,7-diamine, 7-(5-amino-2-methylphenyl)-N-(4-morpholinophenyl)thieno[3,2-d]pyrimidin-2-amine, N-(cyanomethyl)-4-(2-(4-morpholinophenylamino)thieno[3,2-d]pyrimidin-7-yl)benzamide, 7-iodo-N-(3-morpholinophenyl)thieno[3,2-d]pyrimidin-2-amine, 7-(4-amino-3-nitrophenyl)-N-(4-morpholinophenyl)thieno[3,2-d]pyrimidin-2-amine, 7-(2-methoxypyridin-3-yl)-N-(4-morpholinophenyl)thieno[3,2-d]pyrimidin-2-amine, (3-(7-iodothieno[3,2-d]pyrimidin-2-ylamino)phenyl)methanol, N-tert-butyl-3-(2-(3-morpholinophenylamino)thieno[3,2-d]pyrimidin-7-yl)benzenesulfonamide, N-tertbutyl-3-(2-(3-(hydroxymethyl)phenylamino)thieno[3,2-d]pyrimidin-7-yl)benzenesulfonamide, N-(4-morpholinophenyl)-7-(4-nitrophenylthio)-5Hpyrrolo[3,2-d]pyrimidin-2-amine, N-tert-butyl-3-(2-(3,4,5-trimethoxyphenylamino)thieno[3,2-d]pyrimidin-7-yl)benzenesulfonamide, 7-(4-amino-3-nitrophenyl)-N-(3,4-dimethoxyphenyl)thieno[3,2-d]pyrimidin-2-amine N-(3,4-dimethoxyphenyl)-7-(2-methoxypyridin-3-yl)thieno[3,2-d]pyrimidin-2-amine, N-tert-butyl-3-(2-(3,4-dimethoxyphenylamino)thieno[3,2-d]pyrimidin-7-yl)benzenesulfonamide, 7-(2-aminopyrimidin-5-yl)-N-(3,4-dimethoxyphenyl)thieno[3,2-d]pyrimidin-2-amine, N-(3,4-dimethoxyphenyl)-7-(2,6-dimethoxypyridin-3-yl)thieno[3,2-d]pyrimidin-2-amine, N-(3,4-dimethoxyphenyl)-7-(2,4-dimethoxypyrimidin-5-yl)thieno[3,2-d]pyrimidin-2-amine, 7-iodo-N-(4-(morpholinomethyl)phenyl)thieno[3,2-d]pyrimidin-2-amine, N-tert-butyl-3-(2-(4-(morpholinomethyl)phenylamino)thieno[3,2-d]pyrimidin-7-yl)2-cyano-N-(4-methyl-3-(2-(4-morpholinophenylamino)thieno[3,2-d]pyrimidin-7-yl)phenyl)acetamide, ethyl 3-(2-(4-morpholinophenylamino)thieno[3,2-d]pyrimidin-7-yl)benzoate, 7-bromo-N-(4-(2-(pyrrolidin-1-yl)ethoxy)phenyl)thieno[3,2-d]pyrimidin-2-amine, N-(3-(2-(4-(2-(pyrrolidin-1-yl)ethoxy)phenylamino)thieno[3,2-d]pyrimidin-7-yl)phenyl)acetamide, N-(cyanomethyl)-5 3-(2-(4-morpholinophenylamino)thieno[3,2-d]pyrimidin-7-yl-)benzamide, N-tert-butyl-3-(2-(4-morpholinophenylamino)thieno[3,2-d]pyrimidin-7-yl)benzamide, N-tert-butyl-3-(2-(4-(1-ethylpiperidin-4-yloxy)phenylamino)thieno[3,2-d]pyrimidin-7-yl)benzenesulfonamide, tert-butyl-4-(2-(4-(morpholinomethyl)phenylamino)thieno[3,2-d]pyrimidin-7-yl)-1H-pyrazole-1-carboxylate, 7-bromo-N-(4-((4-ethylpiperazin-1-yl)methyl)phenyl)thieno[3,2-d]pyrimidin-2-amine, N-tert-butyl-3-(2-(4-((4-ethylpiperazin-1-yl)methyl)phenylamino)thieno[3,-2-d]pyrimidin-7-yl)benzenesulfonamide, N-(4-((4-ethylpiperazin-1-yl)methyl)phenyl)-7-(1H-pyrazol-4-yl)thieno[3,2-d]pyrimidin-2-amine, N-(cyanomethyl)-3-(2-(4-(morpholinomethyl)phenylamino)thieno[3,2-d]pyrimidin-7-yl)benzamide, N-tert-butyl-3-(2-(4-(2-(pyrrolidin-1-yl)ethoxy)phenylamino)thieno[3,2-d]-pyrimidin-7-yl)benzenesulfonamide, tert-butylpyrrolidin-1-yl)ethoxy)phenylamino)thieno[3,2-d]pyrimidin-7-yl)benzylcarbamate, 3-(2-(4-(2-(pyrrolidin-1-yl)ethoxy)phenylamino)thieno[3,2-d]pyrimidin-7-yl)benzenesulfonamide, 7-(3-chloro-4-fluorophenyl)-N-(4-(2-(pyrrolidin-1-yl)ethoxy)phenyl)thieno-[3,2-d]pyrimidin-2-amine, tert-butyl 4-(2-(4-(1-ethylpiperidin-4-yloxy)phenylamino)thieno[3,2-d]pyrimidin-7-yl-)-1H-pyrazole-1-carboxylate, 7-(benzo[d][1,3]dioxol-5-yl)-N-(4-(morpholinomethyl)phenyl)thieno[3,2-d]pyrimidin-2-amine, tert-butyl 5-(2-(4-(morpholinomethyl)phenylamino)thieno[3,2-d]pyrimidin-7-yl)-1H-indole-1-carboxylate, 7-(2-aminopyrimidin-5-yl)-N-(4-(morpholinomethyl)phenyl)thieno[3,2-d]pyrimidin-2-amine, tert-butyl 4-(2-(4-(morpholinomethyl)phenylamino)thieno[3,2-d]pyrimidin-7-yl)-5,6-di-hydropyridine-1(2H)-carboxylate, tert-butylmorpholinomethyl)phenylamino)thieno[3,2-d]pyrimidin-7-yl)benzylcarbamate, N-(3-(2-(4-(morpholinomethyl)phenylamino)thieno[3,2-d]pyrimidin-7-yl)-phenyl)acetamide, N-(4-(2-(4-(morpholinomethyl)phenylamino)thieno[3,2-d]pyrimidin-7-yl)phenyl) acetamide, N-(3-(2-(4-(morpholinomethyl)phenylamino)thieno[3,2-d]pyrimidin-7-yl)phenyl)methanesulfonamide, 7-(4-(4-methylpiperazin-1-yl)phenyl)-N-(4-(morpholinomethyl)phenyl)thieno-[3,2-d]pyrimidin-2-amine, N-(2-methoxy-4-(2-(4-(morpholinomethyl)phenylamino)thieno[3,2-d]pyrimidin-7-yl)phenyl)acetamide, 7-bromo-N-(3,4,5-trimethoxyphenyl)thieno[3,2-d]pyrimidin-2-amine, (3-(2-(3,4,5-trimethoxyphenylamino)thieno[3,2-d]pyrimidin-7-yl)phenyl)methanol, (4-(2-(3,4,5-trimethoxyphenylamino)thieno[3,2-d]pyrimidin-7-yl)phenyl)5 methanol, (3-(2-(4-morpholinophenylamino)thieno[3,2-d]pyrimidin-7-yl)phenyl)methanol, (4-(2-(4-morpholinophenylamino)thieno[3,2-d]pyrimidin-7-yl)phenyl)methanol, N-(pyrrolidin-1-yl)ethoxy)phenylamino)thieno[3,2-d]pyrimidin-7-yl)benzyl)methanesulfonamide, tert-butylmorpholinomethyl)phenylamino)thieno[3,2-d]pyrimidin-7-yl)benzylcarbamate, N-(4-(morpholinomethyl)phenyl)-7-(3-(piperazin-1-yl)phenyl)thieno[3,2-d]pyrimidin-2-amine, 7-(6-(2-morpholinoethylamino)pyridin-3-yl)-N-(3,4,5-trimethoxyphenyl)thieno[3,2-d]pyrimidin-2-amine, 7-(2-ethylphenyl)-N-(4-(2-(pyrrolidin-1-yl)ethoxy)phenyl)thieno[3,2-d]pyrimidin-2-amine, 7-(4-(aminomethyl)phenyl)-N-(4-(morpholinomethyl)phenyl)thieno[3,2-d]pyrimidin-2-amine, N-(4-(1-ethylpiperidin-4-yloxy)phenyl)-7-(1H-pyrazol-4-yl)thieno[3,2-d]pyrimidin-2-amine, N-(2,4-dimethoxyphenyl)-7-phenylthieno[3,2-d]pyrimidin-2-amine, 7-bromo-N-(3,4-dimethoxyphenyl)thieno[3,2-d]pyrimidin-2-amine, N-(3,4-dimethoxyphenyl)-7-phenylthieno[3,2-d]pyrimidin-2-amine, and pharmaceutically acceptable salts and prodrugs thereof.

13. The method of claim 11, further comprising the coadministration of
    a) at least one each of an adenine, cytosine, thymidine, and guanine nucleoside antiviral agent, or
    b) at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors.

14. The method of claim 13, wherein the thymidine nucleoside antiretroviral agent is zidovudine (AZT).

15. The method of claim 13, wherein the nucleoside antiretroviral agents comprise:
    a) (−)-FTC or 3TC,
    b) TDF,
    c) DAPD or APD,
    d) AZT, and
    e) a NNRTI, a protease inhibitor, or an integrase inhibitor.

16. The method of claim 13, wherein the NNRTI is Sustiva, the protease inhibitor is Kaletra, or the integrase inhibitor is Raltegravir or Elvitegravir.

17. The method of claim 13, wherein the compound of Formula A or B, and the at least one each of an adenine, cytosine, thymidine, and guanine nucleoside antiviral agent, or at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors, are administered in combination.

18. The method of claim 11, wherein the compound of Formula A is

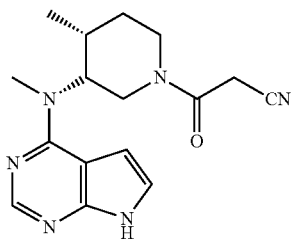

or a pharmaceutically acceptable salt or prodrug thereof.

19. The method of claim 11, wherein the compound of Formula B is

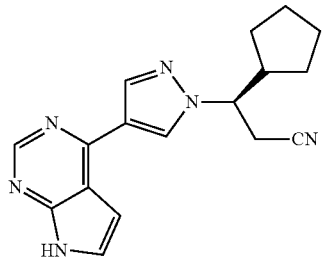 [SMILES: N#CC[C@H](C1CCCC1)n1cc(-c2ncnc3[nH]ccc23)cn1]

or a pharmaceutically acceptable salt or prodrug thereof.

20. The method of claim 11, further comprising the co-administration of a macrophage depleting agent.

SEQUENCE LISTING

```
<160> NUMBER OF SEQ ID NOS: 6

<210> SEQ ID NO 1
<211> LENGTH: 17
<212> TYPE: DNA
<213> ORGANISM: Human

<400> SEQUENCE: 1
tgcccgccat catccta                                                  17

<210> SEQ ID NO 2
<211> LENGTH: 21
<212> TYPE: DNA
<213> ORGANISM: human

<400> SEQUENCE: 2
tcctcatcgc cctcccatcc c                                             21

<210> SEQ ID NO 3
<211> LENGTH: 23
<212> TYPE: DNA
<213> ORGANISM: Human

<400> SEQUENCE: 3
cgtctgttat gtaaaggatg cgt                                           23

<210> SEQ ID NO 4
<211> LENGTH: 17
<212> TYPE: DNA
<213> ORGANISM: human

<400> SEQUENCE: 4
gcgcggctac agcttca                                                  17

<210> SEQ ID NO 5
<211> LENGTH: 18
<212> TYPE: DNA
<213> ORGANISM: human
```

```
<400> SEQUENCE: 5
caccacggcc gagcggga                                             18

<210> SEQ ID NO 6
<211> LENGTH: 22
<212> TYPE: DNA
<213> ORGANISM: human

<400> SEQUENCE: 6
tctccttaat gtcacgcacg at                                        22
```